(12) United States Patent
Yarger

(10) Patent No.: US 10,737,001 B2
(45) Date of Patent: Aug. 11, 2020

(54) ASPIRATORS, COMPONENTS THEREOF, AND ASSOCIATED CLEARANCES

(71) Applicant: SurgiMark, Inc., Yakima, WA (US)

(72) Inventor: David John Yarger, Hood River, OR (US)

(73) Assignee: SurgiMark, Inc., Yakima, WA (US)

( * ) Notice: Subject to any disclaimer, the term of this patent is extended or adjusted under 35 U.S.C. 154(b) by 270 days.

(21) Appl. No.: 15/655,391

(22) Filed: Jul. 20, 2017

(65) Prior Publication Data

US 2018/0021489 A1  Jan. 25, 2018

Related U.S. Application Data

(63) Continuation of application No. 15/216,310, filed on Jul. 21, 2016, now abandoned.

(60) Provisional application No. 62/364,653, filed on Jul. 20, 2016.

(51) Int. Cl.
*A61M 1/00* (2006.01)

(52) U.S. Cl.
CPC .......... *A61M 1/0086* (2014.02); *A61M 1/008* (2013.01); *A61M 1/0039* (2013.01); *A61M 2205/582* (2013.01)

(58) Field of Classification Search
CPC .. A61M 1/0039; A61M 1/008; A61M 1/0086; A61M 2205/582
See application file for complete search history.

(56) References Cited

U.S. PATENT DOCUMENTS

| | | | |
|---|---|---|---|
| 1,388,312 A | 8/1921 | Seeger |
| 1,596,754 A | 8/1926 | Moschelle |
| 1,928,992 A | 10/1933 | Masterman et al. |
| 2,220,493 A | 11/1940 | Pixler |
| 3,308,825 A | 3/1967 | Cruse |
| 3,416,532 A | 12/1968 | Grossman |
| 3,528,427 A | 9/1970 | Sheridan |
| 3,965,901 A | 6/1976 | Penny |
| 4,257,422 A | 3/1981 | Duncan |

(Continued)

FOREIGN PATENT DOCUMENTS

| | | |
|---|---|---|
| CA | 2428951 | 11/2003 |
| CA | 2585021 | 10/2007 |

(Continued)

*Primary Examiner* — Benjamin J Klein
(74) *Attorney, Agent, or Firm* — K&L Gates LLP

(57) ABSTRACT

In part, the disclosure relates to an aspirator having a handle that includes a suction connector extending from a proximal end face, a substantially cylindrical sleeve mount having an outer surface and a shoulder. A tubular member defining a bore and having flared end disposed in a suction head having one or more cantilevered protuberances can extend from the sleeve mount. The substantially cylindrical sleeve mount is in relief with respect to the shoulder and extends distally therefrom. The substantially cylindrical sleeve mount defines an aperture. The suction connector bore, bore of tubular member, inner cavity of handle and suction head bore define a fluid flow path or cavity. The aspirator can include a sleeve that receives the suction head. The sleeve engages and interferes with the sleeve mount. The suction head and sleeve's inner wall have one or more engineered clearances between them to enhance assembly.

22 Claims, 24 Drawing Sheets

(56) References Cited

U.S. PATENT DOCUMENTS

| | | |
|---|---|---|
| 4,398,910 A | 8/1983 | Blake et al. |
| 4,451,257 A | 5/1984 | Atchley |
| 4,465,481 A | 8/1984 | Blake |
| 4,490,138 A | 12/1984 | Lipsky et al. |
| 4,523,920 A | 6/1985 | Russo |
| 4,648,871 A | 3/1987 | Jacob |
| 4,650,463 A | 3/1987 | LeVeen et al. |
| 4,662,871 A | 5/1987 | Rafelson |
| 4,717,379 A | 1/1988 | Ekholmer |
| 4,767,404 A | 8/1988 | Renton |
| 4,867,747 A | 9/1989 | Yarger |
| 4,950,232 A | 8/1990 | Ruzicka et al. |
| 5,024,615 A | 6/1991 | Buchel |
| 5,116,310 A | 5/1992 | Seder et al. |
| 5,360,414 A | 11/1994 | Yarger |
| 5,690,487 A | 11/1997 | Whitehouse |
| 5,817,050 A | 10/1998 | Klein |
| 5,890,516 A | 4/1999 | Talamonti |
| 5,899,884 A | 5/1999 | Cover |
| 5,921,999 A | 7/1999 | Dileo |
| 6,099,513 A | 8/2000 | Spehalski |
| 6,478,789 B1 | 11/2002 | Spehalski et al. |
| 6,585,680 B2 | 7/2003 | Bugge |
| 6,866,657 B2 | 3/2005 | Shchervinsky |
| 6,893,424 B2 | 5/2005 | Shchervinsky |
| 7,066,903 B2 | 6/2006 | Yarger |
| 7,125,402 B1 | 10/2006 | Yarger |
| 7,776,004 B2 | 8/2010 | Yarger |
| 2003/0220611 A1* | 11/2003 | Yarger ............. A61M 1/008 604/122 |
| 2006/0095007 A1 | 5/2006 | Yarger |
| 2006/0259014 A1 | 11/2006 | Yarger |
| 2007/0203449 A1* | 8/2007 | Yarger ............. A61M 1/008 604/35 |
| 2011/0028939 A1* | 2/2011 | Yarger ............. A61M 1/008 604/523 |

FOREIGN PATENT DOCUMENTS

| | | |
|---|---|---|
| CN | 101085388 | 12/2007 |
| EP | 0457220 | 5/1991 |
| EP | 1364665 | 11/2003 |
| EP | 1847280 | 10/2007 |
| FR | 2170858 | 9/1973 |
| GB | 1531416 | 11/1978 |
| WO | 96/04950 | 2/1996 |

* cited by examiner

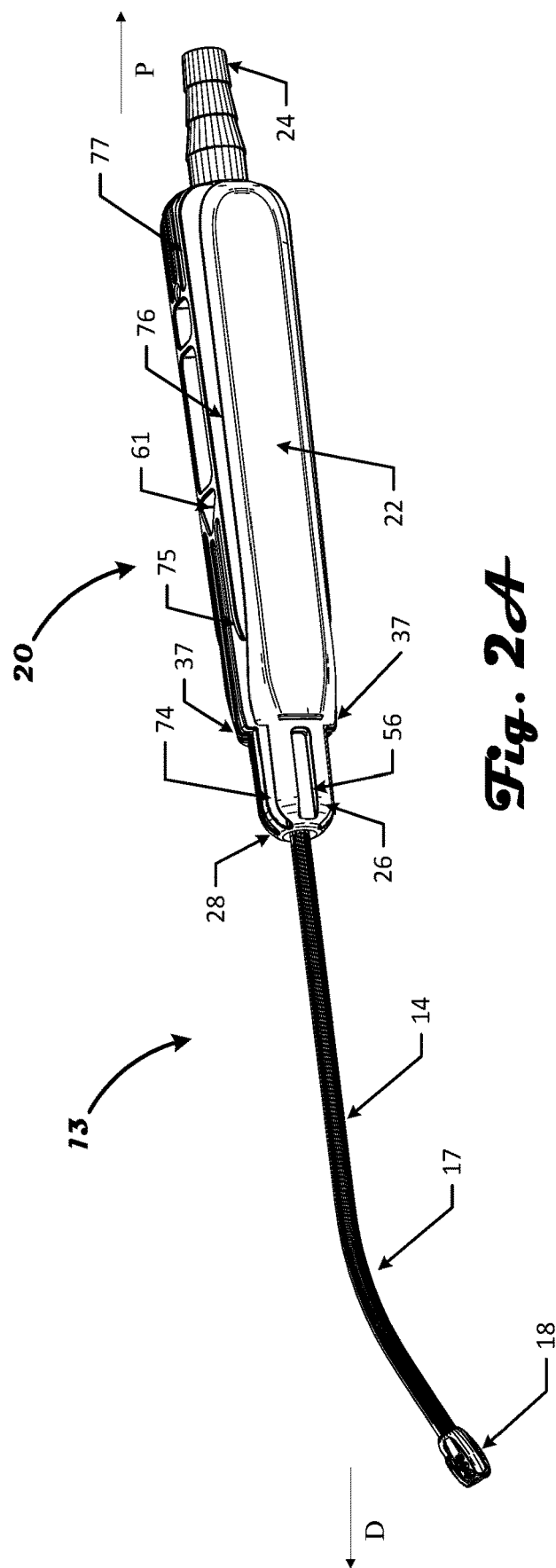
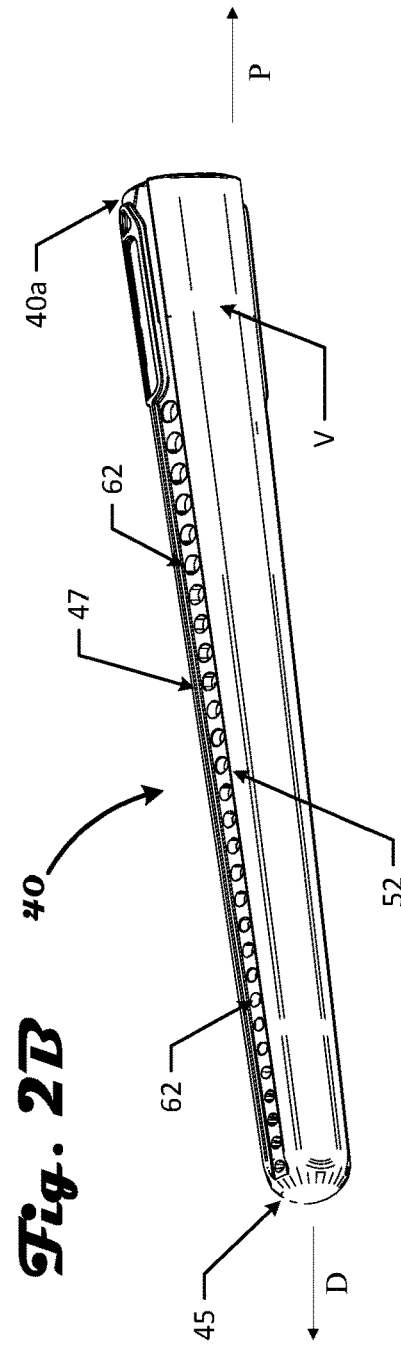
Fig. 2A
Fig. 2B

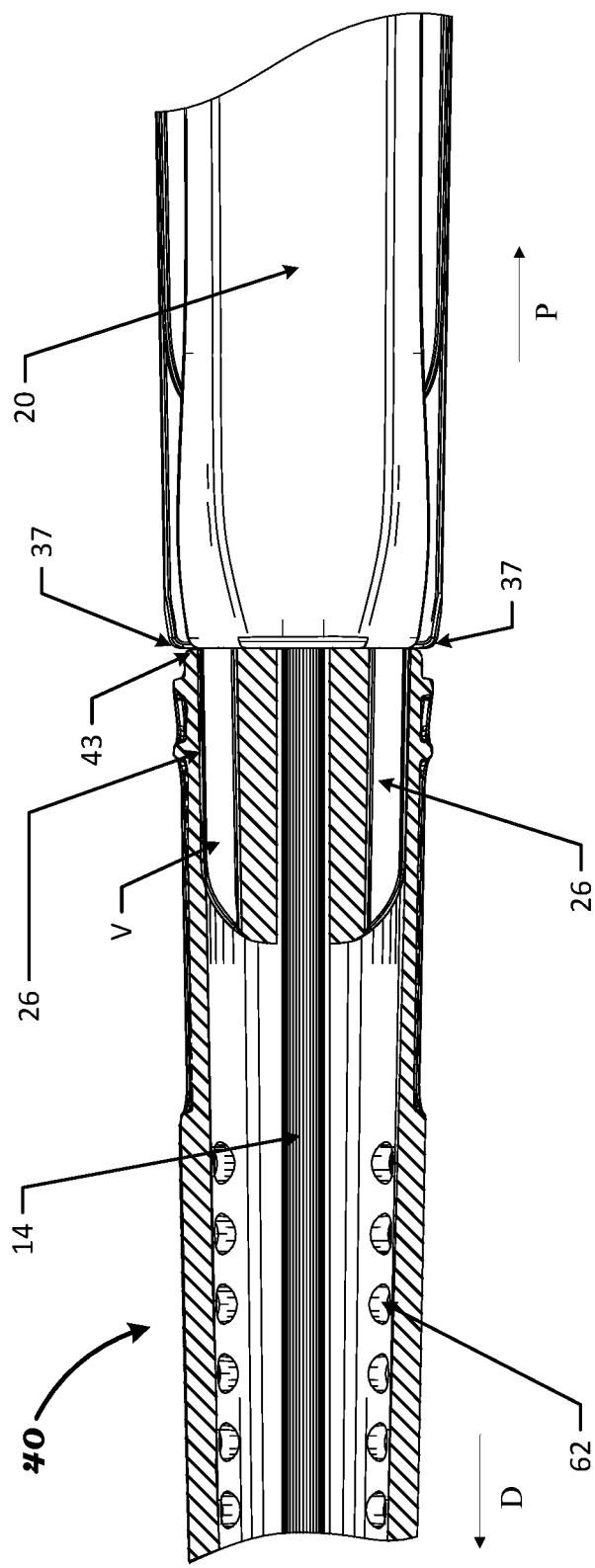

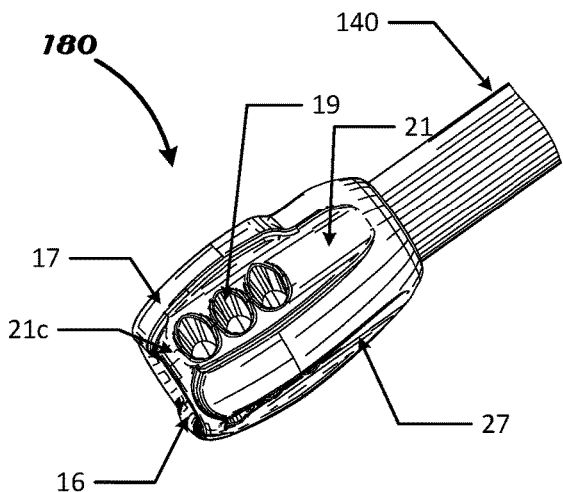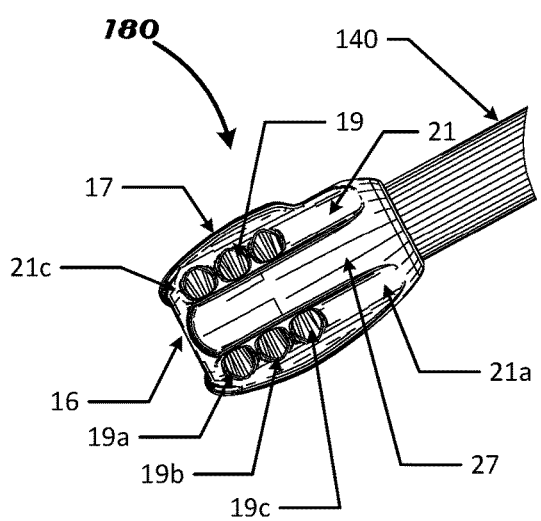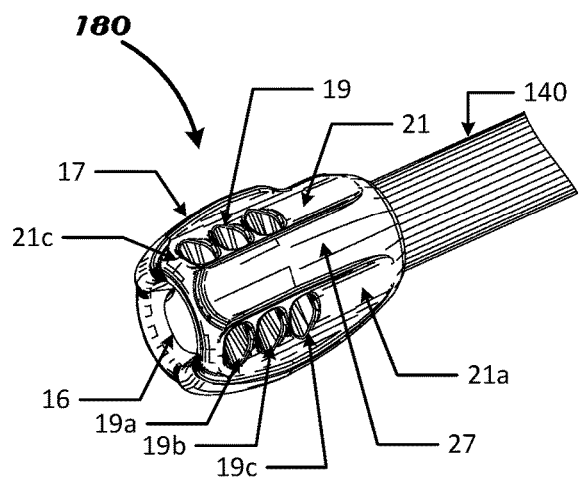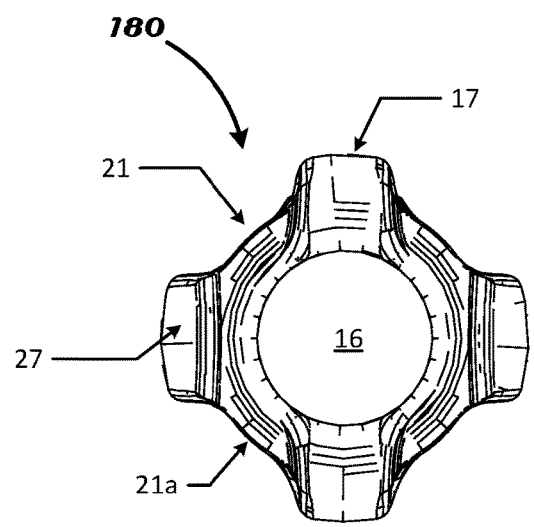
Fig. 5A
Fig. 5B
Fig. 5C
Fig. 5D

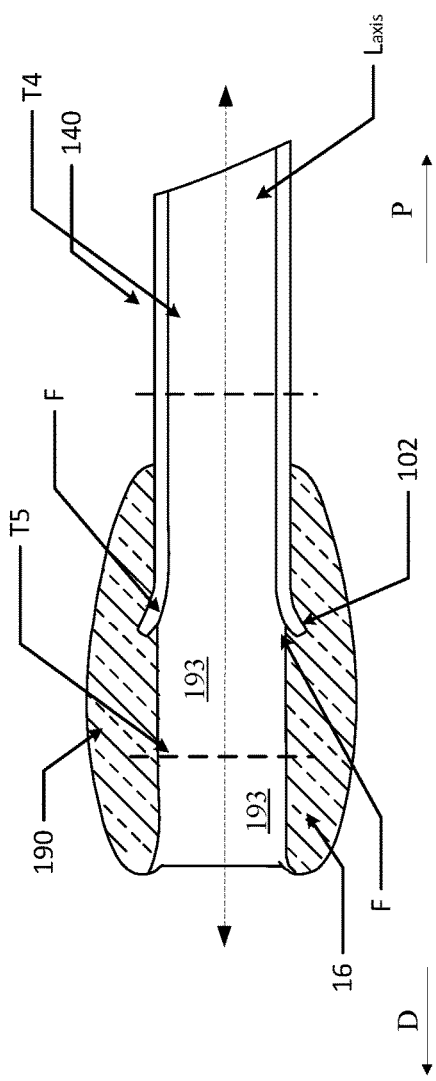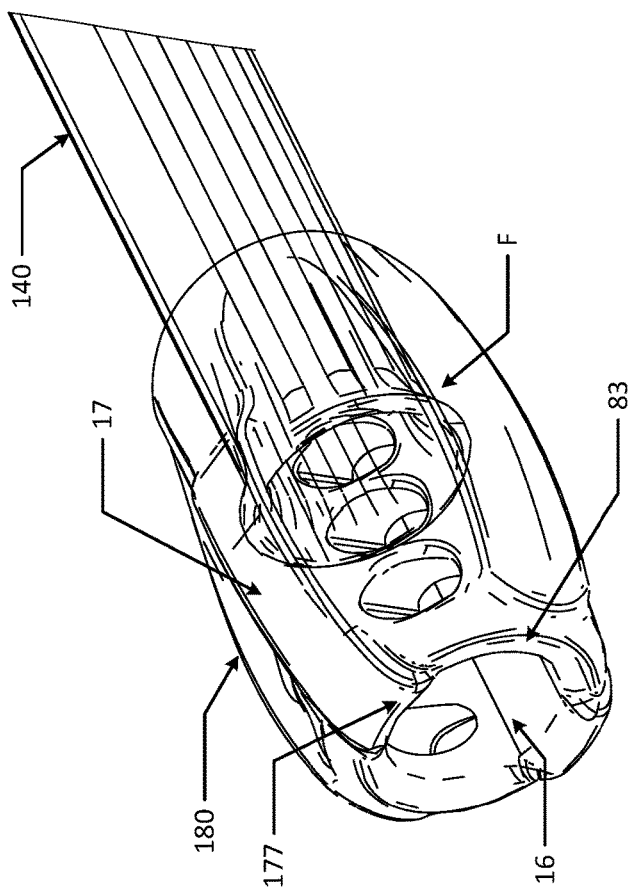

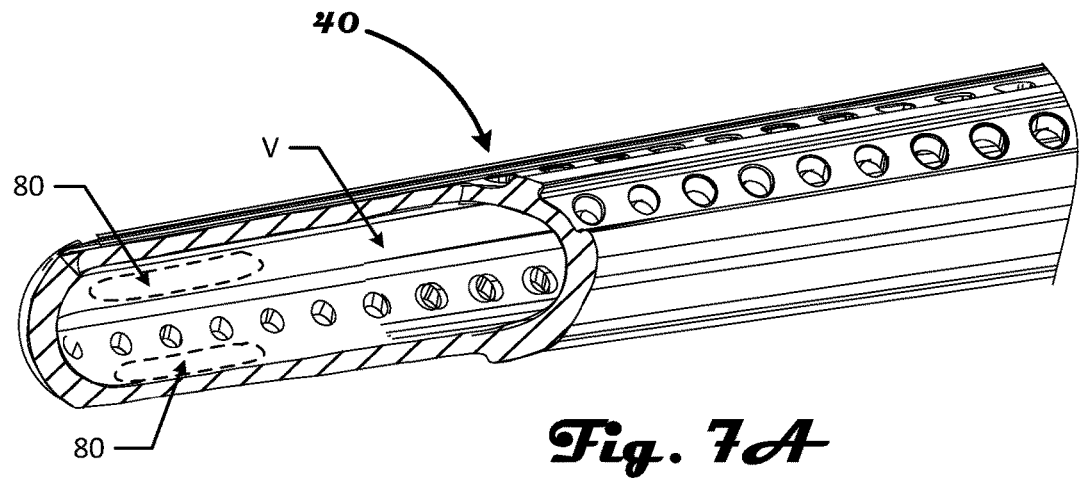
Fig. 7A
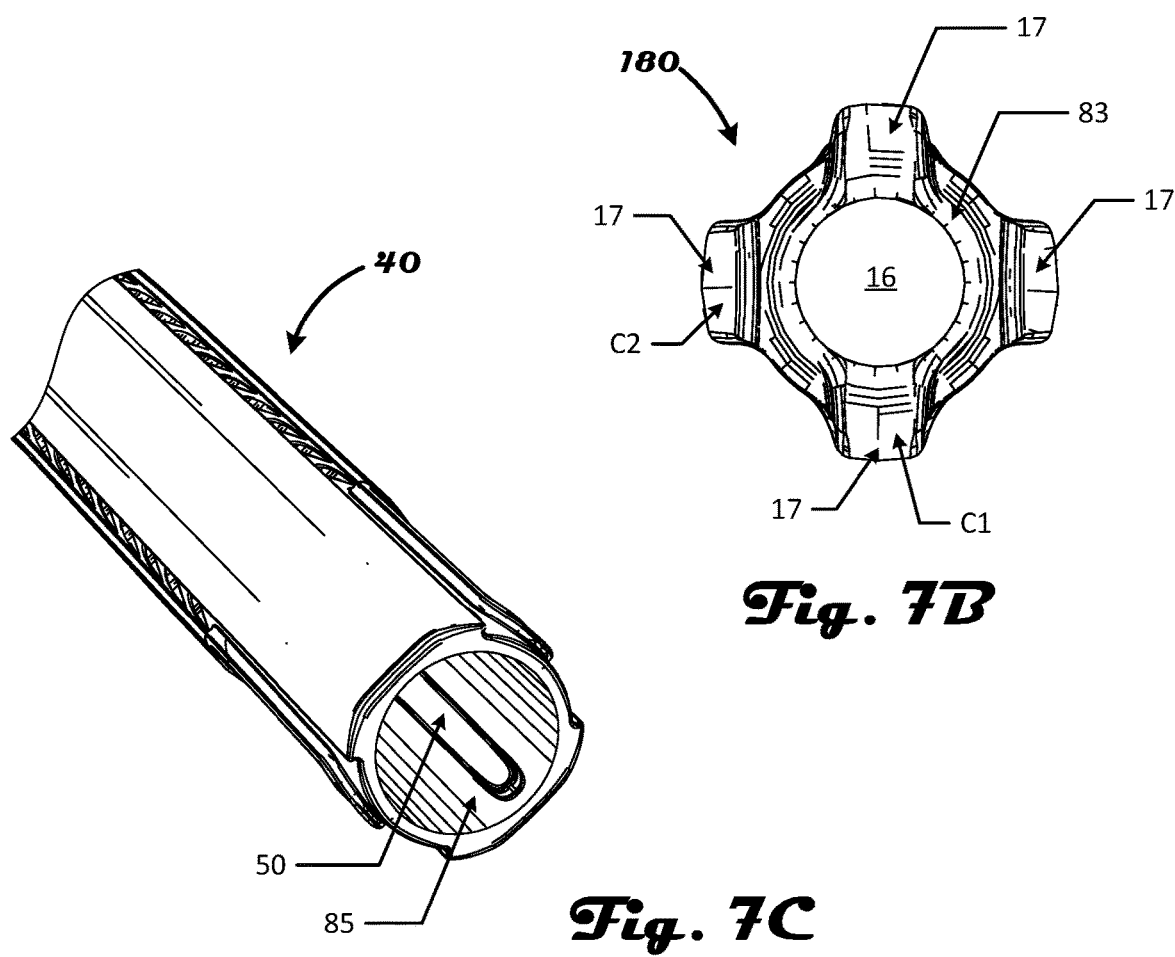
Fig. 7B
Fig. 7C

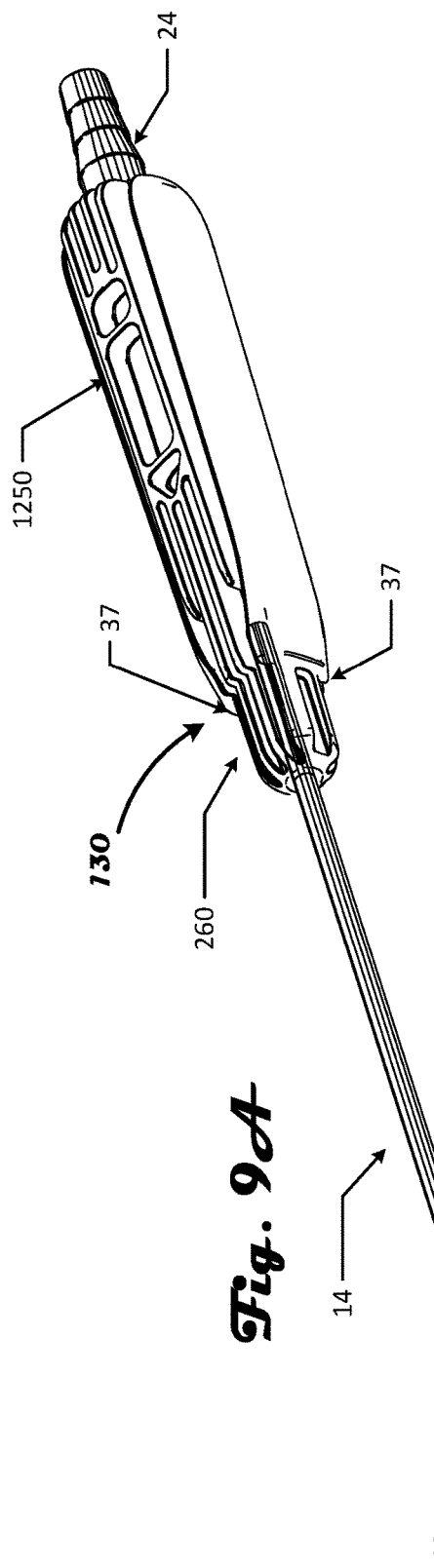
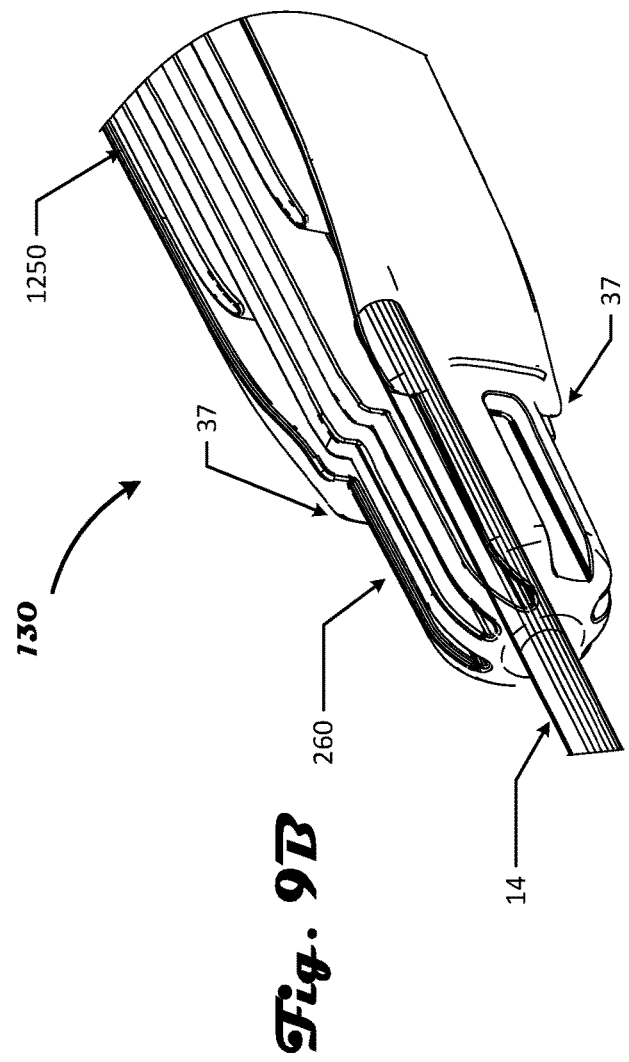

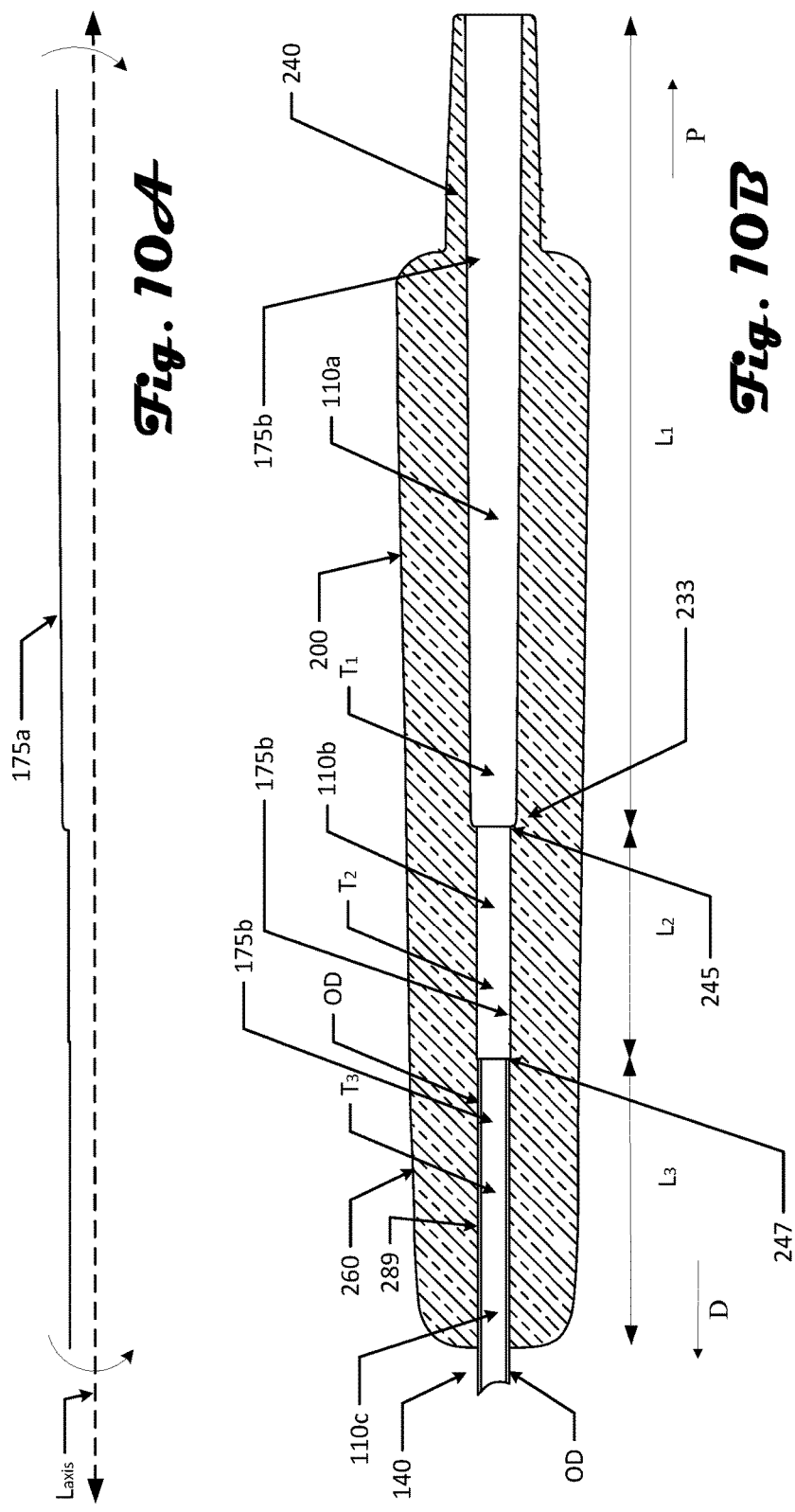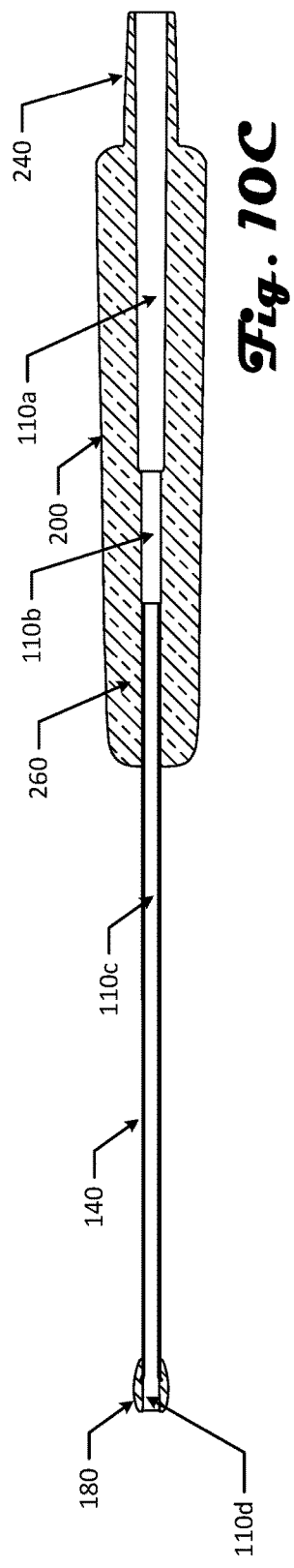

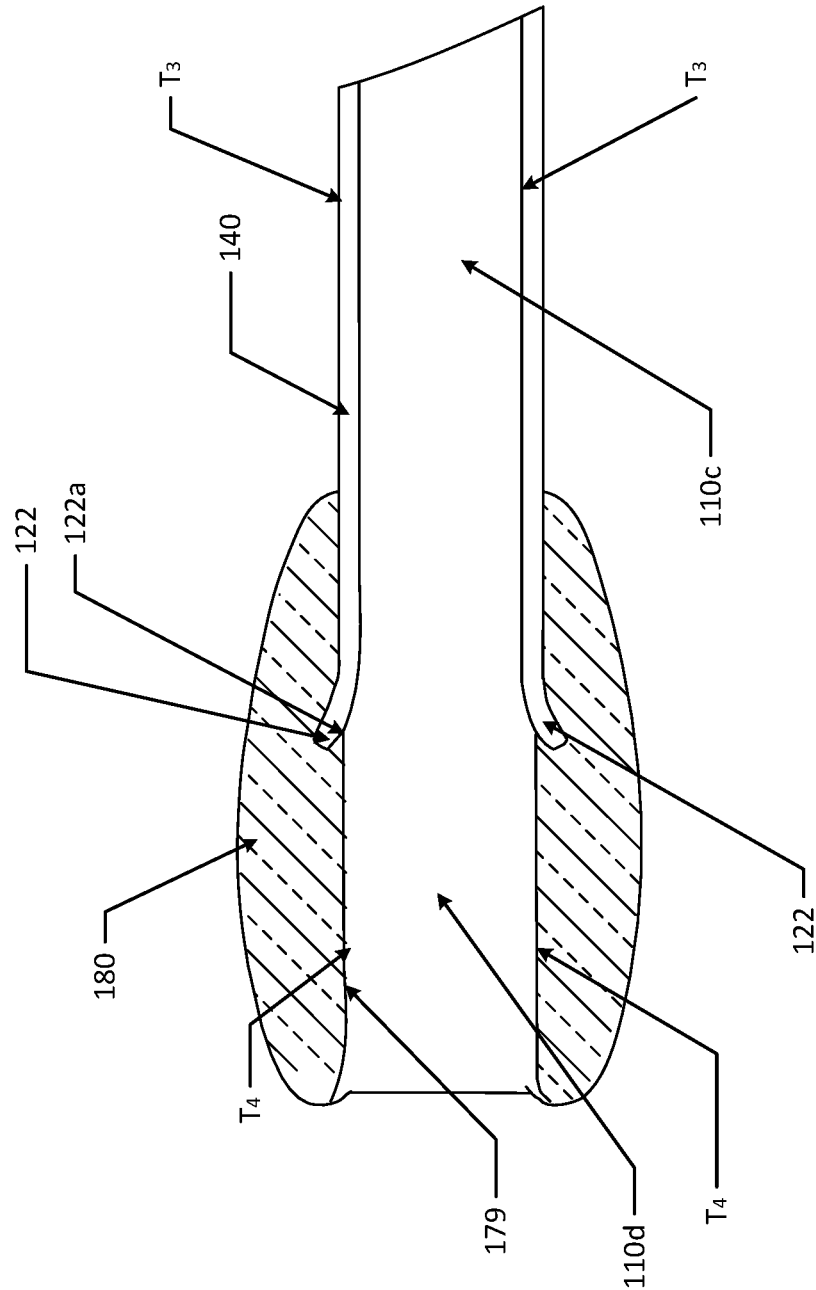

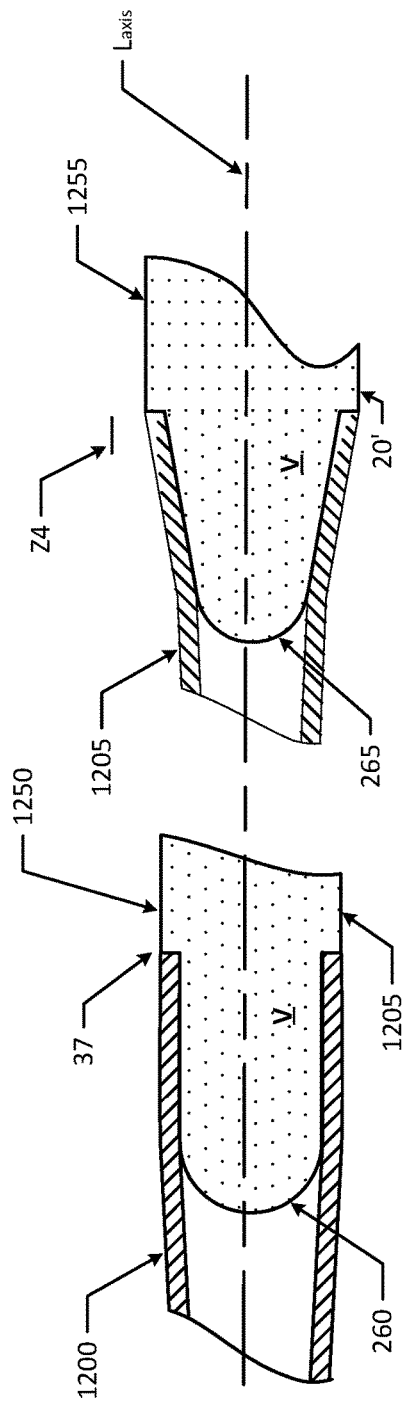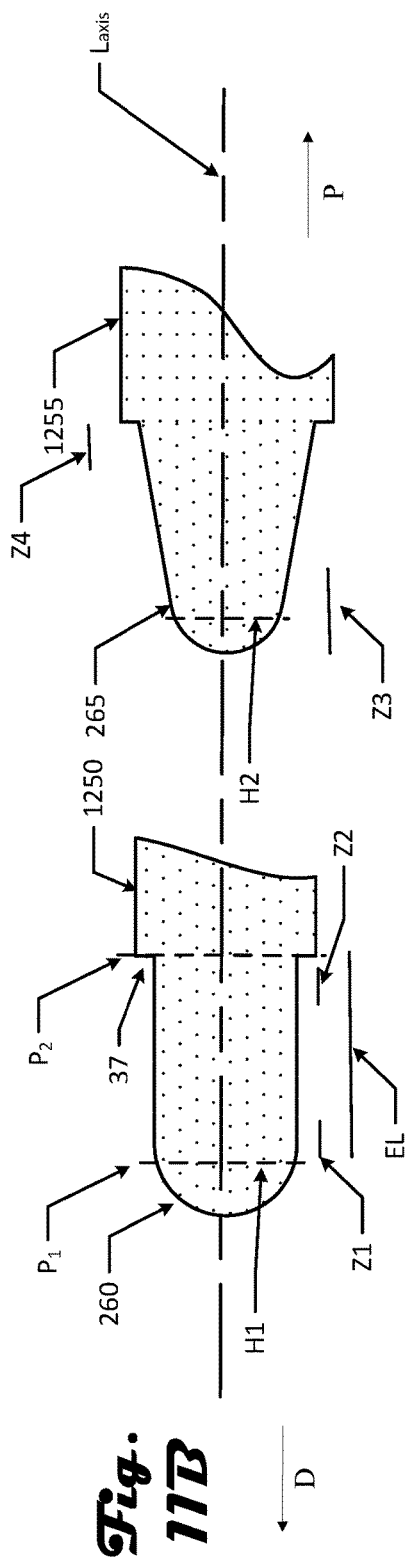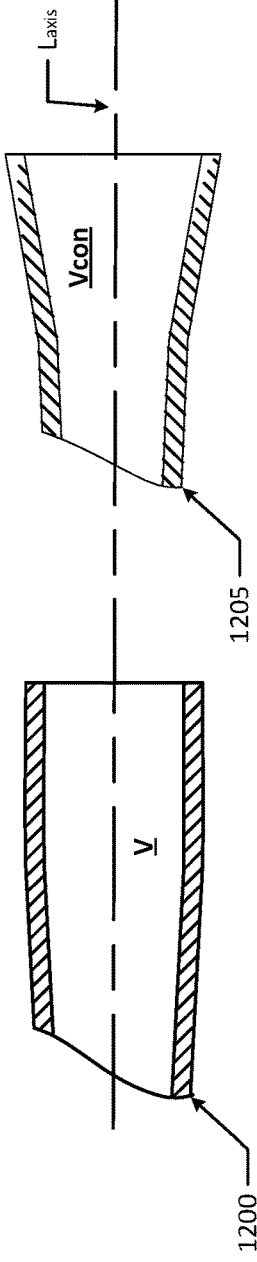

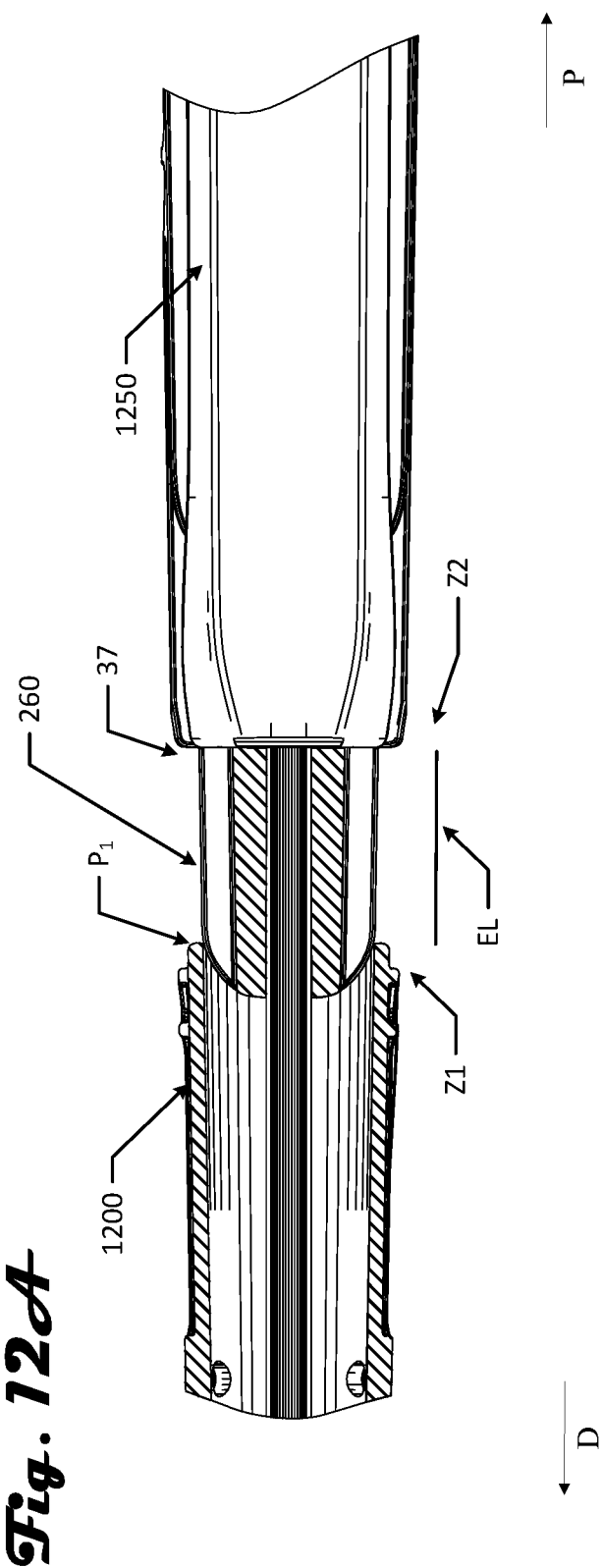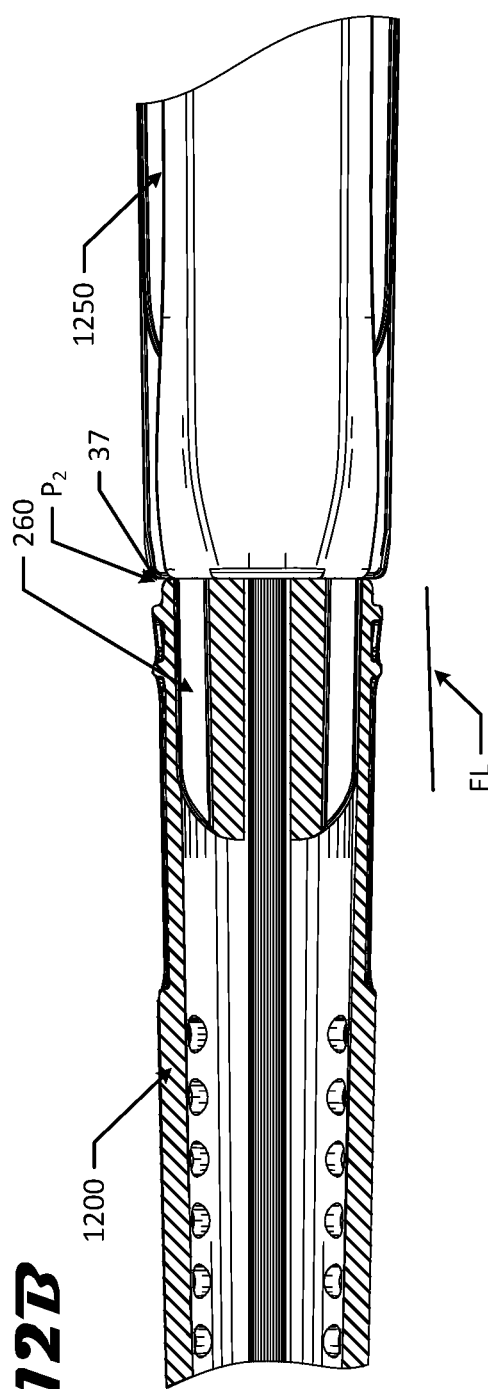

ASPIRATORS, COMPONENTS THEREOF, AND ASSOCIATED CLEARANCES

CROSS REFERENCE TO PRIOR APPLICATIONS

This application is a continuation of U.S. patent application Ser. No. 15/216,310 filed on Jul. 21, 2016 which claims the benefit of priority under 35 U.S.C. 119(e) from U.S. Provisional Application No. 62/364,653 filed on Jul. 20, 2016, the disclosures of which are herein incorporated by reference in their entirety.

BACKGROUND

A number of different devices may be used to remove fluids from a cavity, or other region of a patient, during a medical procedure. Often these devices will implement removal via suction. In general, devices used for producing suction, moving material by suction, or collecting material by suction, such as various types of aspirators, have remained largely the same since their initial development. Typically, a hollow tubular instrument is connected to a partial vacuum. The partial vacuum creates suction through the tubular instrument, thus removing fluid, tissue, or other material from a cavity or region of the body.

An aspirator typically includes a tip that is inserted into a surgical site, wound, or other bodily hole. The tip is generally elongated in shape and may include a handheld or grip section to facilitate using the aspirator. The proximal end of the tip is connected to a tube connected to a suction pump, providing the partial vacuum and thus suction to the tip. During use, the distal end of the aspirator tip is inserted into the patient. This distal end may have one or more openings into which gases, fluids, and materials may flow.

During operation, pieces of tissue and other debris may be suspended in the bodily fluid, thus clogging the aspirator. In addition, as is typically the case, surgical irrigation is used to wash a wound, tissues, organs and surgical cavities as part of various medical procedures. As a result, irrigation solution is introduced into the body, which is typically removed at a later stage. Various materials can also become entrained in the irrigation solution. There are various ways in which fluid flow can be interrupted or aspirator ports can be clogged during aspirator operation.

For example, openings at an end of the aspirator, the location where fluid first enters the device, are particularly vulnerable to clogging. One solution to this problem involves covering the distal end of the aspirator with a sleeve formed with a plurality of small holes. The plurality of small holes may prevent the tissue from reaching the opening of the aspirator. However, the plurality of small holes may still allow the fluid sleeve to become clogged. As the fluid sleeve becomes clogged, suction is no longer distributed uniformly among the remaining unclogged holes. This condition may create additional undesirable suction in a particular area, thus pulling surrounding tissue into the holes of the sleeve and simultaneously blocking or otherwise reducing the suctioning of unwanted material during the procedure.

One solution to this problem of clogging involves including additional holes in the end of the aspirator, near the connection between the sleeve and the aspirator. Because these additional holes are spaced from the wound, bodily hole, or surgical site, the additional holes are less likely to become clogged with tissue or debris. However, these holes are often vulnerable to obstruction by the hands or fingers of the user (e.g., by the hand holding the aspirator). Likewise, these holes may be obstructed or blocked when resting the aspirator and sleeve combination against another object, such as the patient's body, a table, or dressings surrounding the surgical site. Further, given the introduction of an irrigation solution and the entrainment of material therein, the potential exists for unintentionally suction applied to tissue and tearing at tissue surface or otherwise damaging it through the process of removing unwanted material from a surgical site using a suction device.

Therefore, a need exists for improved surgical aspirator and sleeve combinations that address these challenges and others relating to a user's tactile user experience when using such combinations and as otherwise described in more detail herein.

SUMMARY

In part, the disclosure relates to an aspirator having a handle that includes a suction connector extending from a proximal end face, a substantially cylindrical sleeve mount having an outer surface and a shoulder. A tubular member defining a bore and having flared end disposed in a suction head having one or more cantilevered protuberances can extend from the sleeve mount. The substantially cylindrical sleeve mount is in relief with respect to the shoulder and extends distally therefrom. The substantially cylindrical sleeve mount defines an aperture. The suction connector bore, bore of tubular member, inner cavity of handle and suction head bore define a fluid flow path or cavity. The aspirator can include a sleeve that receives the suction head. The sleeve engages and interferes with the sleeve mount. The suction head and sleeve's inner wall have one or more engineered clearances between them to enhance assembly. In one embodiment, the disclosure relates to a sleeve and aspirator combination or assembly. In one embodiment, the disclosure relates to a sleeveless actuator or suction device.

In part, the disclosure relates to various aspirator interference fit and assembly features and related embodiments.

In part the disclosure relates to an aspirator. The aspirator includes an elongate handle defining an fluid flow cavity, the elongate handle includes a proximal end face, a suction connector extending from the proximal end face, a substantially cylindrical sleeve mount includes an outer surface, and a shoulder, wherein the substantially cylindrical sleeve mount is in relief with respect to the shoulder and extends distally therefrom, wherein the substantially cylindrical sleeve mount defines an aperture, wherein the suction connector defines a suction connector bore, the suction connector bore in fluid communication with the aperture and fluid flow cavity.

The aspirator may also include a tubular member extending from the aperture, wherein the tubular member includes a proximal tube end and a distal tube end, wherein the proximal tube end is disposed in and secured by the handle, the tubular member defining a tubular member bore, the tubular member bore in fluid communication with the flow cavity and suction connector bore. The aspirator may also include an elastic sleeve, the elastic sleeve defining a plurality of vent holes, a sleeve lumen and a sleeve inner wall, the elastic sleeve includes a sleeve tip and a sleeve rim, wherein the sleeve rim defines a sleeve opening.

In one embodiment, the substantially cylindrical sleeve mount includes a mount thickness and a mount length, wherein the mount thickness and mount length are sized such that during sleeve installation on the sleeve mount the sleeve inner wall interferes with the outer surface of the sleeve mount upon the substantially cylindrical sleeve mount entering the sleeve lumen. In one embodiment, interference between sleeve inner wall and the outer surface continues along the mount length during the installation, wherein the installation is complete when the sleeve rim contacts the shoulder. In one embodiment, the aspirator may also include an elastic sleeve, the elastic sleeve defining a plurality of vent holes, a sleeve lumen and a sleeve inner wall, the elastic sleeve includes a sleeve tip and a sleeve rim, wherein the sleeve rim defines a sleeve opening, wherein the sleeve lumen is sized to receive the tubular member and to interfere with the outer surface of the sleeve mount upon the sleeve mount entering the sleeve lumen.

In one embodiment, the interference between sleeve inner wall and the outer surface continues along an engagement length during installation, wherein the installation is complete when the sleeve rim contacts at the shoulder. In one embodiment, the substantially cylindrical sleeve mount has a longitudinal axis, wherein an angle of taper of the outer surface of the substantially cylindrical sleeve mount measured relative to the longitudinal axis is less than about 2 degrees. In one embodiment, a sleeve engagement zone is defined by a region of overlap between outer surface and sleeve inner wall wherein interference between the elastic sleeve and substantially cylindrical sleeve mount occurs in the sleeve engagement zone. In one embodiment, the distal tube end is flared.

The aspirator may also include a suction head includes a body, a distal suction head end face and a proximal suction head end face, the suction head attached to the distal tube end; the body defining a primary opening and a suction head bore, the distal suction head end face surrounding the primary opening, the proximal suction head end face defining an output aperture, the output aperture in fluid communication with the suction head bore and the primary opening; and a plurality of protuberances disposed radially around the primary opening, each protuberance includes a first region and a second region, the first region cantilevered relative to the distal end face and extending distally relative to the primary opening, the second region extending from body to define a ridge.

The aspirator may also include a suction head defining an opening and a suction head bore, the opening in fluid communication with the suction head bore, the suction head attached to the distal tube end, the suction head includes a plurality of protuberances symmetrically arranged around the opening, each of the protuberances being an extension of a surface of the body in or more directions. In one embodiment, the fluid flow cavity transports one or more fluids including, without limitation, liquids, gases, and the foregoing with one or more solid materials disposed therein.

In one embodiment, the flow cavity of the handle is also defined by a proximal cavity, a distal cavity, and a middle cavity disposed between the distal cavity and the proximal cavity. In one embodiment, a diameter of the middle cavity is less than diameter of proximal cavity at interface of middle cavity and proximal cavity. The aspirator may also include a suction head attached to the distal tube end, wherein an engineered clearance distance is defined between a surface of the suction head and an inner surface of the sleeve such that a skewing angle is constrained when elastic sleeve is installed on handle, wherein the tubular member includes a bend.

In one embodiment, the fluid flow cavity is further defined by the suction connector bore; an elongate section of the tubular member bore disposed in the handle and in fluid communication with the suction connector bore; and a transitional cavity disposed between the suction connector bore and the elongate section of the tubular member bore. The transitional cavity is disposed within the handle in one embodiment. In one embodiment, a diameter of the transitional cavity is less than a diameter of the suction connector bore at interface of transitional cavity and suction connector bore.

In one embodiment, the skewing angle is defined by longitudinal axis of the tubular member proximal to the bend and longitudinal axis of sleeve distal to the bend. The aspirator may also include a tubular member defining a bend, the tubular member includes a proximal tube end and a distal tube end, the proximal tube end disposed in the handle, the tubular member extending from substantially cylindrical sleeve mount, wherein a section of the tubular member distal to the bend defines a tubular longitudinal axis, wherein the substantially cylindrical sleeve mount is sized to receive an elastic sleeve such that the bend is disposed within the sleeve.

In one embodiment, a section of the elastic sleeve distal to the bend defines a sleeve longitudinal axis, wherein a clearance is defined between a sleeve inner surface of the elastic sleeve and an outer surface of the tubular member by a skewing angle between the longitudinal axis and the sleeve longitudinal axis.

In one embodiment, the interference is a nominal interference of the sleeve inner wall to a mating diameter of the outer surface of the sleeve mount, wherein the nominal interference ranges from about 0.010 inches to about 0.020 inches. In one embodiment, the engagement length ranges from about 0.400 to about 0.800 inches.

In part, the disclosure relates to a method of providing tactile feedback for an aspirator. The method includes providing an aspirator sleeve includes a sleeve wall, the sleeve wall defining a sleeve cavity and a proximal sleeve end face; providing an aspirator handle includes a substantially cylindrical sleeve mount and a tubular member, the tubular member extending from the substantially cylindrical sleeve mount; initiating interference between sleeve wall and substantially cylindrical sleeve mount when sleeve mount enters the sleeve cavity; and maintaining interference between sleeve wall and substantially cylindrical sleeve mount from initiation of interference until the aspirator sleeve is installed.

In one embodiment of the method, maintaining interference may also include varying level of interference while maintaining interference over a first portion of an engagement distance along the sleeve mount. In one embodiment of the method, varying level of interference may also include increasing the level of interference in response to a first range of assembly forces over the first portion of engagement distance along the sleeve mount. In one embodiment of the method, varying level of interference may also include increasing level of interference in response to a second range of assembly forces over a second portion of engagement distance along the sleeve mount.

In one embodiment of the method, a first rate of increasing assembly force for the first portion of the engagement distance is greater than a second rate of increasing assembly force for the second portion of the engagement distance. In one embodiment of the method, the first portion of the engagement distance includes a region of the outer surface that initially interferes with substantially cylindrical sleeve mount. In one embodiment of the method, the second portion of the engagement distance includes a region of the outer surface that is bounded proximally by a shoulder of the handle. In one embodiment of the method, the method may also include moving substantially cylindrical sleeve mount into sleeve cavity over an engagement distance until aspirator sleeve is installed on substantially cylindrical sleeve mount, wherein interference occurs over the engagement distance.

In one embodiment of the method, the method may also include selecting sleeve and selecting handle such that when sleeve is installed on substantially cylindrical sleeve mount, a combination of sleeve and handle has appearance of a Poole suction device. In one embodiment of the method, the method may also include in response to installation of sleeve on sleeve mount by a user, providing tactile feedback to the user during installation until the sleeve is fully engaged relative to the sleeve mount.

In one embodiment of the method, the method may also include, in response to installation of sleeve on sleeve mount by a user, providing tactile feedback to the user during installation until the sleeve is fully engaged relative the sleeve mount. In one embodiment of the method, the tactile feedback is an assembly force, wherein the assembly force provided to the user is increasing until the sleeve reaches a shoulder disposed around the sleeve mount. In one embodiment of the method, the interference is a nominal interference of the sleeve wall to a mating diameter of the substantially cylindrical sleeve mount, wherein the nominal interference ranges from about 0.010 inches to about 0.020 inches. In one embodiment of the method, the interference is maintained over an engagement length that ranges from about 0.400 to about 0.800 inches. In one embodiment, the method is a method of assembling a suction device.

In part, the disclosure relates to various suction head features and related embodiments.

In part, the disclosure relates to a suction apparatus, the suction apparatus includes a suction head includes a body, a distal end face and a proximal end face; the body defining a primary opening and a suction head bore, the distal end face surrounding the primary opening, the proximal end face defining an output aperture, the output aperture in fluid communication with the suction head bore and the primary opening; and a plurality of protuberances disposed around the primary opening, each protuberance includes a first region and a second region, the first region cantilevered relative to the distal end face and extending distally relative to the primary opening, the second region extending from body distally from one of the four lobes. In one embodiment, the second region is a ridge, fin, or other shaped structure. In one embodiment of the suction apparatus, the plurality of protuberances is two protuberances. In one embodiment of the suction apparatus, the plurality of protuberances is four protuberances.

In one embodiment of the suction apparatus, the suction head includes four lobes, wherein the plurality of protuberances is two or more protuberances, at least one protuberance extends distally from one of the four lobes. In one embodiment of the suction apparatus, the suction apparatus may also include a tubular member, the tubular member includes a flared distal tip, the flared distal tip disposed in the body in fluid communication with the primary opening and suction head bore, the tubular member extending from the output aperture. In one embodiment of the suction apparatus, the flared distal tip includes a flaring angle, the flaring angle extending from longitudinal axis of tubular member to inner surface of flared distal tip, wherein the flaring angle is greater than about 2 degrees and less than about 40 degrees. In one embodiment of the suction apparatus, one or more of the first regions extending distally relative to the primary opening define one or more flow paths in fluid communication with the output aperture.

In one embodiment of the suction apparatus, the one or more flow paths are also defined relative to a tissue surface, the tissue surface tented, by one or more of the first regions, to form at least a portion of the one or more flow paths. In one embodiment of the suction apparatus, the suction apparatus may also include a handle includes a substantially cylindrical sleeve mount, wherein the tubular member includes a proximal tubular member end face, wherein the proximal tubular member end face is disposed with the handle, wherein the tubular member extends from the substantially cylindrical sleeve mount.

In part, the disclosure relates to a suction apparatus, the suction apparatus includes a housing includes a distal end face and a proximal end face, the housing includes a first shape, a central bore defined by the housing and spanning the proximal end face and the distal end face, the central bore defining a longitudinal axis of the suction head, N vent ports arranged in a first configuration relative to the longitudinal axis, wherein each of the N vent ports is defined by the housing, and M protuberances arranged in a second configuration relative to the longitudinal axis wherein each of the protuberances is defined by the housing, wherein a first portion of one or more of the M protuberances is cantilevered relative to the proximal end face.

In one embodiment of the suction head, one or more of the M protuberances extend from the housing such that upon tissue contact the one or more protuberances at least partially define one or more fluid flow paths. In one embodiment of the suction head, the suction head may also include a handle member and a tubular member defining a tubular bore, the tubular member includes a flared end and a proximal tubular end face, the flared end disposed in the suction head and in fluid communication with the central bore, the handle member attached to the proximal tubular end face.

In one embodiment of the suction head, a flaring angle of the flared end is less than about 40 degrees. In one embodiment of the suction head, the housing, the tubular member, and the handle member are of a unitary construction. In one embodiment of the suction head, one or more of the M protuberances include a second region cantilevered relative to and extending radially from a surface of the housing. In one embodiment of the suction head, the housing includes two or more lobes, wherein one of the M protuberances extend from at least one of the two or more lobes. In one embodiment of the suction head, the second configuration of M protuberances includes a symmetric arrangement of each of the protuberances relative to the longitudinal axis.

In one embodiment of the suction head, M is even, and wherein a channel is disposed between each pair of protuberances, the channel defined by the housing, wherein one or more of the N vent ports is disposed in each channel. In one embodiment of the suction head, the housing includes four lobes arranged around the central bore in a cruciform arrangement, wherein M is 2 and the second configuration includes one of the protuberances extending distally from at least one of the lobes. In one embodiment of the suction head, the M protuberances protrude from the proximal end face of the housing, and wherein the housing defines a plurality of recessed regions at the proximal end face. In one embodiment of the suction head, N is a natural number and M is a natural number less than or equal to eight. In one embodiment of the suction head, the first shape is selected from the group consisting of a bulb, a knob, ellipsoidal, a conic section, a frustum, a sphere, a truncated ellipsoid, a half sphere, and a shape defined by a surface of revolution.

In one embodiment of the suction head, the second end of the housing tapers to a substantially elliptical opening, the substantially elliptical opening defined by the housing and in fluid communication with the central bore. In one embodiment of the suction head, the suction head may also include a tubular member, the tubular member disposed in the housing and extending through the substantially elliptical opening, the tubular member in fluid communication with the central bore and the N vent ports. In one embodiment of the suction head, the suction head may also include a handle includes a substantially cylindrical sleeve mount, a tubular member extending from the handle and having a flared proximal end face, wherein the housing is secured to the proximal end face.

In part, the disclosure relates to a suction apparatus, the suction apparatus includes a body defining a bore, the bore defining a longitudinal axis, the body having a proximal end and a distal end, the bore in fluid communication with a central opening, one or more protuberances arranged around the longitudinal axis, each of the one or more protuberances being an extension of a surface of the body in or more directions, wherein a distal end of each protuberance extends beyond the central opening a distance D; and a plurality of trenches arranged around the longitudinal axis, each of the trenches being a deformation of the surface of the body, wherein the plurality of trenches define a plurality of vent holes. In one embodiment of the suction apparatus, D ranges from about 0.002 inches to about 0.1 inches. In one embodiment of the suction apparatus, the suction head has a cruciform cross-sectional shape defined by the central opening and four surface extensions of the housing, wherein the one or more protuberances is two protuberances or four protuberances.

In one embodiment of the suction apparatus, the body includes a ring-shaped distal end face encircling the bore and the distal end of each protuberance cantilevered relative to the ring-shaped distal end face. In one embodiment of the suction apparatus, the distal end of each protuberance is arranged relative to the central bore such that upon tissue contact the distal end protuberances define one or more fluid flow paths relative to the central bore. In one embodiment of the suction apparatus, the one or more fluid flow paths are also defined by one or more tissue regions.

In part, the disclosure relates to various internal geometric features of a suction handle, associated flow paths and related embodiments.

In one aspect, the disclosure relates to an aspirator that includes: a metal tubular member includes a flared end and a proximal tubular end, the tubular member defining a bore, the proximal tubular end includes an inner diameter and an outer diameter; and an elongate handle includes a distal end face defining an aperture, the metal tubular member extending from the aperture, wherein the proximal tubular end, an elongate section of the bore and the metal tubular member are disposed in the handle, a suction connector extending from the proximal end face, the suction connector and the elongate handle defining a first flow cavity, the elongate handle defining a second flow cavity, the second flow cavity disposed within the handle, the second flow cavity adjacent to and in fluid communication with the first flow cavity, the second flow cavity adjacent to the proximal tubular end and in fluid communication with the bore, wherein the first flow cavity, the second flow cavity and the elongate section of the bore define an inner flow path within the handle.

The aspirator may also include a suction head defining a third flow cavity in fluid communication with the inner flow path, the suction head attached to the flared end. In one embodiment, the suction head and the handle include a polymer material. In one embodiment of the aspirator, the first flow cavity has a truncated cone shape, wherein a diameter of the second flow cavity is less than diameter of the first flow cavity at an interface of the first flow cavity and the second flow cavity. In one embodiment of the aspirator, the distal end face of handle includes a substantially cylindrical sleeve mount.

In one embodiment of the aspirator, a diameter of second flow cavity is greater than the outer diameter. In one embodiment of the aspirator, interface between first flow cavity and second flow cavity includes a stepped transition. In one embodiment of the aspirator, the metal tubular member is a cylindrical tube or a tapered tube. In one embodiment of the aspirator, the flared end has a flared outer diameter, wherein the ratio of the flared outer diameter to the outer diameter of the proximal tubular end is less than about 1.4. In one embodiment of the aspirator, a length of the second flow cavity is less than a length of the first flow cavity. In one embodiment of the aspirator, a length of the elongate section of the bore in the handle is greater than the length of the second flow cavity.

In one embodiment of the aspirator, an inner diameter of the bore is less than or equal to a diameter of the second flow cavity. In one embodiment of the aspirator, a curved transition is defined at a junction of an inner surface of the third flow cavity of the suction head and the flared end. In one embodiment of the aspirator, the curved transition is a radius or smooth curve. In one embodiment of the aspirator, the outer diameter of the tubular member is greater than or equal to a diameter of the second flow cavity. In one embodiment of the aspirator, a diameter of first flow cavity is less than about 0.5 inches, wherein the diameter of the first flow cavity is widest dimension of inner flow path of handle.

In one aspect, the disclosure relates to an aspirator that includes: a metal tubular member includes a flared end and a proximal tubular end, the tubular member defining a bore, the proximal tubular end includes an inner diameter and an outer diameter; a suction head attached to the flared end, the suction head defining a suction head bore, the suction head bore in fluid communication with the bore; and an elongate handle includes a suction connector, and a section of the tubular member disposed within the handle, the handle defining a proximal flow cavity adjacent to and in fluid communication with the suction connector, the handle defining a transitional flow cavity between the section of the tubular member and the proximal flow cavity; the section of the tubular member, the transitional flow cavity and the proximal flow cavity defining an inner flow cavity in fluid communication with the bore of the metal tubular member and the suction head bore, wherein a diameter of transitional flow cavity is less than diameter of proximal flow cavity at interface of transitional flow cavity and proximal flow cavity.

In one embodiment of the aspirator, the flared end has a flared outer diameter, wherein the ratio of the flared outer diameter to the outer diameter of the first end is less than about 1.4. In one embodiment of the aspirator, the diameter of transitional cavity is greater than the outer diameter. In one embodiment of the aspirator, the interface between transitional flow cavity and proximal flow cavity includes a stepped transition. In one embodiment of the aspirator, the tubular member is a cylindrical tube or a tapered tube.

In one embodiment of the aspirator, the proximal flow cavity is a truncated cone. In one embodiment of the aspirator, a curved transition is defined at a junction of an inner surface of the suction head bore and the flared end. In one embodiment of the aspirator, the curved transition is a radius or smooth curve. In one embodiment of the aspirator, the outer diameter of the tubular member is greater than or equal to a diameter of the transitional flow cavity. In one embodiment of the aspirator, the inner diameter of the tubular member is less than a diameter of the transitional flow cavity In part, the disclosure relates to various suction head, sleeve and aspirator clearances, skewing angles constrained thereby and related embodiments.

In one aspect, the disclosure relates to an aspirator that includes: a handle includes a shoulder and a sleeve coupler, the sleeve coupler defining an aperture, the handle and the sleeve coupler includes a longitudinal axis, wherein the sleeve coupler is in relief relative to the shoulder; a tubular member defining a bend, the tubular member includes a proximal tube end and a distal tube end, the proximal tube end disposed in the handle, the tubular member extending from the sleeve coupler and the aperture; and a suction head includes a distal end face, the suction head attached to the tubular member, wherein a clearance is defined between a sleeve inner surface of the elastic sleeve and the suction head.

In one embodiment of the aspirator, the clearance ranges from about 0.080 inches to about 0.11 inches, wherein the clearance is between the distal end face of the suction head and the sleeve inner surface. In one embodiment of the aspirator, the clearance ranges from about 0.001 inches to about 0.020 inches, wherein the clearance is between a side of the suction head and the sleeve inner surface. In one embodiment of the aspirator, the clearance ranges from about 0.005 inches to about 0.100 inches, wherein the clearance is between the distal end face of the suction head and the sleeve inner surface. In one embodiment of the aspirator, a section of the tubular member distal to the bend defines a tubular longitudinal axis, wherein the sleeve coupler is sized to receive an elastic sleeve such that the bend is disposed within the sleeve, wherein a section of the elastic sleeve distal to the bend defines a sleeve longitudinal axis.

In one embodiment of the aspirator, the clearance constrains a first skewing angle range between the longitudinal axis and the sleeve longitudinal axis. In one embodiment of the aspirator, the first skewing angle range is from about 24° to about 32°. In one embodiment of the aspirator, the first skewing angle range is from about 33.5° to about 41.5°. In one embodiment of the aspirator, the first skewing angle range is from about 32° to about 40°. In one embodiment of the aspirator, the clearance constrains a second skewing angle range between a portion of the sleeve and a portion of the tubular member after the bend.

In one embodiment of the aspirator, the second skewing angle range is from about 5° to about 15°. In one embodiment of the aspirator, the second skewing angle range is from about 2° to about 60. In one embodiment of the aspirator, the elastic sleeve defines a plurality of vent holes, a sleeve lumen and the sleeve inner surface, the elastic sleeve includes a sleeve tip and a sleeve rim, wherein the sleeve rim defines a sleeve opening. In one embodiment of the aspirator, a distal end face of the sleeve is next to the shoulder, wherein combination of sleeve and aspirator resembles a Poole suction device. In one embodiment of the aspirator, a surface of the tubular member at the bend contacts the sleeve inner surface at one or more regions.

In one aspect, the disclosure relates to an aspirator that includes: an elastic sleeve includes a proximal sleeve end, a distal sleeve end and an inner sleeve wall, the proximal sleeve end and inner sleeve wall defining an elongate tapered cavity, wherein the elongate tapered cavity defines a handle coupling region, a bend region, a suction head receiving region; and a first clearance region; and a suction head defining a suction head bore, a distal suction head end face and an output aperture; a handle includes a sleeve coupler and a suction connector barb, the handle defining an elongate cavity, the sleeve coupler defining a handle opening, the elongate cavity in fluid communication with the handle opening and the suction connector barb; and a hollow tubular member includes a flared end, a proximal tubular end and a bend disposed between the flared end and the proximal tubular end, the flared end extending from the output aperture, the proximal tubular end extending from the sleeve coupler, wherein a first clearance distance normal to distal suction head end face is present in the first clearance region when sleeve coupler is disposed in the handle coupling region.

In one embodiment of the aspirator, the first clearance ranges from 0.080 inches to about 0.11 inches. In one embodiment of the aspirator, the elongate tapered cavity defines a second clearance region, wherein a second clearance distance normal to surface of tubular member is present in the second clearance region when sleeve coupler is disposed in the handle coupling region. In one embodiment of the aspirator, the second clearance region is disposed between the first clearance region and the bend region. In one embodiment of the aspirator, the second clearance ranges from about 0.001 inches to about 0.020 inches.

In one embodiment of the aspirator, the elastic sleeve has a first longitudinal axis and a portion of the tubular member after the bend has a second longitudinal axis, wherein the skewing angle between the first longitudinal axis and the second longitudinal axis is greater than about 2 degrees and less than about 10 degrees. In one embodiment of the aspirator, the first clearance ranges from about 0.005 inches to about 0.100 inches. In one embodiment of the aspirator, combination of elastic sleeve, suction head, hollow tubular member and sleeve coupler resembles a Poole suction device.

In part, the disclosure relates to a method. The method includes providing an aspirator includes a sleeve mount and a tubular member extending therefrom, the tubular member includes a bend; providing an elastic sleeve defining an opening, an inner sleeve wall and a lumen to receive the sleeve mount and tubular member; and skewing the elastic sleeve relative to a portion of the tubular member distal to the bend by a skewing angle greater than 2 degrees after sleeve mount is installed within the lumen. In one embodiment, a distal end of the tubular member terminates in a suction head includes a distal end face, and may also include maintaining a clearance between the distal end face and the inner sleeve wall. In one embodiment, the clearance is less than or equal to about 0.11 inches. In one embodiment, the method is a method to provide tactile feedback to and end user and ease assembly of sleeve and sleeve mount. In one embodiment, the method is a method of assembling a suction device.

Additional Embodiments and Features

In one embodiment, the aspirators and aspirator components described herein comprise a polymer. In one embodiment, the aspirators and aspirator components described herein comprise a metal. In one embodiment, the aspirators and aspirator components described herein comprise a polymer and a metal. In one embodiment, the sleeves described herein comprise and elastic material. In one embodiment, an aspirator as described herein includes a tubular member or tube such as a cannula. The tubular member can comprise a metal. In one embodiment, an aspirator as described herein includes metal suction head. In one embodiment, an aspirator as described herein includes a polymer suction head. In one embodiment, the aspirators described herein comprise a tubular member that includes a flared end having a flared outer diameter and an inner diameter and an end having a circular cross-section with an outer diameter less than the flared outer diameter. In one embodiment, the tube, the aspirator, and the sleeve are manufactured using one or more polymers.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation. Further, the various aspirators, sleeves, components, and parts of the foregoing can be used for medical applications and other applications for fluid suction and fluid delivery without limitation.

Other features and advantages of the disclosed embodiments will be apparent from the following description and accompanying drawings.

BRIEF DESCRIPTION OF DRAWINGS

The figures depicted and described herein are not necessarily to scale, emphasis instead generally being placed upon illustrative principles. The figures are to be considered illustrative in all aspects and are not intended to limit the invention, the scope of which is defined only by the claims.

FIG. 2A is a side elevational view depicting the aspirator of FIG. 1, in accordance with an illustrative embodiment of the disclosure.

FIG. 2B is a side elevational view depicting the aspirator sleeve of FIG. 1, in accordance with an illustrative embodiment of the disclosure.

FIG. 4 is a multi-cutaway view depicting aspirator handle engagement with an aspirator sleeve, in accordance with an illustrative embodiment of the disclosure.

FIGS. 5A, 5B, 5C and 5D are a series of multi-perspective views depicting a suction head suitable for use with an aspirator and other medical suction devices in accordance with an illustrative embodiment of the disclosure.

FIG. 6A is a cutaway side view depicting a distal end of an aspirator that includes a tubular member and suction head, in accordance with an illustrative embodiment of the disclosure.

FIG. 6B is a perspective view depicting a suction head semi-transparently relative to a tubular member having a flared tip, in accordance with an illustrative embodiment of the disclosure.

FIG. 7A is a front view depicting an aspirator sleeve, in accordance with an illustrative embodiment of the disclosure.

FIG. 7B is a front cutaway view depicting the suction head of the aspirator, configured to engage with the aspirator sleeve of FIG. 7A, in accordance with an illustrative embodiment of the disclosure.

FIG. 7C is a back view depicting an aspirator sleeve and inner matting surface thereof, in accordance with an illustrative embodiment of the disclosure.

FIG. 9A is a perspective view depicting an aspirator, in accordance with an illustrative embodiment of the disclosure.

FIG. 9B is a perspective view depicting a handle of an aspirator and the sleeve coupler or mount portion thereof with a tubular member extending from it, in accordance with an illustrative embodiment of the disclosure.

FIG. 10A is a schematic view of a curve in a plane with a longitudinal axis of rotation in the plane by which a surface or solid of revolution can be generated to define a flow path within a handle or other member, in accordance with an illustrative embodiment of the disclosure.

FIGS. 10B and 10C are cutaway views depicting an elongate member such as a handle that includes a fluid flow path that is suitable for use with various medical devices in accordance with an illustrative embodiment of the disclosure.

FIG. 10D is a side cutaway view depicting a suction head defining a bore attached to a flared tubular member in accordance with an illustrative embodiment of the disclosure.

FIGS. 11A, 11B and 11C are cutaway views depicting engagement of aspirator handle embodiments, two sleeve coupler embodiments, and sleeve deformation for each of the two coupler embodiments, in accordance with an illustrative embodiment of the disclosure.

FIGS. 12A and 12B are side cutaway views showing the engagement of an aspirator sleeve and the interference therewith over an engagement length in accordance with an illustrative embodiment of the disclosure.

DETAILED DESCRIPTION

Figure 1:
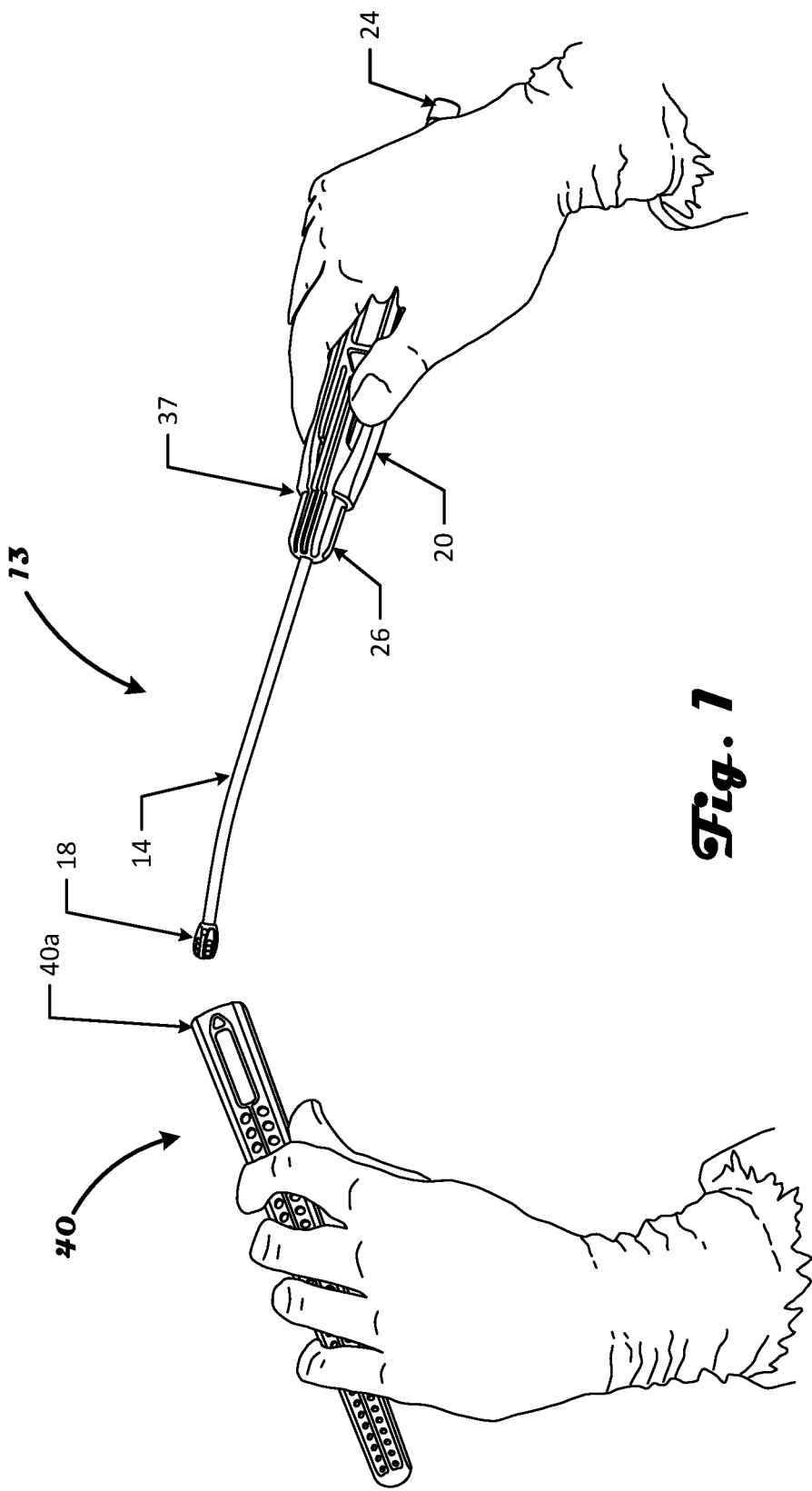
FIG. 1 is a side elevational view depicting an aspirator and an aspirator sleeve suitable for combination, in accordance with an illustrative embodiment of the disclosure.

Embodiments of an aspirator will now be described. The aspirator can be used in combination with or without an elastic sleeve in various embodiments. Although embodiments of the present disclosure will be depicted generally as Yankauer or Andrews aspirators, Poole suction devices, surgical suction catheters and other suction devices and component devices thereof one skilled in the relevant art will appreciate that the disclosed embodiments are illustrative in nature, and therefore, should not be construed as limited in application or its construction and mechanical and geometric properties with either a Yankauer or Andrews-type aspirator, a Poole suction device, other suction devices, other medical devices and variants of the foregoing.

The embodiments of the present disclosure have wide application, and may be used on any similar aspirator and sleeve combination or as an aspirator without a sleeve, such as a Frazier aspirator and sleeve combination and other aspirators, surgical suction catheters, fluid transport devices and components thereof. Some embodiments of aspirators and aspirator sleeve assemblies are suitable for use as disposable handheld suction devices. The suction head described herein can be used in any suitable suction or spraying application. Further, although generally described in the context of surgical procedures and medical devices, in part, the devices and methods described herein also generally relate to fluid transport and suction devices and thus have applications outside of the medical field as such devices can be adapted or configured, whole or in part.

Accordingly, the following descriptions and illustrations herein should be considered illustrative in nature, and not limiting the scope of the invention, as claimed. As used herein, fluid such as in fluid communication refers to flow paths for liquids, gases and other materials entrained therein which can flow through the aspirators described herein.

Introduction to Design Features of Various Embodiments

In part, the disclosure includes features that relate to an aspirator having a suction head that can be used with or without sleeve and various improvements relating to components of the aspirator and the combination of the sleeve with the aspirator. In one embodiment, the sleeve is sized and configured to manually engage a handle member and also secure to the handle and remain secured during use of the handle-sleeve combination. Thus, in part, the disclosure relates to improving the process of fitting a sleeve onto a handle when converting a first handheld suction device into a combination suction device via the installation of a flexible sleeve. In one embodiment, the assembly process of engaging and securing a sleeve and a handheld member converts a first suction device to a Poole suction device or a variation of a Poole suction device.

In one embodiment, installing a sleeve on a handle member is designed to provide tactile feedback to the user and result in a gradually increasing engagement and securement rather than negligible or zero engagement initially followed by an abrupt engagement and securement as the end of the engagement length. The sleeve mating area handle is substantially cylindrical in one embodiment. The method of installation includes fitting a sleeve over a handle surface such as a sleeve coupler or sleeve mount that has a substantially cylindrical shape.

As a result, interference between sleeve and sleeve coupler of handle occurs upon engagement and continues as sleeve moves along engagement length of sleeve coupler. The substantially cylindrical shape is selected to avoid a conical shape and other undesirable sleeve coupler shapes. In general, the undesirable sleeve coupler shapes result in an abrupt force increase during the final steps of the sleeve and handle combination process which is undesirable to an end user.

In one embodiment, the nominal interference of the sleeve to the mating diameter of sleeve coupler ranges from about 0.010 to about 0.020 inches. In one embodiment, the nominal interference of the sleeve to the mating diameter of sleeve coupler ranges from about 0.012 to about 0.040 inches as another embodiment. Prior to engagement of sleeve and sleeve coupler, and the associated interference between the two during assembly, it is worthwhile to consider the engineering of the interference for its tactile feedback and other advantages. In part, such interference is defined by the geometry of both the sleeve and the handle mating areas in their relaxed, never-assembled states. The engagement length, which includes the mating length, for various aspirator designs, such as without limitation, the designs shown and described herein, ranges from about 0.400 to about 0.800 inches. In one embodiment, the elastic sleeve includes an elastic vinyl or other elastic polymer suitable for use in a medical application. In one embodiment, the substantially cylindrical sleeve mount/coupler includes a rigid plastic. Other rigid polymer-based materials and other rigid materials can be used in various embodiments.

In addition, in one embodiment, whether a suction device is used alone or in combination with a sleeve, the suction devices are configured to include improvements while retaining familiar shapes reminiscent of classic suction instrument designs. In one embodiment, when installing an elastic sleeve relative to or on a sleeve coupler of the handle of a suction device, the elastic sleeve conforms to the curvilinear profile of the tubular member and takes on the appearance of a Poole suction device.

The shape, sizes, groove and other features of the elastic sleeve and the handles, tubular members and suction heads and the associated bends and contours or lack thereof for each of the foregoing described and depicted herein can vary such that the appearance and functionality thereof are adapted to a particular application. In addition, the shapes, sizes, grooves and other features of a given sleeve and aspirator can be tailored to replicate those of existing medical devices while incorporating one or more of the various design improvements described herein.

In some configurations a sleeve is not used with an aspirator and the aspirator is used as a medical suction catheter with handle, a cannula or tubular member, and a suction head. An exemplary suction head includes a primary opening and a plurality of protuberances arranged relative thereto. A plurality of vent holes is defined by the suction head and arranged relative to the primary opening in one embodiment. In addition, a plurality of protuberances is arranged relative to the vent holes in a cantilevered configuration relative to the body of the suction head and disposed in a geometric pattern such as a symmetric pattern relative to the primary opening. The suction head embodiments can be used as a component of an aspirator as described herein. In addition, the suction head embodiments can be used with any suitable medical device to provide suction, irrigation, or any other fluid directing functionality.

The suction head includes a body such as a housing or workpiece and can be of various shapes and includes smooth surfaces that define holes, cavities, ridges, or other suction head structures or voids. The suction head can include one or more protrusions to help prevent obstruction of a fluid transport channel or port of the suction head.

In one embodiment, the suction devices described herein include a handle, a tube, a crowned or cruciform suction head, and a sleeve. Each of the respect foregoing components of a suction device can be manufactured using polymers, metals, resins, laminates, printable materials and combinations and variations of the foregoing. In one embodiment, two or more of the foregoing components of a suction device are unitary.

In various depictions of embodiments in the figures, a distal direction D and a proximal direction P are shown with arrows to provide a reference frame. Additional details relating to these exemplary embodiments and various other embodiments are described in more detail herein.

Aspirator, Sleeve and Combination Suction Device Features

Figure 3:
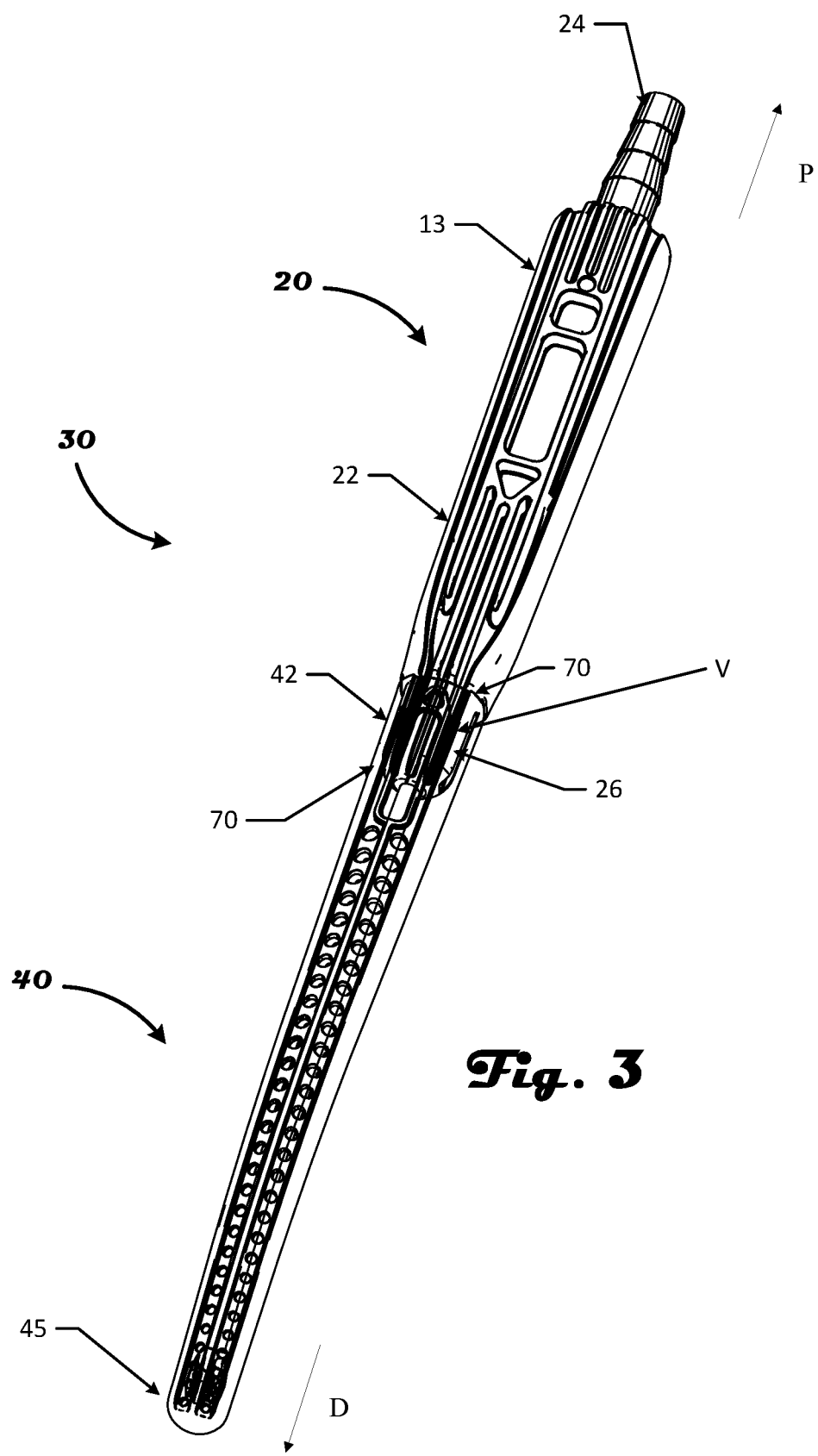
FIG. 3 is a front view depicting an aspirator combined with an aspirator sleeve, in accordance with an illustrative embodiment of the disclosure.

FIGS. 1 and 2A show an aspirator 13. An elastic sleeve 40 suitable for use with the aspirator 13 is shown in FIGS. 1 and 2B. The aspirator 13 can be introduced into a sleeve 40 to form the surgical aspirator and sleeve combination 30 as shown in FIG. 3. The sleeve 40 is flexible and includes an inner surface sized to mate with a sleeve coupler 26, which is a portion of handle 20. The sleeve coupler 26 is the portion of the handle to which the sleeve attaches. The sleeve 40 and sleeve coupler interfere upon the start of engagement when the sleeve facing end face cross the plane of the proximal end face of sleeve 40a.

In one embodiment, the handle is a body that includes a hollow or cavity that spans the length of the handle and is in fluid communication with a proximal handle opening and a distal handle opening. This cavity of the handle is formed from one or more cavities in one embodiment which form a fluid transport path or channel. A tubular member 14 is attached to a suction head 18. The combination of sleeve 40 and aspirator 13 is referred to as a suction set or a combination suction device 30 in one embodiment. The term suction catheter generally refers to an aspirator which can include a sleeve or be sleeveless in various embodiments.

FIG. 2A depicts the surgical aspirator 13. The aspirator 13 generally includes a hollow tubular member 14 that is inserted into a wound, bodily orifice, or surgical site. Still referring to FIGS. 1 and 2A, the aspirator 13 further includes an enlarged hollow medial section, or elongated handle member 20. The handle member 20 includes a grip member 22 for gripping the aspirator 13, a barb or suction tube coupling member 24 that is used to attach the aspirator 13 to a tube that in turn is connected to a source of suction (not shown), a sleeve coupler 26 for attaching a sleeve 40 (see FIG. 1) to the aspirator 13. The sleeve coupler can also be referred to as a sleeve mount or as a male coupling portion of handle.

In one embodiment, the sleeve coupler is configured as a male coupler which is introduced into the lumen of the sleeve at the sleeve opening but other coupling designs are possible. In one embodiment, interference between sleeve and sleeve coupler occurs upon engagement of the sleeve with the substantially cylindrical shape of the sleeve coupler. In one embodiment, the sleeve coupler receives and interferes with the inner surface of the sleeve along an engagement length. Sleeve coupler 26 extends distally from handle 20 and terminates at a sleeve coupler end face. In one embodiment, a shoulder 37 is also a component or portion of the handle 20. The shoulder extends beyond, surrounds the sleeve coupler, and provides a surface for the sleeve to abut when combination with the aspirator is complete.

The handle member 20 and tubular member 14 are constructed from one or more materials. The materials are a rigid or semi-rigid, resiliently deformable material that is adaptable for use in the medical arts. In one embodiment, polymeric or resinous plastic is used. In one embodiment, a metal is used. Suitable metals can include stainless steel, nickel plated brass, steel alloys, brass alloys, nickel allows, and any other metal or combinations or alloys of metal suitable for a given medical use or having desirable mechanical properties. The tubular member 14 can include without limitation a tube, a cannula, a tubular member, a ferrule, and other elongate objects and combinations thereof.

The tubular member includes one or more bends 17 in one embodiment. Any number of combinations of bends 17 can be formed along the length of tubular member 14. The one or more bends 17 can include one or more kinks, elbows, corners, and other bends and directional changes in the tubular member. In one embodiment, the one or more bends are disposed between the handle and the suction head. Each bend 17 can vary over any angle range as is desirable for a given aspirator application. In one embodiment, the bend is absent or slight such that the tubular member 14 is substantially straight.

As shown in FIGS. 1 and 2A, for example, a suction head 18 is disposed at the end of the tubular member 14 in various embodiments. The suction head embodiments described herein such as suction head 18 and other generalized embodiments in which a suction head 180 is shown are not limited to a particular suction device, sleeve, handle or tubular but can be used as part of any fluid transport medical device without limitation.

The sleeve coupler 26 can have a continuous smooth or patterned surface or it can be formed from ridges or plates or subsections such that gaps and grooves are present in its surface. In one embodiment, sleeve alignment grooves 56 may be formed on the sleeve coupler 26. The sleeve alignment grooves 56 are formed in the proximal end of the sleeve coupler 26, and extend a predetermined distance toward the distal end of the sleeve coupler 26. The sleeve alignment grooves 56 are formed on opposite sides of the sleeve coupler 26. The sleeve alignment grooves 56 may have any cross-sectional shape, but preferably have a cross-sectional shape that is generally U-shaped, V-shaped, W-shaped, X-shaped, arcuate or other suitable groove shape without limitation. In some embodiments, no such grooves are present. The outside surface 28 has a cross-sectional profile.

In one embodiment, the cross-sectional profile is substantially cylindrical. This cross-sectional profile extends between the shoulder of the handle and the end face of the sleeve coupler in one embodiment such that the sleeve coupler has a substantially cylindrical shape. In one embodiment, the sleeve and handle are designed such that a portion of the sleeve fits within a portion of the handle. In one embodiment, the sleeve and handle are designed such that the sleeve is secured to the handle by a clasp or another securing device. In one embodiment, the handle includes an annular fence such that the sleeve fits in between the inner and outer fence sections of such a fence or is otherwise attached thereto. Typically, the use of a substantially cylindrical sleeve mount or coupler is preferred for receiving an elastic sleeve.

Referring to FIG. 2B, the sleeve 40 may include grooves or ridges along its external surface as desired to aid in attaching or removing the sleeve 40. In one embodiment, the sleeve includes one or more bearing flats on its interior surface. These flats are configured to align or track with the geometry of the suction head or any disks or other bodies disposed or suspended relative to the tubular member 14. In various embodiments, bearing flats are not used. In one embodiment, the sleeve exterior surface includes ridges 47 and 52 that extend longitudinally along the length of the sleeve 40 on both the upper and lower surfaces of the sleeve 40.

In one embodiment, two center ridges 47 are formed proximally to one another along the center of both the upper and lower surfaces of the sleeve 40, wherein such center ridges 47 are disposed between two lateral ridges 52. In FIG. 7A, a dotted region 80 is shown. This region 80 is an exemplary location where an optional contact feature can be incorporated in the sleeve 40 or where the sleeve itself provides contact. The contact feature, in most cases, is the inside of the sleeve. In various embodiments, region 80 is simply the inner surface of the sleeve. In one embodiment, the regions 80 are where the lobes of the suction touch the inner surface. The region 80 follows the inner, natural contour of the sleeve.

In one embodiment, the sleeve 40 may include additional ribs, ridges, and other projections as well as grooves and depressions on the sleeve exterior surface to lend structural support and aid in conducting gases, fluids, and materials into the interior of the sleeve 40. The sleeve has an inner surface, which can mate, or couple with member 26 at final position 43 as shown in FIG. 4. The sleeve coupler 26 enters the volume or lumen of the sleeve V and thereby interferes with the inner wall of the sleeve.

In this way, the sleeve end face 40a contacts or is in close proximity with shoulder 37 such that engagement stops at final position 43. The sleeve is stopped from advancing further along the member 26 because of shoulder 37 in one embodiment. In some embodiments, such as a sleeve coupler with a conical profile the sleeve can get stuck before reaching the shoulder 37. As a result, a substantially cylindrical profile for sleeve couplers is preferred in various embodiments. The edge of the shoulder 37 completely or partially extends around the border of member 26 in various embodiments. The sleeve coupler 26 is in relief relative to the shoulder 37 of the handle.

In one embodiment, the shoulder effectively operates as a break that terminates movement of a sleeve when being combined with a handle via member 26 that has a substantially cylindrical configuration. In other configurations, such as when member 26 is designed to have a conical configuration, the increasing force resulting from the delayed onset of interference during the sleeve-handle combination process often results in the sleeve becoming stuck along a length of the conical sleeve mount. As a result, for a conical sleeve mount, the shoulder often does not contact the sleeve after combing a sleeve with a handle. In a preferred embodiment, when sleeve is fully engaged on sleeve coupler and contacts the shoulder, this provides tactile feedback to user to indicate that assembly is complete.

As shown in FIG. 2B, the sleeve 40 includes an elongate, nominally straight sleeve tubular body that defines an internal channel having an open, proximal sleeve end face 43 and an enclosed distal sleeve end portion 45. The end face 43 includes or is bounded by a lip or rim of the sleeve 40 in one embodiment. End face 43 of the sleeve includes an annular band or rim, which bounds the inner surface and lumen of the sleeve. The lip of the sleeve abuts the shoulder, which presents further sleeve movement during installation on the aspirator. The sleeve defines a volume or lumen of the sleeve V that facilitates fluid transport and engagement with the sleeve coupler 26 at the inner sleeve wall.

The sleeve 40 also contains a plurality of spaced orifices or vent holes 62 that allow gases, fluids, and materials to flow into the interior of the sleeve 40. The orifices or vent holes are defined by the material(s) of which the sleeve is made. The orifices or vent holes can include holes, channels, cavities and other voids or bores that allow fluids to be suctioned or expelled relative thereto. The orifices 62 are preferably round or ovoid but other shapes may be used. In one embodiment, the orifices are opening, hole, aperture, slot, slit, cleft or channel.

In one embodiment, the orifices or vent holes 62 are sized to permit the inflow of gases, fluids, and materials of a size that will not clog the opening 16 in the tubular member 14 (e.g., a suction head 18) when the tubular member is enclosed by the sleeve 40. Larger materials, on the other hand, such as body tissue, are unable to pass through the orifices 62 and may clog them. The suction head 18 is configured to prevent clogging when used without a sleeve in some embodiments through its various protuberances 17. In one embodiment, the suction head has a bulbous geometry that includes two or more groupings of symmetric features defined by the material used to form the suction head 18.

In one embodiment, the orifices or vent holes 62 are formed between the center ridges 47 and the lateral ridges 52 on each side of the sleeve 40 so that the ridges 47 and 52 may engage the tissue and form a gap between the tissue and the orifices or vent holes 62, thereby preventing clogging. The orifices 62 on one side of sleeve 40 are in alignment with orifices or vent holes 62 on the opposite side of the sleeve.

The sleeve 40 is preferably constructed from a material suitably flexible to conform to the shape of tubular member 14 inserted therein and bend as sleeve 40 engages with coupler 26 of the handle. Suitable materials to construct the sleeve include rigid or semi-rigid, resiliently deformable materials adaptable for use in the medical arts such as polymeric or resinous plastic or other elastic materials. Alternatively, the sleeve 40 may instead be contoured to match the contours present in the tubular member 14.

Referring back to FIG. 2A, the sleeve coupler 26 includes an outside surface 28. The sleeve coupler 26 may be formed in the distal portion of the handle member 20 or attached to the handle member 20 as a separate component. Alternatively, the sleeve coupler 26 may be attached to the tubular member 14 and not attached to the handle member 20. In a one embodiment, the sleeve coupler 26 is between about 20 and about 70 mm long in the longitudinal direction. In one embodiment, the sleeve coupler 26 is substantially cylindrical.

Additional details relating to an exemplary substantially cylindrical coupling member 260 and a non-cylindrical member 265, which is a conical member in this example, are shown in FIGS. 11A and 11B and described in further detail below. The associated deforming effects of such members on a sleeves 1200, 1205 are shown in FIGS. 11A and 11C with regard to sleeve 1205 (engagement with substantially non-cylindrical/conical sleeve mount 265) compared relative to sleeve 1200 (engagement with substantially cylindrical sleeve mount 260). The left side of FIGS. 11A-11C show a combined sleeve and sleeve coupler, a sleeve coupler and a deformed sleeve for a sleeve coupler 260 having a substantially cylindrical profile. The right side of FIGS. 11A-11C show a combined sleeve and sleeve coupler, a sleeve coupler and a deformed sleeve for a sleeve coupler 265 having a conical profile.

In one embodiment, the coupling member 26 has a substantially cylindrical shape and generally has the same cross-section or substantially the same cross-section along its longitudinal axis. Although some slight tapering is permitted. In one embodiment, the degree of tapering of a substantially cylindrical object of the disclosure has an angle of taper of less than about three degrees measured relative to the longitudinal axis of the object. In one embodiment, the angle of taper is less than about 2 degrees measured relative to the longitudinal axis of the object.

In alternate embodiments, the cross-sectional areas of the proximal and distal ends may be approximately equal (e.g., substantially cylindrical configuration). In a preferred embodiment, along its lateral axis, the cross-sectional diameter of the proximal end of the sleeve coupler 26 is between about 4 and about 20 mm and the cross-sectional diameter of the distal end is between about 4 and about 20 mm. The cross-sectional area of the proximal end sleeve coupler 26 is preferably less than the cross-sectional area of the distal end of the grip member 22.

In one embodiment, substantially cylindrical, in the context of interference fit of an elastic sleeve and sleeve coupling member means that the fit (e.g., fit between the handle member 20 and the sleeve 40) mechanically behaves as if the mating surfaces are approximately cylindrical. As used herein, the term "substantially cylindrical" means generally having the shape of a cylinder or a cylindrical shape such that the object resembles a cylinder, but can have one or more deviations from a true cylinder, either with or without a contour, as explained herein.

As reference frame, the cylinder or cylindrical shape of sleeve coupler 26 can include a longitudinal axis. In one embodiment, the deviations from a true cylinder are in the radial direction and can vary along the longitudinal axis. In addition, due to manufacturing constraints, there may be a conical taper to the surfaces that are herein referred to as substantially cylindrical as described herein and may be constrained by angle of taper or a draft angle. In one embodiment, the draft angle for a substantially cylindrical object is greater than zero and less than about 3 degrees. In one embodiment, the angle by which the substantially cylindrical object tapers relative to a longitudinal axis thereof ranges from greater than about 0 degrees to about 3 degrees. In one embodiment, a substantially cylindrical sleeve coupler is a sleeve coupler that avoids the assembly force profile of a conical or substantially conical sleeve coupler as described herein.

The cross-sectional shape of the sleeve coupler 26 may remain constant or vary (as depicted in FIG. 2A) along the longitudinal axis within certain thresholds. In one embodiment, the draft angle of the sleeve coupler is less than or equal to about 4 degrees. The sleeve coupler 26, excluding longitudinal exterior grooves 74 (described below), may have any cross-sectional shape, but preferably has a cross-sectional shape that is substantially cylindrical. The sleeve coupler can have a cross-sectional shape that is generally round, ovoid, square, rectangular, triangular, hexagonal, or other closed shape.

Still referring to FIG. 2A, handle member 20 includes at least one longitudinal exterior groove 74 extending longitudinally along the outside surface of handle member 20. In one embodiment, longitudinal exterior grooves 74 extend from the proximal to the distal end of sleeve coupler 26. It is appreciated that the grooves 74 may extend from the proximal end of the sleeve coupler 26 and along only a portion of the sleeve coupler 26. In addition, the longitudinal exterior grooves 74 extend onto a section of the grip member 22 from its distal end. Alternatively, separate grooves may be included in the grip member 22 that are in communication or intersect with longitudinal exterior grooves 74 on the sleeve coupler 26. Preferably, longitudinal exterior grooves 74 are between about 1 and about 7 mm deep and about 1 and about 10 mm wide, and have any cross-sectional shape such as U-shaped, V-shaped, M-shaped, or other suitable groove shape.

The longitudinal grooves 74 may extend along the entire length of the grip member 22, or, alternatively, may extend along only a portion of the grip member 22. Referring to FIG. 2A, a first set 75 of longitudinal grooves 74 are preferably formed along the top of the grip member 22 and a second set 77 of longitudinal grooves 74 are formed along the bottom of the grip member 22. Each set of longitudinal grooves 75 and 77 is shown having three longitudinal exterior grooves 74, however, fewer or more than three grooves 74 may instead be used. The first set 75 of longitudinal grooves preferably extend along only a portion of the grip member 22, and the second set 77 of longitudinal grooves preferably extend along the entire length of the grip member 22.

As shown in FIG. 2A, the grip member 22 of the handle 20 may also include a lateral groove 76 formed along each side of the grip member 22 lateral to the longitudinal exterior grooves 74. The lateral grooves 76 may extend along the entire length of the grip member 22 or only a portion thereof. The lateral grooves 76 provide traction on the grip member 22 to aid in holding the grip member, especially when attaching or removing the sleeve 40.

Still referring to FIG. 2A, the grip member 22 is suitably sized to be received into an average sized hand but larger or smaller grip sections may be constructed for larger or smaller hands respectively. When being held in a typical manner by a user, the top side of the grip member 22 can be engaged with a user's thumb, and the bottom side of the grip member 22 is can be engaged with the remaining fingers. FIG. 1, for example, illustrates a typical manner of holding the grip member 22 by a user. However, it should be appreciated that the grip member 22 may be held in any comfortable, effective manner.

For instance, the user may instead wrap his entire hand around the grip member 22 such that the user's fingers engage the top side of the grip member 22. Generally, the grip member 22 may be between about 35 and 80 mm long and have a cross-sectional width between about 12 and about 30 mm and a cross-sectional height between about 12 and about 30 mm. The grip member 22 may also be tapered or include contours along its longitudinal axis for a more comfortable grip.

In one embodiment depicted in FIG. 3, the combination of an exemplary embodiment of a sleeve 40 combined with a handle member 20 is shown as combination suction device 30. As shown a substantially cylindrical sleeve coupler 26 of handle 20 is disposed within sleeve 40. In one embodiment the device 30 is designed to resemble a Poole suction device with the bending of the sleeve being reduced such the sleeve is straightened to the extent possible. With regard to the device 30 shown, the installation of the sleeve 40 is achieved by engaging the sleeve's inner surface with a substantially cylindrical mating region of the handle member.

In further detail, the distal end of the grip member 22 abuts the proximal end of the sleeve coupler 42 of the sleeve 40. Longitudinal exterior grooves extend onto grip member 22 from the distal end. Air flows through the portion of longitudinal exterior grooves located in handle member 22 into venting channels. This configuration may prevent air flow interference by either the hand of the user or the distal end of the grip member 22; air can freely flow through the venting channels.

With the sleeve 40 in place, the distal end of the aspirator 13 and sleeve 40 combination device 30 may be inserted into the wound, surgical site, or bodily orifice to remove fluids therein. Suction flows from the suction source, such as a suction pump, through a tube and into the handle member 20 (as shown in FIG. 1). The suction head (not shown) provides suction within the sleeve 40 which pulls liquid in through the various orifices of the sleeve. As shown in FIG. 2A, the barb or suction tube coupling member 24 may include a tiered section that is coupled to the tube and associated suction source by inserting one or more of the tiers having a smaller cross-sectional area into the tube. Generally, any tube coupling mechanism may be used. The tube may be constructed from any tubular material suitable for transmitting suction forces to a surgical aspirator and gases, fluids and materials from a surgical site known in the medical arts.

Handle member 20 defines one or more bores therein (not shown in FIG. 3). In one embodiment, the bores are in stacked arrangement of segments of varying lengths and diameters to define a fluid flow path or channel. The cavity within the handle 20 can be defined as a surface of rotation as described in more detail below. For example, the curve 175a in FIG. 10A can be rotated relative to a longitudinal axis Las such that the fluid flow path or cavity 175b of FIG. 10B is defined. In one embodiment, the arrangement of segments resembles the adjacent sections of a telescope with the diameter of the smaller segment being sized to fit within the larger diameter of the adjoining section. These bore segments or elongate cavities are in fluid communication with suction tube coupling member 24 and suction head 18 in various embodiments. Additional details relating to this arrangement of elongate cavity sections to form fluid transport channels are discussed with regard to FIGS. 10A, 10B and 10C.

In addition, further details relating to the suction head and these elongate cavity sections including the interface of the suction head bore 110d, flared tube end, bore segment disposed in handle, suction connector bore, and a transitional flow cavity in between the suction connector bore and the tube bore, and suction head housing is shown in FIGS. 10B, 10C and 10D. FIG. 10D is a side cutaway view depicting a suction head defining a bore attached to a flared tubular member in accordance with an illustrative embodiment of the disclosure.

Suction traverses the handle member 20 and into the tubular member 14. In various embodiments, the suction traverses the stepped or tiered arrangement of cavities in handle 20. Suction travels up the tubular member and pulls gases, fluids, and small materials into the opening 16. The gases, fluids, and materials inside the sleeve 40 flow from the wound, surgical site, or bodily orifice into the sleeve 40 through the plurality of orifices 62 and opening 16. If the orifices 62 become clogged, such that the flow of gases, fluids, and materials into the interior of the sleeve 40 is at least partially restricted, air flow is available to the sleeve through the venting channels. Air provided by the venting channels may prevent uneven distribution of suction forces over any unclogged orifices 62. Otherwise, if the suction force is concentrated over too few orifices 62, the tissue surrounding the wound could be pulled into the orifices 62 in the sleeve 40 causing discomfort, pain, and injury to the patient.

Engagement Between Surgical Aspirator Handle and Sleeve

Referring now to FIGS. 3 and 4, the sleeve 40 slides over the tubular member 14 of the aspirator 13 so that the tubular member 14 is encased by the sleeve 40. Generally, the sleeve 40 is attached to the aspirator 13 at the handle member 20 by a coupling device. The coupling device includes a sleeve coupling member such as the sleeve coupler 26, shown in FIGS. 2A, 4 and 11A and 11B, and a sleeve coupling member such as the sleeve coupler. The sleeve coupler 26 is received into the proximal end face of the sleeve, which has an inner lumen or receiving volume V to receive the suction head and tubular next member.

As shown in FIG. 3, a coupled region 70 is formed where the sleeve coupler 26 is inserted into the sleeve coupler 26 and span an engagement length EL along the coupler 26. In one embodiment, the sleeve 40 and the sleeve coupler 26 of the handle are designed such that interference commences as soon as the outer surface of the sleeve coupler 26 enters the cavity of the sleeve 40 or otherwise is aligned with and initially contacts the inner wall or rim of the sleeve 40. As depicted in FIG. 4, the sleeve 40 is attached to the handle member 20 at the proximal sleeve end face 43 of the sleeve 40. Likewise, the sleeve 40 may include a plurality of orifices 62.

Figure 13:
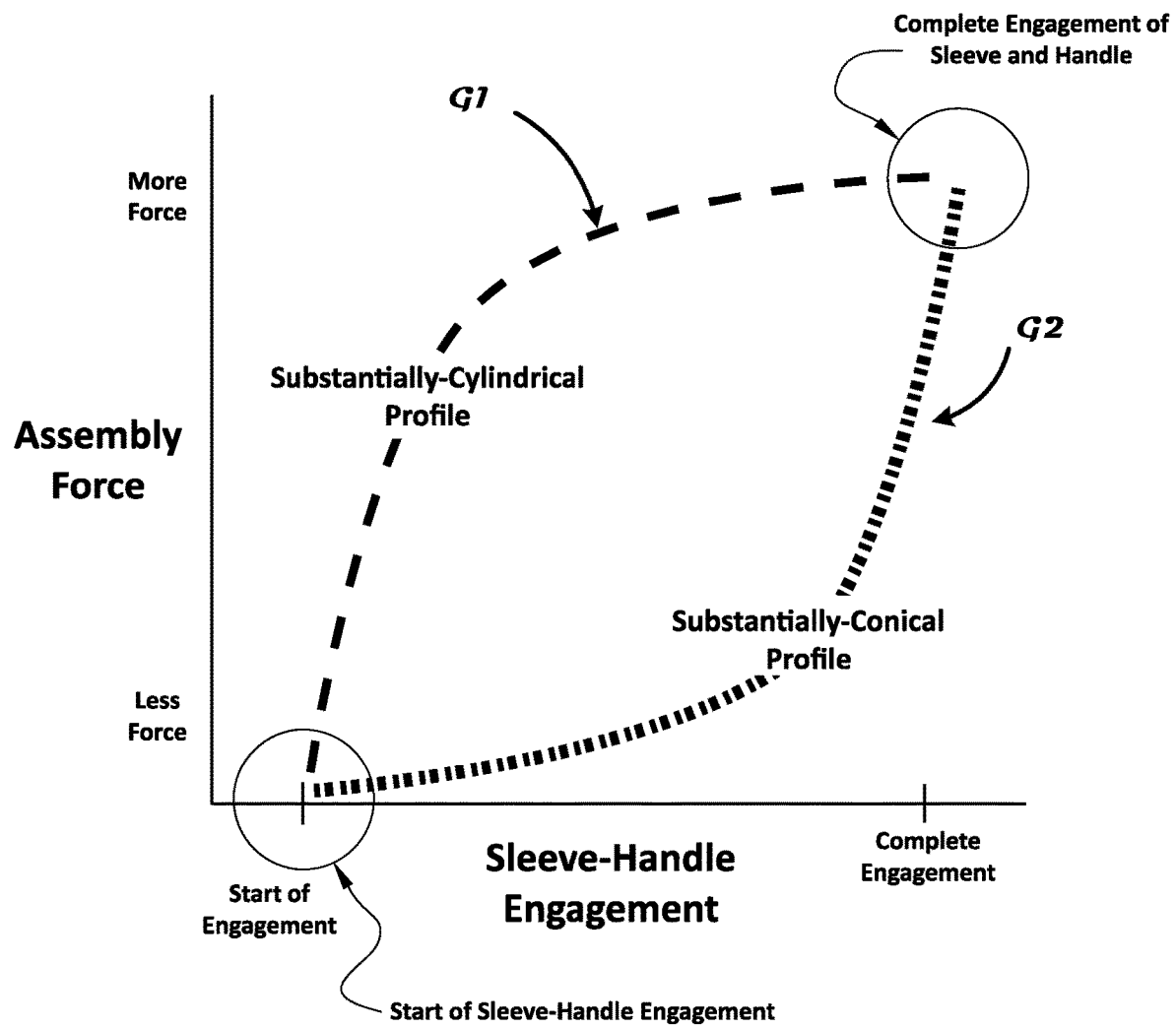
FIG. 13 is a graph depicting an overview of certain generalized force-engagement trends to provide context for certain design features relating to an installation or combination of a sleeve with an aspirator, in accordance with an illustrative embodiment of the disclosure.

In one embodiment, members 26 and 40 couple or engage together such that the elastic sleeve grips and expands to a substantially cylindrical coupler 26 as the sleeve 40 and sleeve coupler 26 of the handle interfere over an engagement length of the coupler. These features are shown in FIG. 3, on the left side of FIGS. 11A-11C, respectively and in FIGS. 12A and 12B. This process of installing the sleeve relative to the handle's coupling or mounting member provides tactile feedback to an end user without abrupt changes in the installation force profile as shown in FIG. 13. This has the advantage of allowing an end user to securely couple the sleeve and the aspirator as they move relative to each other over a distance. This overcomes certain disadvantages with a conical profile.

In general, a conical profile is an example of a non-cylindrical profile. A conical profile of a sleeve mating or couple member 26 can be used in some embodiments, but this design has various design limitations that can be overcome using a substantially cylindrical profile. These can be seen on the embodiments on the rights side of FIGS. 11A-11C for coupler 265. Specifically, with a non-substantially cylindrical coupler, an abrupt spike or increase in the force needed to secure a sleeve to a conical member occurs during engagement and is jarring to the touch. Further, the force needed to achieve the majority of the friction fitting over the remaining short coupling distance consistent with coupling a sleeve to a conical member, may exceed the hand strength of various end users.

In contrast, as disclosed herein pairing of an elastic sleeve with a substantially cylindrical coupling member of an aspirator requires less hand strength to complete the friction fit of the sleeve onto the handle and the tactile experience during the combination is gradual and less jarring than in the case of a conical member to sleeve coupling. As a result, substantially cylindrically shaped sleeve couplers, such as couplers 26, 260 are preferred in one embodiment. As a related point with regard to the assembly of the elastic sleeve relative to the handle over the sleeve coupler, there is hysteresis in the sleeve. Although the sleeve is not being plastically deformed during assembly, the interference with the sleeve mount over an engagement distance can change the shape of the sleeve. Accordingly, after assembly and removal, the sleeve does not necessarily return to its as-molded state.

As shown in FIGS. 5A-5D, an enlarged suction head 180, open at its distal end, is formed on the distal end of the tubular member 14. The suction head 18 includes a body or housing 27. The suction head 180 defines a distal opening or orifice 16 into which gases, fluids, and materials can flow. The suction head has a protective role in various embodiments and generally includes smooth surfaces to avoid cutting or otherwise damaging tissue. In general, smooth or non-sharp surfaces and surface contours and transitions are used in a given aspirator and sleeve design.

The suction head 180 includes one or more flow maintaining features to avoid tissue damage under various suction scenarios by pushing tissue out of the way to maintain flow to opening 16 or other vent holes in the suction head 180. In one embodiment, the housing is made from a polymer, metal, glass, or other material. The housing is formed by injection molding in one embodiment. The body of the suction head is unitary in one embodiment. Other manufacturing processes can be used in various embodiments. In one embodiment, tubular member includes a flared end that the suction head surrounds. This can be achieved via a printing or molding process or a dip and ablate process in one embodiment.

In one embodiment, the housing tapers to a substantially elliptical end opening 16, the substantially elliptical opening defined by the housing and in fluid communication with the central bore. The substantially elliptical end opening can be a circle or substantially circular in one embodiment. With regard to the various embodiments disclosed herein, a taper can be a curvilinear taper, a straight taper, or combinations of differing taper configurations. In one embodiment, the suction head has a shape corresponding to the revolution of a curve about a longitudinal axis as shown in FIG. 10A and described herein. In one embodiment, the suction head has a shape such as for example a cross-sectional shape that includes one or more of the following shapes: a tear, a pear, an elliptical shape, a spherical shape, a hemispherical shape, a conical shape, others shape that lacks sharp edges, an organic shape similar to the forgoing and combinations of the foregoing and subsets thereof.

In one embodiment, the suction head 180 includes protuberances 17 that are disposed on, extend from, or otherwise part of the suction head 180. The protuberances are arranged relative to an end face of the suction head such as a rim or annular band that surround opening 16. Various types of protuberances 17 can be incorporated into the suction head to maintain one or more fluid flow paths even in the event of tissue or other material blocking other flow paths into opening 16. In one embodiment, the suction head includes a plurality or protuberances that are cantilevered from the forward face of the suction head. This forward face is also referred to herein as a distal end face and includes the rim or lip of the central opening 16. In one embodiment, each protuberance can include various surfaces, regions, or ends. In one embodiment, the distal end of each protuberance extends beyond the central opening a distance D. D ranges from about 0.002 inches to about 0.1 inches in one embodiment.

In one embodiment, the protuberances 17 form suction head grooves 21 there between. The suction head 180 is preferably formed with two or four suction protuberances 17 such as ridges that are generally the same size and shape and equidistant from one another, each ridge 17 being diametrically opposite another ridge 17. The suction head ridges are used to abut the sleeve 40 to form a gap between the suction head 180 and the sleeve 40. However, if the aspirator 13 is used without the sleeve 40, the suction head protuberances 17 are capable of bridging the adjacent soft tissue and maintaining the channels in the grooves 21 open for the flow of fluid, gas, and materials through the channels.

The suction head 180 may include additional vent ports or apertures 19. The suction head apertures 19 are formed in suction head grooves 21, and each suction head aperture 19 extends laterally through the suction head from a first suction head groove 21 to an adjacent suction head groove 21. FIGS. 5A-5C illustrate three rows of suction head apertures 19a-19c formed between adjacent suction head grooves 21a and 21c. Each row of suction head apertures 19a-19c is positioned approximately parallel to the other rows. In one embodiment, the suction head apertures have a central channel that passes all the way through the housing. The central axis of this channel is approximately perpendicular to the longitudinal axis of the suction head that passes through opening 16. The suction head apertures 19 intersect the suction head opening 16, such that the suction head apertures 19 are in communication with the suction head opening 16. In FIG. 5C, two protuberances are shown. In other embodiments, three or more protuberances can be used.

In this manner, gases, fluids, and materials may flow within the grooves 21, through the suction head orifices 19, and into the opening 16 in the distal end of the tubular member 14. Although three rows of orifices are shown, it is to be understood that other numbers of rows of orifices 19, either fewer or greater in number, can be utilized. Also, the orifices are shown as round in cross-section, but the orifices can be of other cross-sectional shapes, such as oval, hexagonal, octagonal, etc.

Figure 17A:
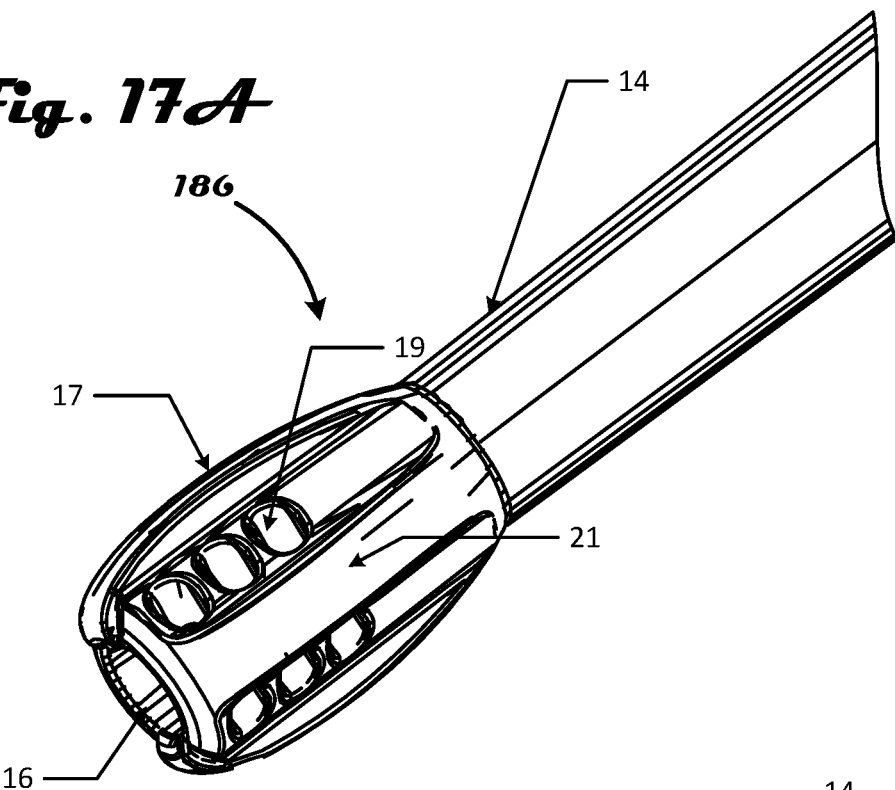
FIGS. 17A and 17B are perspective views of two alternative suction head embodiments suitable for use with an aspirator and other medical suction devices in accordance with an illustrative embodiment of the disclosure.
Figure 17B:
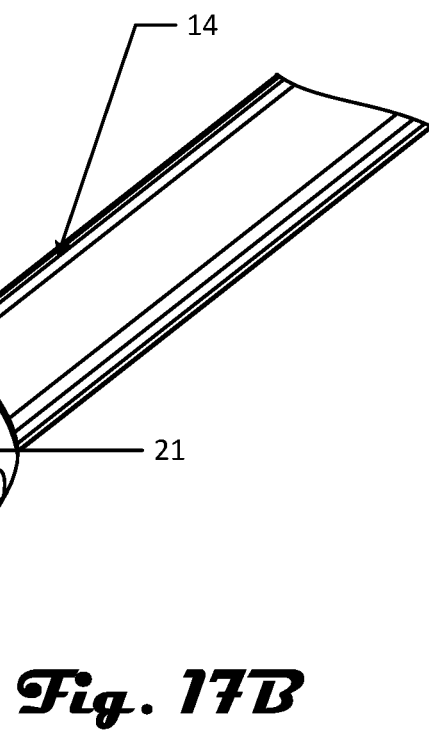

FIGS. 17A and 17B are perspective views of two alternative suction head embodiments 186, 188. These suction head embodiments 186, 188 are suitable for use with an aspirator and other medical suction devices in accordance with an illustrative embodiment of the disclosure. Each suction head 186, 188 is attached to a tubular member 14 which can include one or more bends. In one embodiment, suction head 186 is formed using plastic or other materials as described herein. In one embodiment, suction head 188 is formed by insert molding. The suction heads 186, 188 include bores that terminate at a primary opening 16. Each suction head also includes one or more surface features such as the protuberances 17 shown. The protuberances 17 are cantilevered relative to the opening and radially extend around the bore. A protuberance can range from about 0.002 inches to about 0.1 inches. In another embodiment, a protuberance can range from about 0.001 inches to about 0.2 inches.

The suction heads 186, 188 include a body, which can be formed from plastic or other materials. The body of each suction head defines various orifices 19. In one embodiment, the orifices 19 are formed in suction head grooves 21. In one embodiment, each suction head orifices 19 extends laterally through the suction head portion from a first suction head groove 21 to an adjacent suction head groove 21. The open 16 is surrounded by a distal end face which can be various shapes such as a ring or annular region or an irregular or rectilinear shape. Various suction heads can be used with the aspirators described herein and vary in size and individual dimensions based on the particular suction device design and application thereof. The suction heads 186, 188 are provided as further exemplary embodiments.

Fluid Transport and Suction Promoting Tip Embodiments

As noted herein, various embodiments of suction devices improve the performance of suction when the surgical aspirator 13 (particularly the suction head 18, 180) is used alone (e.g., without the sleeve 40, 1200). In addition, the various types of suction heads described herein can be used with different aspirator and other fluid flow directing devices without limitation. In FIG. 6A, as a general embodiment, a bulbous suction head 190 is showed with a tubular member 140 partially surrounded by the suction head 190. Additional details of various thickness associated with the flow path of the handle 200 that are in fluid communication with tubular member 140 are shown in FIGS. 10B and 10C. Still referring to FIG. 6A, the outer diameter OD of the tubular member 140 is also depicted herewith.

The inner diameter of the bore of tubular member 140 is shown by thickness T3. In general, the thickness of the tubular member bore T3 is the smallest diameter thickness relative to the thickness of the suction head bore T4, and the thickness of the transitional cavity T2 and the thickness T1 of the proximal cavity. The transitional cavity and the proximal cavity can generally be referred to as first and second fluid flow cavities (and vice versa) in one embodiment. The flared lip or edge 102 of the terminus of the tubular member is shown relative to a dotted longitudinal axis.

In one embodiment, the inner flared edge of 102 of member 140 is flared by an angle F relative to the longitudinal axis of the tubular member. In one embodiment, flaring angle F ranges from greater than or equal to 0 to about 36 degrees in one embodiment. In one embodiment, the flaring angle F ranges from about 10 degrees to about 45 degrees. In one embodiment, the flaring angle F ranges from about 25 degrees to about 38 degrees. In one embodiment, the flaring angle F ranges from about 30 degrees to about 37 degrees. The flaring angle F is selected to provide an attachment site at the end of tubular member for plastic or other materials to form around as part of a molding process. In one embodiment, this process is used to attach a metal tubular member having a flared end to a suction head such that the suction head surrounds the flared end and is mechanically fastened thereto. This can be seen in the partially transparent view of FIG. 6B in which suction head 180 has flared end of tubular member 140 with flaring angle F disposed therein.

In addition as shown in FIG. 6A, the bore of the suction head 193 has a thickness T4. The bore of the suction head 193 terminates at opening 16. The thickness of the bore 193 is greater than the tube thickness 140. The bore 193 can be defined as a surface of revolution or a revolute and have various shapes and configurations. The bore 193 is in fluid communication with the elongate fluid flow path of the handle of the aspirator. With regard to FIGS. 10A and 10B, the bore 193 is in fluid communication with elongates sections 110a, 110b, and 110c. The elongate section 110c defined by the handle is a proximal cavity or fluid flow cavity 110a. This cavity can include the bore of the suction connector 250 bore in one embodiment.

In one embodiment, elongate cavity 110c is defined by the inner surface of the tubular member 140 and is the bore of that member 140. This tubular member bore or fluid flow cavity extends through the tubular member 140 until it undergoes a transition when it interfaces with flared region 122 of the tubular member as shown in FIG. 10D. The flared region 122 is part of the suction head, which also includes a fluid flow cavity in the form of the suction head bore 110d. The thickness T4 of the suction head bore 193 is selected to be greater than the thickness of tubular member 140. In one embodiment, with respect to the zone or region at which the flared tubular member expands into the suction head 190, a radius can be defined relative to the bore 193 and the flared lip 102 of the tubular member 140.

In one embodiment, the disclosure relates to a suction head that includes an opening and a plurality of vent holes arranged relative thereto. In one embodiment, the opening is a central or primary opening 16. Such an opening is positioned relative to a distal end face and is the widest opening, port or aperture in the suction head. The central or primary opening is in fluid communication with a distal end face and is at least partially defined by a lip or rim. The distal end face can include an annular region of the suction head that bounds the primary opening of the suction head. The suction head can include various protuberances 17, as shown in FIGS. 6B and 7B for example. The protuberances 17 can be aligned to orient with the vent holes, ridges 47 and 52 and other components of the sleeve. The protuberances 17 are cantilevered relative to one or more features of the suction head 28 in one embodiment. The plurality of protuberances are disposed radially around the primary opening in one embodiment. The plurality of protuberances is 2 in one embodiment. The plurality of protuberances is 4 in one embodiment. The plurality of protuberances is one or more in one embodiment. The suction head body can include one or more lobes.

In one embodiment, one or more of the lobes is aligned with or terminates at a protuberance. Two protuberances aligned with two lobes of a suction head can be seen in the embodiment of FIG. 5C. In one embodiment, the suction head includes two or four second-region protuberances and two or more lobes. In one embodiment, the top and bottom lobes have first region protuberances. The first region protuberances are cantilevered relative to the primary opening in one embodiment. The second region protuberances extend outward from suction head such as ribs or fins in one embodiment.

In one embodiment, a pair of protuberances are aligned along a diameter of the bore of the suction head. In one embodiment, a pair of lobes of suction head is aligned along a diameter of the bore of the suction head. In one embodiment, a first pair of lobes is aligned along a first diameter of the bore of the suction head. In one embodiment, a second pair of lobes is aligned along a second diameter of the bore of the suction head. The first and second diameters can be arranged at an angle such as a 90 degree, 45 degree or another angle. In one embodiment, the first and second diameters are orthogonal such that the lobes form a cruciform configuration. In one embodiment, the suction head includes four lobes and has a cross shape, which each lobe corresponding to an arm of a cross.

In one embodiment, the suction head has a crowned feature formed from a plurality of protuberances, for example, as illustrated by the exemplary suction head embodiments in FIGS. 5A-5D, 6A and 6B. Specifically, the crowned suction head includes protuberances or protrusions 17 that prevent the primary suction hole from being closed off by debris and tissues during use. The suction head 18 is bulbous and in communication with a tubular member such as tubular member 14. FIG. 6B shows a suction head 180 with the addition of a tubular member 140. As shown, the flared portion of tubular member is potted in the suction head to form a mechanical strong attachment. In one embodiment, the suction head 180 is a bulbous housing or workpiece having one or more protuberances such as the crown or cruciform embodiments described herein.

A protuberance 17 is shown on the top of suction 180 in a cantilevered configuration relative to opening 16. As shown, the protuberance 17 extends outward at end 177 past the end face 83 of the suction head 180. This extension of the protuberance 17 relative to end face 83 helps create a flow channel relative to opening 16 and tissue as described with regard to FIG. 8B. Effectively, a protuberance acts like a tent pole that raises the tissue surface in contact with the suction head during a procedure. In this way, the portion of the protuberance in contact with the tissue defines at least a portion of a flow path. Absent the protuberances, the suction head would apply suction to the tissue surface and adhere to the tissue when suction is applied via the barb.

Figure 6C:
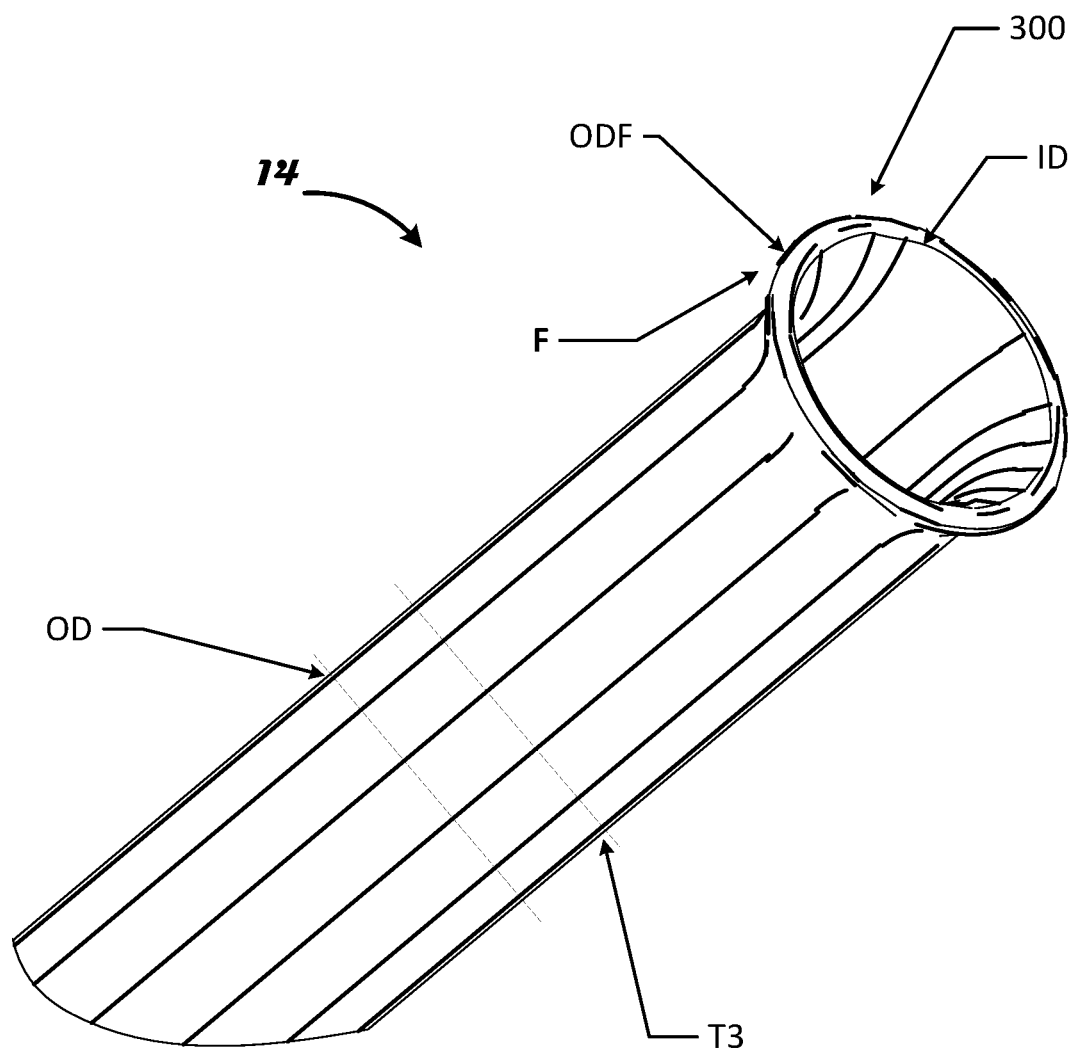
FIG. 6C is a side elevational view depicting a tubular member having a flared tip suitable for use with a suction head, in accordance with an illustrative embodiment of the disclosure.

FIG. 6C illustrates a side elevational view of an exemplary tubular member 14. The tubular member can include various bends and curves (not shown) in an embodiment. In the embodiment illustrated in FIG. 6C, the tubular member 14 has a flared profile. The flaring angle F is shown. The inner and outer thicknesses of the unflared portion of the member 14 are T3 and OD as shown. The flared end face 300 has an outer diameter ODF and an inner diameter IDF.

The ratio of the outer diameter of flared end of tubular member (ODF) to the outer diameter of the tubular member OD is less than or equal to about 1.4. This ratio can also be represented as a fraction as ODF/OD. This ratio has been determined to be an advantageous design constraint for various embodiments. The flared end face 300 helps lock or fasten the suction head 18 (not shown in FIG. 6C) to the tubular member 14. In one embodiment, the suction head is molded around end face 300.

For example, the suction head 18 may include suction head orifices 19. The suction head orifices 19 are formed in suction head grooves 21, and each suction head orifices 19 extends laterally through the suction head portion from a first suction head groove 21 to an adjacent suction head groove 21. The suction head protrusions 17 provide adequate spacing between the suction head orifices 19 on the suction head groove 21 and the surface of the sleeve 40.

Referring to FIG. 6C, sleeve 40 may include sleeve alignment ribs 50 formed along a portion of the interior surface 41 of the sleeve 40 in the space between the orifices 62. The cross-section of fluid transport channel or bore is disposed centrally in FIG. 6C. In region 60, fluids or gases are flowing during operation of a combined sleeve and suction set. The sleeve alignment ribs 50 extend from the proximal end of the sleeve 43 toward the distal tip sleeve end portion 45. Preferably, two sleeve alignment ribs 50 are formed on the interior surface of the sleeve 41 on opposite sides of the sleeve 40. The sleeve alignment ribs 50 taper in height as the ribs 50 extend toward the distal tip sleeve end portion 45.

In one embodiment, the sleeve alignment ribs 50 conform or partially conform to the shape of the sleeve alignment grooves 56, such that the sleeve alignment grooves 56 may engage with and receive the sleeve alignment ribs 50 when the sleeve 40 receives the aspirator 13, as shown in FIG. 3. The sleeve alignment ribs 50 are tapered at the proximal end of the sleeve to form lead-in portions. The lead-in portions aid in securing the sleeve 40 to the aspirator 13 by guiding the sleeve alignment ribs 50 into the sleeve alignment grooves 56.

The sleeve alignment ribs 50 engage and move relative to the sleeve alignment grooves 56 so that the sleeve 40 is properly aligned and coupled to the aspirator 13. In one embodiment, the sleeve alignment grooves orient the sleeve relative to the handle and metal tube and the suction head at the end of the tube. The orientation of the suction head and ridges 17 are set with regard to the handle and thus can be oriented relative to the alignment grooves in the handle. When mated or coupled, in one embodiment, the suction head projections align with the four suction head protuberances or ridges 17 to form a gap between the suction head 18 and the sleeve 40.

As discussed with regard to various embodiments, the sleeve 40 and the sleeve coupler 26 of the handle of a given aspirator embodiment are sized in a plurality of dimensions to cause interference when combined together. Several zones or regions of interference 65 are shown in the figure. They are distributed circumferentially around the inner sleeve wall surface and the surface of the sleeve mount in one embodiment. As shown, the sleeve coupler 26 has a surface that has a substantially cylindrical profile but the surface is not continuous as a result of the grooves or ridges used to form its structure.

Figure 6D:
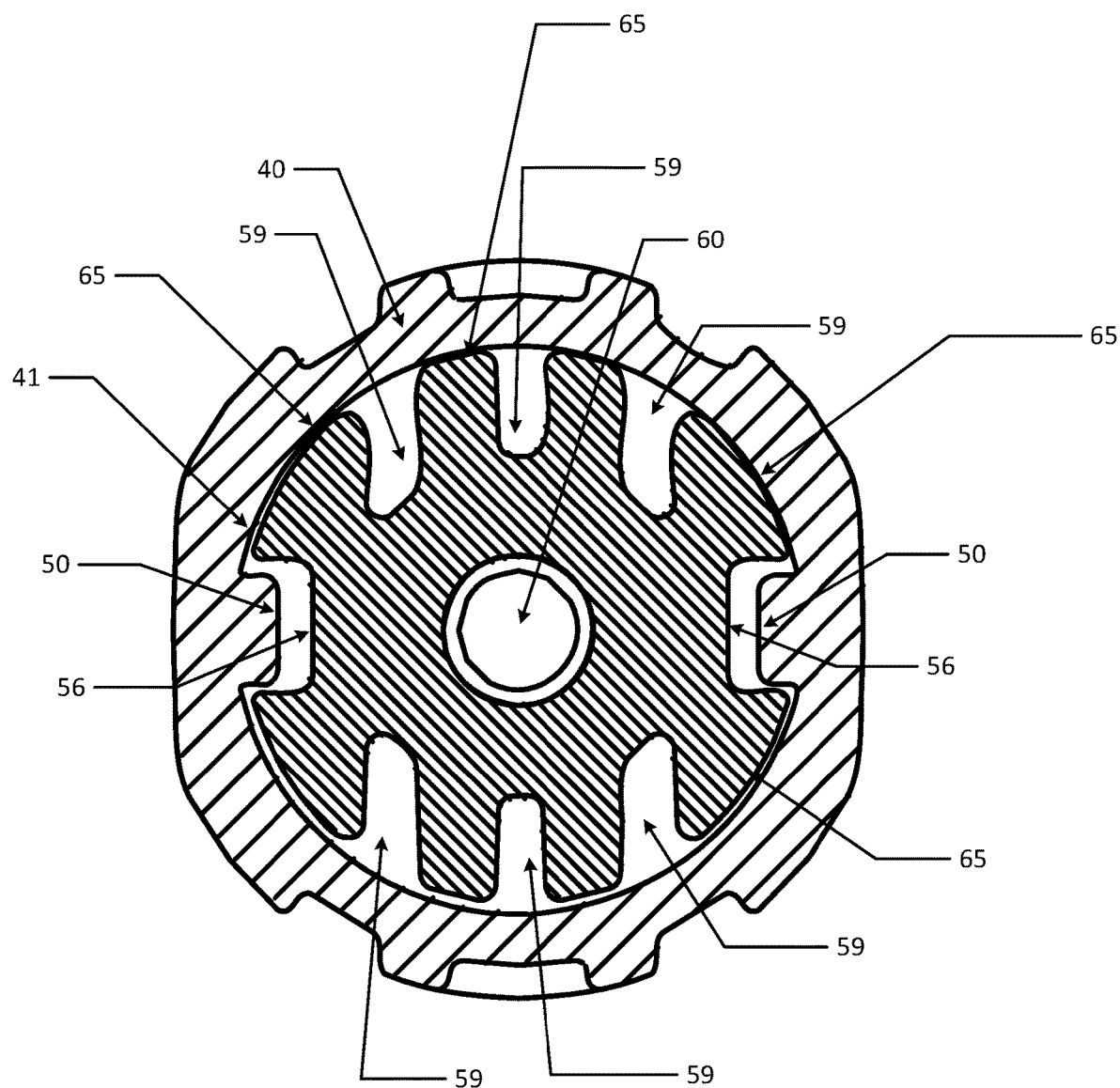
FIG. 6D is a cross-section view depicting an aspirator engaging an aspirator sleeve, in accordance with an illustrative embodiment of the disclosure.

FIGS. 6D and 7A-7B depict sleeve 40 engagement with the suction head 18 of the sleeve 40. Additionally, cross-holes remain properly aligned with longitudinal exterior grooves to ensure proper venting and air flow into the sleeve 40. Moreover, when the sleeve alignment ribs 50 are received by and interfere with the sleeve alignment grooves 56, the sleeve 40 is locked into place and will not rotate about aspirator 13. Thus, while the aspirator 13 is being used, the bearing flats will remain abutted to the four suction protuberances 17, and the cross-holes will remain properly aligned with longitudinal exterior grooves. In FIG. 6D, alignment grooves 56 are sized with an engineered clearance relative to the alignment ribs or tongues 50 such that the two components can align and mate without interfering.

To further aid in proper alignment, indicator designs or indicia may be formed on the sleeve 40 and handle member 20, respectively. Preferably, the indicator designs comprise an arrow or other suitable design or indicia. For example, the indicator design may be in alignment with the center ridges of the sleeve 40 and be in the form of an arrow, with the arrow pointing toward the proximal end of the sleeve 40. Likewise, for example, the indicator design may be formed on both sides of the sleeve 40. A similar indicator design may be formed on the top of the grip member 22, in alignment with the first set of longitudinal exterior grooves, with the arrow pointing toward the sleeve coupler 26.

Either of the two arrows on the sleeve 40 may be aligned with the arrow on the grip member 22 when inserting the aspirator 13 into the sleeve 40, such that the sleeve may be rotated 180° and still properly mate with the aspirator. The indicator designs may facilitate proper alignment of the sleeve alignment ribs 50 with the sleeve alignment grooves 56, thereby ensuring that the suction head projections align and/or abut the four suction head ridges 17.

It should be appreciated that any suitable design or indicia may be used to guide the insertion of the aspirator 13 into the sleeve 40. The indicator design is formed in alignment with the first set 75 of longitudinal grooves 74 on the top of the grip member 22 such that the first set 75 of longitudinal grooves extends only partially along the grip member 22 from the distal end of the grip member 22. It should be appreciated that the indicator design may instead be formed within the first set of longitudinal grooves 75 such that the continuity of the longitudinal grooves 75 is not interrupted, and the grooves 75 instead extend along the entire length of the grip member 22 or a portion thereof.

FIG. 7C is a back view depicting a surgical aspirator sleeve 40 of FIG. 7A, an exemplary sleeve alignment rib 50, and an inner matting surface thereof 85. As described herein with regard to other embodiments, when the handle member engages the sleeve such that the groove on the handle member aligns with groove 50, the contacting points C1, C2 of the suction head shown in FIG. 7B are disposed within the lumen of the sleeve 40 or make contact with the inner sleeve wall or a feature extended therefrom. In one embodiment, mating flats or another projection of the inner sleeve surface can be present at region 80. Thus, alignment at the handle with respect to the sleeve facilitates suction head alignment. In turn, this offers advantages in terms of facilitating the aspirator and metal tube being positioned in the sleeve 40 at a predetermined position or with a predetermine clearance.

In one embodiment, as shown in FIG. 7B, the suction head 180 includes a body with various protuberances 17. In one embodiment, the body includes a bore which provides a fluid transport function. The body is bulbous fluid flow directing member in one embodiment. The body can be of various shapes without limitation. Further, as shown the suction head includes an annular or ring-shaped distal end face 83 encircling or surrounding the primary suction head opening or bore 16. To provide greater stability, in one embodiment, one or protuberances 17 are cantilevered relative to the ring-shaped distal end face 83 and disposed around opening 16 in a symmetric or patterned arrangement.

Draft Features Relating to Suction Head Embodiments

In one embodiment, one or more of the components of a given suction device are formed using a molding process such as injection molding. For example, in one embodiment the handle component is molded with two parts of a mold coming together. Because of the molding process, a parting line is aligned with a plane that bisects the suction handle. This line and associated plane can effectively be seen when a witness line is visible on the molded part. This line on some embodiments of the handle and other molded parts is referred to as a parting line. The parting line indicates the plane where the mold separates. A given molded part typically drafts from this plane. That is, the part has a suitable positive draft angle so that it can be removed from the mold.

In one embodiment, there is one parting line or plane that bisects the handle 20. There is another parting line that is perpendicular to the axis of the tube inset from the outer most set of protuberances by a distance of about 0.005 inches to about 1 inches. In one embodiment, the parting line is moved away from suction head opening 16 to reduce the possibility of any tissue snagging because of parting line or material arranged or extending with respect to it from the molding process. In one embodiment, with regard to the suction head and its associated vent holes, the draft-axis of a plurality of vent holes is perpendicular to the parting line.

Additionally, in a preferred embodiment, the parting line is not at the rim of the primary opening 16. Rather, the parting line is back toward the handle 20. By their nature, parting lines may be sharp. The location of the parting line prevents any kind of sharp edge on the most used surface of the aspirator 13.

Exemplary Surgical Aspirator and Sleeve Uses

Figure 8A:
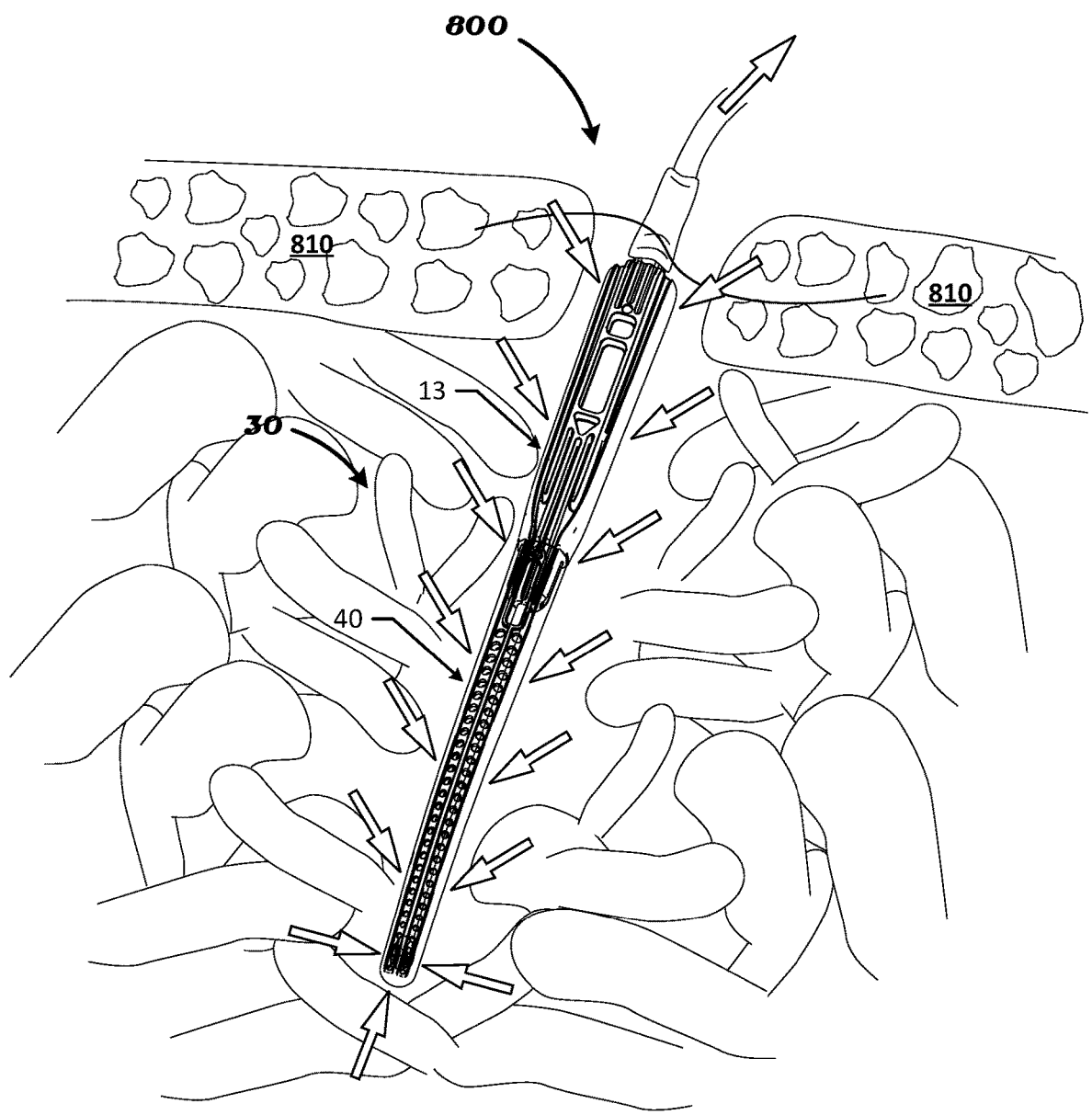
FIG. 8A is a front view depicting the aspirator and aspirator sleeve, inserted into a wound or surgical incision, in accordance with an illustrative embodiment of the disclosure.

FIG. 8A depicts a surgical aspirator 13 and surgical aspirator sleeve 40 that includes one or more of the features and implementations described herein. In particular, the aspirator 13 and sleeve are shown in a typical application such as a medical procedure. For example, the surgical aspirator 13 and surgical aspirator sleeve 40 may be assembled to form a combined suction device 30. The combined suction device 30 is inserted into a wound 800 of a patient. As shown, the substantially straight orientation of the device 30 causes it to resemble a Poole suction device.

Figure 8B:
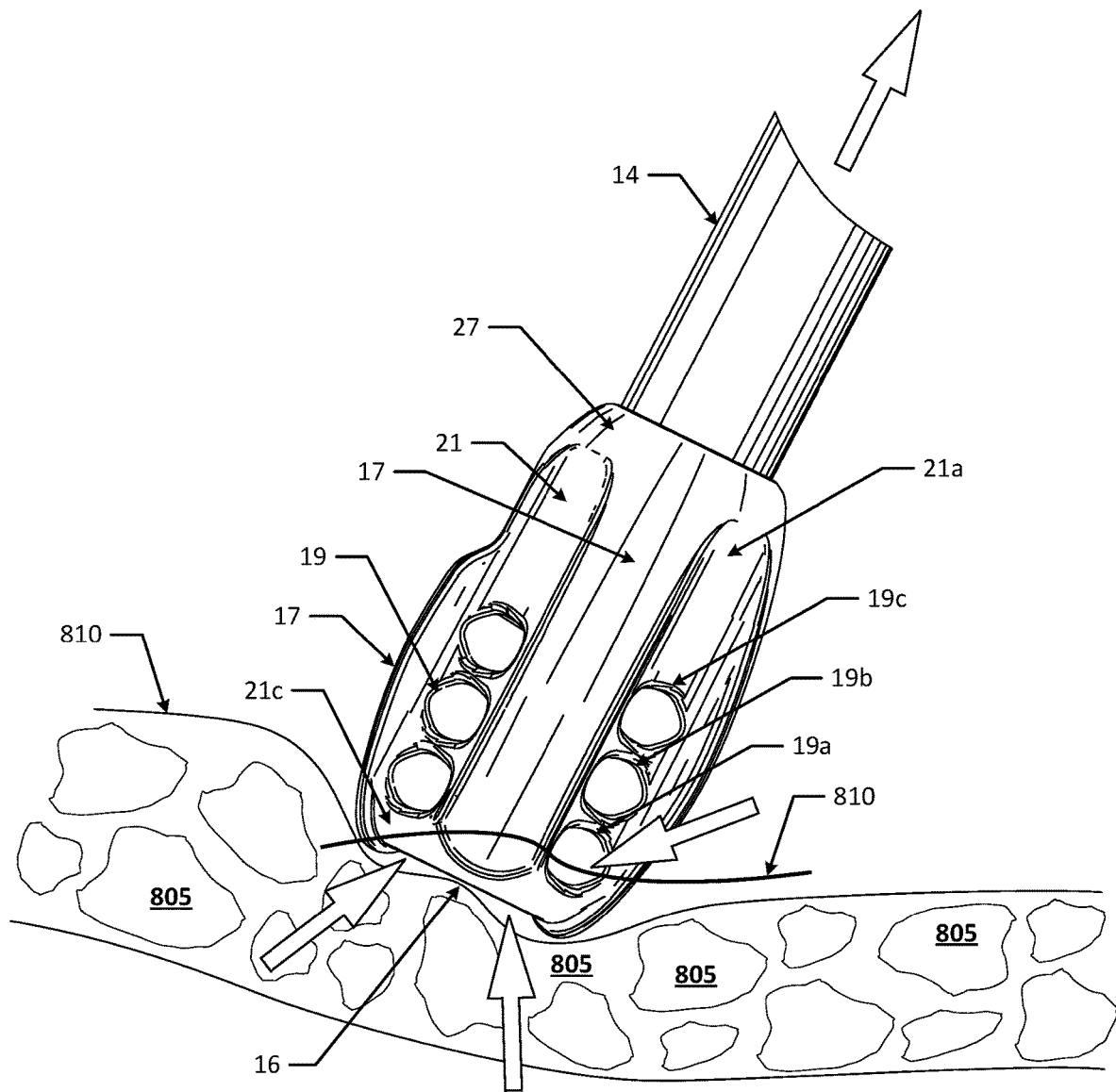
FIG. 8B is a front view depicting the suction head of an aspirator in a sleeveless configuration, inserted into a wound, in accordance with an illustrative embodiment of the disclosure.

An example scenario when a crown or cruciform suction head (or other suction maintaining geometry of suction head configuration) is suitable for use as part of a medical procedure in is depicted and described herein with regard to FIG. 8B.

Referring back to FIG. 1 and FIG. 2A, it should be appreciated that the longitudinal grooves 74 may be covered with portions of the hand. For instance, the user may wrap his or her hand around the grip member 22 such that the palm of the hand engages the second set 77 of longitudinal grooves 74 and the user's fingers engage the first set 75 of longitudinal grooves 74. Moreover, the suction may be varied by using an adjustable sleeve or other mechanism (not shown) that can be coupled to the grip member 22 and is adapted to cover at least a portion of the longitudinal grooves 74 of sets 75 and/or 77.

For example, the user adjusts the position of his or her hand as various levels of suction are needed. When the aspirator 13 and sleeve 40 are deep within a patient's body (e.g., wound 800) such that a majority of the orifices 62 and the cross-holes are covered by a portion of the patient's body, air flow into the sleeve 40 is decreased. This may also occur if some of the orifices 62 and/or cross-holes become clogged. Without sufficient venting into the sleeve 40, the suction level within the interior of the sleeve 40 increases, and tissue may collapse around the aspirator and sleeve combination device. To relieve some of the pressure within the sleeve 40, the user can hold the grip member 22 to cover only a minimal portion of the longitudinal grooves 74 of sets 75 and 77, thereby allowing air to flow into the sleeve 40 and relieve some of the pressure on the tissue.

If, on the other hand, the aspirator 13 and sleeve 40 is only partially enclosed within the patient's body such that a majority of the orifices 62 and the cross-holes are exposed to the atmosphere, air can flow freely into the sleeve 40 to relieve the pressure within the sleeve 40. As such, the suction level within the interior of the sleeve 40 may decrease below a threshold level of interest to a user. To increase the suction within the sleeve 40, the longitudinal grooves 74 of sets 75 and/or 77 can be increasingly covered by the user's hand until the desired level of suction is attained.

Likewise, for example, the aspirator 13 may be used without the sleeve 40 to accurately and efficiently drain fluids from a specific area, such as a surgical site such as shown in FIG. 8B. When placing the suction head 18 within a body cavity, the suction head protrusions or ridges 17 bridge the adjacent soft tissue and maintain the channels open in the grooves 21. Thus, if the suction head opening 16 is clogged, fluid, gas, and materials may flow into the channels defined by grooves 21 and into the orifices 19. The suction head opening 16 also can refer to the bore of the suction head which is in fluid communication with a tubular member in some embodiments. In one embodiment, the protuberances disposed around the opening 16 are sized and arranged to form a flow channel in the presence of tissue that drapes or otherwise contacts the protuberances during a medical procedure. In one embodiment, tissue is pinned or isolated away from the suction head and one or more regions of the tissue cooperate with opening 16 to form a flow channel.

If the aspirator 13 is placed within a cavity so that is oriented substantially orthogonally to a tissue wall, the suction head opening 16, as well as the orifices 19 adjacent the end opening, may be elevated from the tissue wall using one or more protrusions extending from the suction head. In addition, in some circumstances, the fluid, gas, and materials may flow into the channels defined by grooves 21 and into the uncovered orifices 19 located father away from the opening 16. In one embodiment, opening 16 is referred to as a main or primary opening.

FIG. 8B depicts an embodiment of a suction head having a crowned configuration with the various protuberances shown disposed in a tissue 805 and fluid 810 containing environment such as cavity being accessed due to a surgical incision. Various arrows are also show in FIG. 8B. The arrows indicate the direction of fluid flow or the application of suction from a remote vacuum source or other device. A viscous film, semi-liquid layer, or a small pool of liquid is depicted by a bold curved line 805. When using an aspirator in suction head-only mode (no sleeve attached), the suction head and its associate protuberances pushes flexible tissue away from the main opening of the suction head 16. A crown or cruciform arrangement of protuberances is suitable for achieving this as other arrangements of protuberances from a suction head.

The pushing away of or gap maintaining of tissue draping relative to a protrusion or ridge extending from the suction head is achieved using various protrusions. In one embodiment, maintaining suction and fluid flow occurs by one or more protrusions 17 interfacing with tissue or other material to avoid a planar or continuously smooth contacting surface in favor of creating gaps and arcuate flow paths on purpose. FIG. 6B shows an exemplary protrusion 17 relative to end face 83 that can displace tissue to maintain a flow channel. The gaps and protrusions 17 interfacing with tissue create a frontal area for the fluid to flow relative to end face 83 and opening 16. Traditional aspirator suction tips do not have protuberances, and the flexible tissues surround the hole in the suction tip and seal it much like a flapper valve or reed valve. The tissue is deformed due to the presence of the suction head; however, you can also see that the protuberances keep a path open (frontal area) for fluid flow.

In one embodiment, the length, width, and height of an exemplary protuberance range from about 0.001 inches to about 0.20 inches. The protuberances disposed on or formed from or otherwise constituting a component of the suction head can be any suitable shape and dimension suitable for use with a suction head. As examples, protuberances can include, without limitation, bumps, knobs, tangs, bosses, non-sharp elements, ridges, spheres, hemispheres, rounded projections and other objects and members. In one embodiment, the protuberances are sized and shaped to create a flow channel when in use relative to organs, tissue and other biological materials and structures.

Assembly Fit Profile/Substantially Cylindrical Configuration Embodiments

In one embodiment, the mating surface and associated areas of the handle member 20 and sleeve 40 may have conical type configurations (e.g., truncated cone portion with an increasing/decreasing cross-sectional area along an axis). Conical configurations, however, often mean that the friction force joining the handle member 20 and sleeve 40, as an assembly, does not occur until engagement of the sleeve 40 and handle member 20 is nearly complete. Also, in certain instances, the aspirator 13 of the handle member 20 interferes with the end (e.g., distal sleeve end portion 45) of the sleeve 40 before the sleeve 40 is completely engaged on the handle member 20.

One or more features, such as grooves, ribs, struts, or other structures can be disposed or formed at the distal end of the sleeve 40 to contact certain areas of the aspirator 13 of the handle member 20 for engagement purposes. However, these features may serve to diminish the fluidic performance of the device and care in their selection and alignment is important. In some embodiments, these features at the distal end of the sleeve are avoided because they do not yield a practical benefit, while simultaneously complicating the manufacturing of the assembly.

Likewise, these features may introduce tactile ambiguity during the assembly process (e.g., the engagement) of the sleeve 40. For example, the sleeve 40 is made of a material whereby shrinkage during injection molding is difficult to predict. Therefore, it is often the case that the manufactured sleeve 40 is slightly shorter than initially intended. A short sleeve 40 may ruin any anticipated assembly tactile feedback. Further, for features at the closed end of the sleeve, the distal end, to perform as desired, the sleeve 40 would have to meet the shoulder 37 on the handle 20. In addition, features at the distal end of the sleeve disposed within the lumen of the sleeve would have to be contacted simultaneously; given a sleeve 40 that is slightly shorter than intended, this may be impossible to implement.

Despite these shortcomings, proper fit engagement between the sleeve 40 and handle member 20 is possible using various implementations and constraints. The sleeve 40 is designed to mate or couple with the handle member 20 at a substantially cylindrical sleeve coupler 26, 260 and be secured thereby during use of the handle-sleeve combination such that interference commences with and continues through sleeve and sleeve coupler engagement. Accordingly, once the sleeve is secured to the handle, the frictional forces are such that the two components will not disengage during a medical procedure unless pulled apart by a person or device. Additionally, it is preferred that the assembly process (e.g., the engagement) provide tactile feedback to the user.

For example, when the sleeve 40 and handle member are engaged via a sleeve coupler to form a combined secure assembly of both components, the user is able to feel or otherwise sense the gradually increasing friction associated with the mating or coupling of the components. This relationship is illustrated graphically by FIG. 13, depicting the force-engagement relationships for two different coupling member profiles and thus indicative of a user's tactile experience with such a sleeve and aspirator combination process. The two force profiles of FIG. 13 also track the engage of the two sleeve coupler designs and associated sleeves shown on the right (substantially conical) and left (substantially cylindrical) sides of FIGS. 11A-11C.

Given the conditions of a procedure room and the prevalence of fluids, having a comfortable and satisfying process when forming a suction device by combing an aspirator and sleeve is important. The embodiments described herein relating to a substantially cylindrical sleeve coupler design allow a user to complete the combination of both components and have a level of confidence that a secure fit has been achieved. This is an advantageous design feature. In addition, a high level of strength is not required for a substantially cylindrical sleeve coupler which is unlike various substantially conical sleeve couplers as illustrated by the assembly force spikes of FIG. 13.

The designs disclosed herein address many of the assembly shortcomings relating to a substantially conical sleeve coupler such as coupler 265 shown on the right side of FIGS. 11A-11C in conjunction with sleeve 1205 and handle 1255. In contract, as illustrated in FIGS. 9A, 9B, and the left side of FIG. 11B, preferably the mating areas of the sleeve 1200 and sleeve coupler 260 of the aspirator are now substantially cylindrical. FIGS. 12A and 12B are side cutaway views showing the engagement of an aspirator sleeve 1200 and the interference therewith over an engagement length EL that follows which correspond to the sleeve 1200 and sleeve coupler 260 shown on the left side of FIGS. 11A-11C. More particularly, FIGS. 9A and 9B illustrates the substantially cylindrical profile of the sleeve coupler 260 (e.g., the mating area) of the handle member 1250.

FIG. 9A is a perspective view depicting an aspirator 130 that includes a suction head 18, a tubular member 14, a shoulder 37, a barb 24 for a suction source, a handle 1250 and a sleeve coupler 260. FIG. 9B is a perspective view depicting the interface of a tubular member 14 and a handle member of an aspirator 130 and sleeve coupler 260 and handle 1250. The sleeve coupler 260 and handle 1250 are also described with regard to the embodiment shown on the left side of FIGS. 11A-11C and sleeve 1200.

The handle member 1250, as illustrated in FIGS. 9A, 9B, 12A and 12B, includes the sleeve coupler 260 and has a shoulder 37. The handle member 1250 additionally includes tube coupling member 260. The aspirator may include additional features, as disclosed above, such as the tubular member 14 and the suction head 18.

Particular details relating to the engagement of a substantially cylindrical profile of the sleeve coupler 260 of the handle member 1250 relative to an alternative embodiment is illustrated by FIGS. 11A-11C and FIGS. 12A and 12B. FIGS. 11A-11C includes cutaway views of both a substantially cylindrical configuration (left) and a substantially conical configuration of sleeve couplers or mounts 260, 265. The left hand portion of each of FIGS. 11A-11C shows features relating to an embodiment that includes a substantially cylindrical sleeve mount or coupler. The right hand portion of each of FIGS. 11A-11C shows features relating to an embodiment that includes a non-substantially cylindrical sleeve mount or coupler such as a conical sleeve mount or coupler. In one embodiment, an outer surface of the sleeve coupler 260 portion of the handle, which is the portion that contacts the sleeve, has a cross-sectional profile that is substantially cylindrical along its length.

The left side of FIG. 11B shows an exemplary sleeve coupler 260 having a substantially cylindrical profile over an engagement length EL with an initial engagement point P1 and the end of engagement occurring at point P2. In FIG. 12A, engagement has started and sleeve 1200 is interfering with coupler 260 in zone Z1. The engagement length EL has an initial zone or region Z1 and a terminal zone or region Z2. The assembly force remains substantially the same or gradually increases as the sleeve 1200 is engaged to enter zone Z2 and have engagement terminate at point P2. FIG. 11C shows a sleeve 1200 having a volume V on the left side. The sleeve 1200 is slightly deformed by the substantially cylindrical coupler 260. FIG. 11C shows a sleeve 1205 having a volume $V_{con}$ on the right side as significantly and asymmetrically deformed by substantially conical coupler 265.

The substantially cylindrical shape of the sleeve coupler 260 is chosen such that the engagement force between the sleeve and the coupler is gradually increasing as the two are paired with interference being present through the engagement length EL in both Z1 and Z2. That said, the assembly force in Z1 and Z2 are not significantly different so that a sudden force spike does not occur in Z2. This follows because interference starts from the time of engagement of the sleeve with the sleeve coupler but the profile of coupler 260 generally conforms to that of cylinder without significant deviations.

In FIG. 11B, the start of this engagement of a sleeve with substantially cylindrical coupler 260 starts at point P1 with the sleeve coupler having a thickness H1. Interference starts upon engagement at P1. With thickness H1, the sleeve 1200 and couple 260 interfere. In contrast with a conical coupler 265 interference does not commence with engagement at thickness $H_2$ which is less than $H_1$. Instead, with the conical sleeve coupler 265, sleeve 1205 does not interfere with the sleeve coupler 265 over the zone Z3 at thickness H2, as shown on right side of FIG. 11B, even though the sleeve 1205 has received the coupler 265. The thickness H2 of sleeve coupler 265 is not thick enough to engage the sleeve 1205 over region Z3. As a result, given the conical taper of sleeve coupler 265, any interference and tactile feedback is delayed. When interference does start, at the end of Z3 or after Z3, the conical profile causes the forces to suddenly increase.

A strong assembly force occurs in Z4 as engagement terminates. Engagement can terminate with coupler 265 prior to reaching the shoulder because of the high assembly force which must be overcome to push the sleeve 1255 through Z3. As shown, in FIGS. 11A and 11C, the sleeve 1205 and coupler 265 are trumpet shaped such that interference does not occur in Z3 and strong assembly forces are required in Z4. In one embodiment, a substantially cylindrical sleeve coupler is a sleeve coupler that avoids the assembly force profile of a conical or substantially conical sleeve coupler as described herein. This type of coupler can be identified in like of the description provided herein and the associated force behavior and unwanted force spikes which are avoided while still providing tactile feedback over EL.

FIGS. 12A and 12B are side cutaway views showing the engagement of an aspirator sleeve and the interference therewith over an engagement length EL and generally track the substantially cylindrical assembly of sleeve 1200 and coupler 260 of FIGS. 11A-1C and the related non-quantified assembly force relationship of FIG. 13. As shown, the sleeve 1200 buts against the shoulder 37 of the handle 20 when engaged (e.g., complete engagement). With a substantially cylindrical sleeve mount 260 as part of the handle design, the interference of the sleeve 1200 and handle member 260 increases the separation force with increased engagement as the sleeve moves along a member of the handle, from the point of first contact to complete assembly. The assembly force transitions as sleeve 1200 interferes with sleeve coupler 260 from zone Z1 to zone Z2 along engagement length EL is a gradual transition and in one non-limiting embodiment can track the curve G1 shown in FIG. 13. As noted below, the disclosure is not limited to the relationships of FIG. 13, but provides them as informative guidance to distinguish substantially cylindrical and substantially conical sleeve coupler profiles.

To further summarize the benefits of using a substantially cylindrical sleeve coupler some general assembly force versus sleeve-handle engage are illustrated graphically by FIG. 13. Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. With being held to any particular theory or mechanism, the forces displayed in FIG. 13 relating to combining an elastic sleeve with either a substantially cylindrical sleeve coupler G1 and a substantially conical sleeve coupler G2 are meant to illustrate general trends relating to differences between the respective assembly processes and not detailed quantitative date.

The graph shows a plot of assembly force versus sleeve-handle engagement, comparing substantially conical G2 and substantially cylindrical G2 profiles for these two types of sleeve couplers. As illustrated by FIG. 13, with substantially cylindrical sleeve coupler profile G1, a significant assembly force exists if there is any engagement (e.g., high initial slope near the start of engagement). This follows because interference commences with engagement as discussed herein for such a profile G1. By comparison, with substantially conical sleeve coupler profiles G2, for much of the perceived engagement there is negligible force (e.g., low initial slope near the start of engagement). In addition, the force near complete engagement for the G2 profile is significantly larger than that at the start of engagement. This follows because the thickness of the conical sleeve coupler typically does not interfere with the sleeve when it first crosses into the sleeve lumen. In one embodiment, profile G1 is has a force profile that increases during sleeve engagement and then levels off as engagement is completed. In contrast, profile G2, has a gradually increasing force during assembly and then the assembly force increases significantly at the end of the assembly process. This results in a user of a substantially conical profile (G2 profile) having excessive force feedback at the end of the process. This high force profile at the end of assembly may even result in making assembly impossible. In part, this demonstrates the tactile feedback and assembly benefits of the substantially cylindrical profile G1.

Internal Geometry of Handle and Internal Fluid Flow Path Design Embodiments

In part, the disclosure relates to an aspirator or other medical device that includes a flow path through which liquids, gases, debris, and other material can flow through. In particular, a handle or other support for a suction device that includes a flow path disposed therein is one aspect of the disclosure. For some embodiments, a flow path is formed from one or more cavities or volumes that are defined by the geometry of the inner walls and structures of a given handle or other support member. In some embodiments, the handle or support member are formed by a molding process. The handle or support member are formed with proximal and distal end faces that are in fluid communication with a flow path that is in fluid communication with an aperture or hole defined by each respective end face. These apertures can be used to connect a tubular member and a barb, respectively, in one embodiment. The flow path allows for fluid, gas or other material transport and spans the inner region of a given handle or support member between the proximal and distal end faces and their respective apertures.

FIG. 10A is a schematic view of a curve 175a in a plane with a longitudinal axis of rotation in the plane by which a surface or solid of revolution can be generated to define a flow path within a handle or other member. The arrows show a direction of rotation about which the curve can be rotated relative to the longitudinal axis $L_{axis}$. In some embodiments, the flow path is designed to have a geometric shape that can be defined by a surface of revolution. A surface of revolution is one or more surfaces of a solid of revolution. Given that the flow path is one or more cavities defined by the material of a handle or support member, the surfaces that define the cavity of the flow path can be surfaces of revolution. The term revolute can also be used to refer to a surface of revolution or the shape of the fluid flow path within a handle or other member.

The curve used to generate a given surface or solid of revolution (also referred to as a revolute) can include straight line segments or curved segments without limitation. The curve 175a includes linear and curved sections. The surface that results from rotating the curve 175a about the longitudinal axis is shown as fluid flow path 175b of handle 240 in FIG. 10B. This flow path includes the section of the tubular member 140 disposed in the handle as shown in FIG. 10B. In one embodiment, there is an even number of cavities defined from the barb 240 to the suction head 180. These are depicted and described in various ways with regard to FIGS. 10A-10D. These cavities can include the suction head bore 110d, cavity defined by section of tubular member bore disposed in the handle, and a second flow cavity adjacent thereto and a first flow cavity that includes the bore of the barb or suction connector. These cavities are in fluid communication with each other and define a flow path. A portion of this flow path is internal to the handle 260. Another portion of this flow path is external to the handle. The external path includes the section of the tubular member not disposed in the handle and the suction head bore as shown in FIG. 10D. FIGS. 10B and 10C illustrate cutaway views of the handle member 200 and include details relating to the inner flow path 175b defined by curve 175a and the portion of the tubular member bore disposed in the handle.

In one embodiment, the inner flow path 175b can also be defined by a combination or sum of three elongate adjacent cavities having differing dimensions. The handle 200 can include a substantially cylindrical sleeve coupler 260 in one embodiment. Alternatively, for other support members for other medical devices that include an inner flow path, a substantially cylindrical sleeve coupler may or may not be included. The regions of fluid flow shown relative to the suction head 190 in FIG. 6A such as bore 193 are in fluid communication with fluid flow path 175b in one embodiment.

In FIG. 10B, various subsections of flow path 175b of the handle member 200 are shown. In one embodiment, the flow path 175b is a cavity defined by a surface of revolution 175a. In one embodiment, the flow path 175b is a cavity defined by stacked arrangement of elongate cavities. Three cavities (proximal/first fluid flow cavity) 110a, (transitional or second fluid flow cavity) 110b, and segment of bore 110c of tubular member in the handle are in fluid communication with one another and each have a respective length L1, L2, L3 and a respective inner thickness T1, T2, and T3. These three cavities 110a, 110b, and 110c define a flow path. This flow path continues with the suction head bore 110d that has a thickness T4. Elongate cavity 110a is a truncated cone in one embodiment. The material used to make the handle 260 is a polymer such as a plastic in one embodiment. The handle can be formed through various molding processes. In addition, the suction head 180 can be formed through various molding processes. In one embodiment, one or both of the suction head and the handle can be printed using a 3D printer or other similar manufacturing process.

In one embodiment, elongate cavity 110c is either defined by handle 200 or by a tubular member 140 disposed in the handle 200. As shown in FIG. 10B, elongate cavity 110c is the inner bore of tubular member 140. The outer diameter OD of the tubular member 140 is also depicted herewith. The outer diameter OD is selected to be less than the diameter T4 of the suction head 190 in one embodiment. Typically, the elongate cavity 110c is defined by a tubular member 140 having an inner diameter T3 such that the tubular member 140 is disposed within the handle 200 a distance L3. In embodiments that do not include a tubular member 140, the length of cavity 110C is also L3.

In one embodiment, the transition between elongate cavity 110c and elongate cavity 110b is a junction between a cavity defined by handle and an inner bore 110c of member 140. In this way, the handle includes a junction between dissimilar materials in one embodiment. This junction is formed at the proximal end of the tubular member 140 and the distal end of elongate cavity 110*b*. In one embodiment, the thickness T2 of elongate cavity 110*b* is approximately the same distance as the outer diameter of tubular member 140. In one embodiment, inner diameter of elongate cavity 110*b* is greater than inner diameter of elongate cavity 110*c*.

In the aggregate, from a cross-sectional view, these three cavity sections 110*a*, 110*b*, and 110*c* form a composite shape. The composite shape is approximated, from a cross-sectional view, as three rectangular shapes. The inner diameter of the tubular member T3 is less than the thickness T2 in one embodiment. As shown in FIG. 10B, L1 is greater than or equal to L2. L2 is greater than or equal to L3. L is greater than L3. The thicknesses of each section 110*a*, 110*b*, and 110*c* are also increasing when moving from the tubular member 140 to elongate member 240—that is moving distally to proximally. In one embodiment, elongate hollow member 240 is suction port or barb. As shown, T1 is greater than or equal to T2 which in turn is greater than or equal to T3. In one embodiment, the handle 260 as shown in FIG. 10B includes a metal tubular member such as tubular member 140. The tubular member has a bore, which acts as a flow cavity or flow path.

Inside the handle, this is a fluid flow path. The flow path can extend through the tubular member bore to the bore of the suction head in one embodiment. In addition, the handle portion which surrounds the tubular member effectively defines a tubular cavity 289 that surrounds and secures the tubular member 140. The proximal end (right side) has the barb 240 and a proximal cavity or fluid flow cavity 110*a*. The tubular cavity 289 is not typically a flow cavity, with the flow of fluid being carried through the tubular member 140 disposed in the tubular cavity of the handle 260. [0208] In one embodiment, the stepped or stacked arrangement of adjacent and continuous cavities 110*a*, 110*b*, and 110*c* is referred to as a spyglass configuration or spyglass shaped cavity.

In one embodiment, the elongate cavities form or define an internal fluid flow path. The longitudinal axis of the handle, which is disposed along the internal flow path, is the axis about which a stepped curve or line is rotated to define a volume within the handle. This volume is an exemplary internal flow path in one embodiment. The geometry of the internal flow path is a stepped revolute in one embodiment. These cylindrical segments effectively have a spyglass or telescoping or nested arrangement such that each subsequent segment can nest or fit within the preceding segment even though the shapes define cavities, which are fixed in the handle and bounded by the inner surface geometry of the handle 200. In one embodiment, the handle defines a region of two or more elongate cavities arranged along a central longitudinal axis or shifted relative thereto.

In one embodiment, the stepped features of the flow path 175*b* of a handle 200 become successively smaller, from proximal end to distal end, until the last sections of the flow path meets the tube 140 which has a cylindrical diameter and bore 193 of suction head (if a suction head is part of the design). Each cavity section 110*a*, 110*b*, and 110*c* can have various cross-sections and need not be cylindrical. The stepped revolute features of the flow path 175*b* may include draft (taper). Flow path section 110*a* includes a positive draft angle, and section 110*b* can optionally include a positive draft angle. At the junction between 110*a* and 110*b*, a sharp corner or turn or stepped transition 233 is present.

This in contrast to corner 122*a* in which a radius or curve is present and a sharp edge is avoided. T2 is generally a smaller distance than T1. From the barb end 240, typically there will two or more cavities. In one embodiment, only three cavities are used to define the flow path. Also, the diameter of the mouth at the barb 240 is T1 in some embodiments. The thickness of T1 and the wall of barb 240 is configured to provide sufficient wall thickness to allow coupling to a suction source via a conduit or tube that attaches to barb 240.

FIG. 10D shows the suction head 180 which is in fluid communication with the bore 110*c* of the tubular member 140. Additional details relating to the suction head 180 and the elongate cavity sections of handle including the interface of the suction head bore 110*d*, flared tube end 122, and suction head housing is shown. Elongate cavity 110*c*, which is the inside of the tubular member 140, is defined by the inner surface of the tubular member 140. The inner surface of the suction head 179 defines the suction head bore 110*d*. The suction head bore 110*d* is a cavity that is in fluid communication with elongate cavity 110*c* of the tubular member, which the bore of the tubular member. The thickness of the suction head bore is shown as T4 in FIG. 10D. These two cavities, 179 and 110*c* come together at a flared region 122 of the tubular member that has a flaring angle.

As shown in FIG. 10D, the flared region has a corner 122*a* or surface junction 122*a* that is where inner suction head surface 179 terminates at the flared end of the tubular member which is disposed in the body of the suction head 180. This corner 122*a* is a transitional region and is engineered to be a smooth curve in one embodiment. With respect to FIG. 10B, in one embodiment, cavity 110*d* is a cylinder or a cylinder with a taper. The taper can be greater than or equal to about 0.5 degrees in one embodiment. The diameter of cavity 110*d* is greater than the cavity 110*c* in one embodiment. Elongate cavity 110*a* and elongate cavity 110*b* have a cavity interface or junction 245. This interface 245 is a transition from thickness T1 to thickness T2. Elongate cavity 110*c* and elongate cavity 110*c* have a cavity interface or junction 247. This interface 247 is a transition from thickness T2 to thickness T4 and T3. Thickness T3, the inner tube diameter, is typically less than thickness T2.

In one embodiment, the corner 122*a* has a curve such a circular section or sector having a radius, an elliptical section having an elliptical curve, or another curve. The corner 122*a* near the flared region 122 is constrained to avoid a sharp edge or abrupt transition or step.

Engineered Clearance of Aspirator Sleeve Combination

After a sleeve is assembled with the aspirator, the proximal end of the elastic sleeve conforms to the profile of the handle and is approximately aligned with the handle over a distance from the shoulder until a bend is encountered along the tubular member. In one embodiment, as part of the design of the combined sleeve and aspirator, one more clearances have been engineered into the distal end or tip of the sleeve. The one or more clearances in this sleeve area allow the sleeve to have a more gradual bend because of the skew angle between an axis of the bent sleeve tip and an axis of the bent distal portion of the tubular member. By constraining this skewing angle and optionally other skewing angles and clearances, the angle by which the sleeve bends relative to the longitudinal axis of the handle is reduced such that the sleeve appears straighter even though it contains a tubular member with a bend. In one embodiment, this gradual bend of the sleeve allows the combination of sleeve and aspirator to more closely follow the shape of a straight, traditional, Poole suction device.

Figure 14A:
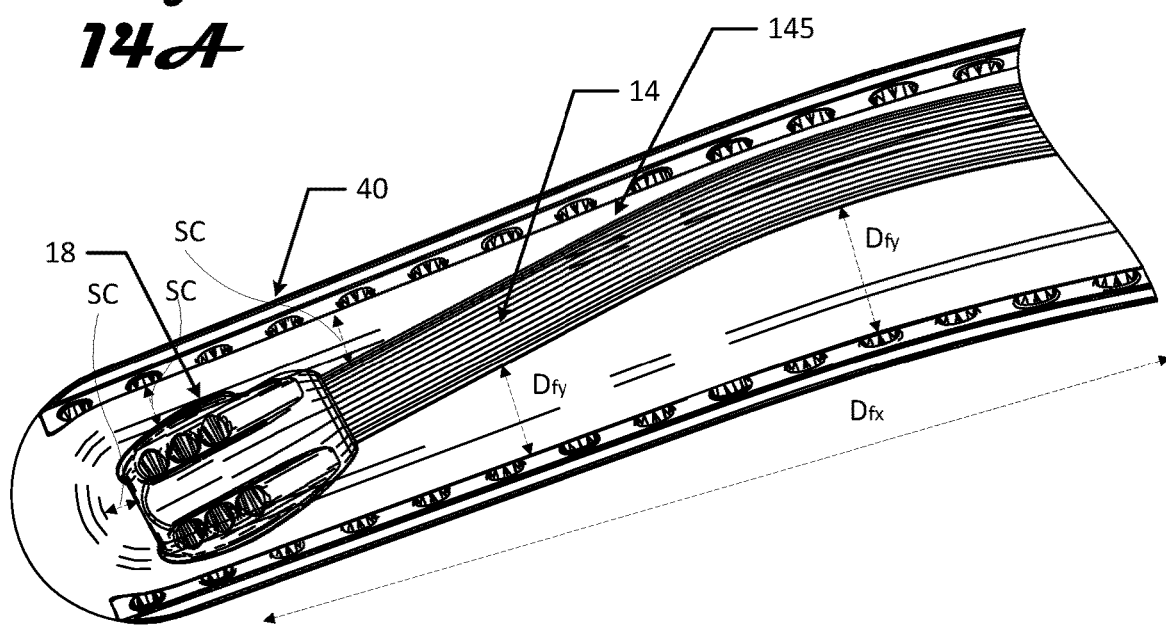
FIGS. 14A and 14B are cutaway views depicting bending of an aspirator after assembly and combination with an aspirator sleeve and various engineered clearances, in accordance with an illustrative embodiment of the disclosure.

Various embodiments of the aspirators described herein benefit from including an engineered clearance between the suction head and the inner sleeve wall. For example, this clearance is typically a gap between the end face of the suction head and the terminal end of the inner sleeve wall near the end of the elastic sleeve. This clearance SC is shown in FIGS. 14A, 14B, and 15A, 15C and 15D. Although SC can also include any clearance distance between the suction head and the sleeve wall at the distal end of the sleeve when the suction head is disposed therein after aspirator sleeve assembly, as shown in FIG. 14A, preferably, SC is the distance between the inner sleeve wall end portion and an end face or end region of the suction head or a side clearance relative to the side of the suction head as shown in FIGS. 14B and 15A, 15C and 15D. The clearance between the suction head to the inner sleeve wall SC is advantageous relative to aspirators that lack such a clearance.

In various embodiments, as shown for example in FIGS. 14A, 14B, and 15A-15D and other embodiments described and depicted herein, including a clearance between the suction head and the inner sleeve wall permits the various skewing angles described herein. In contrast, for an aspirator and sleeve system that lacks such a clearance and the associated possible ranges of skewing angles, there is interference between the suction head and the end portion of the sleeve. This creates problems such as sticking and unwanted sleeve bending or extreme hooking when the sleeve and aspirator are combined to form an assembly.

Figure 15A:
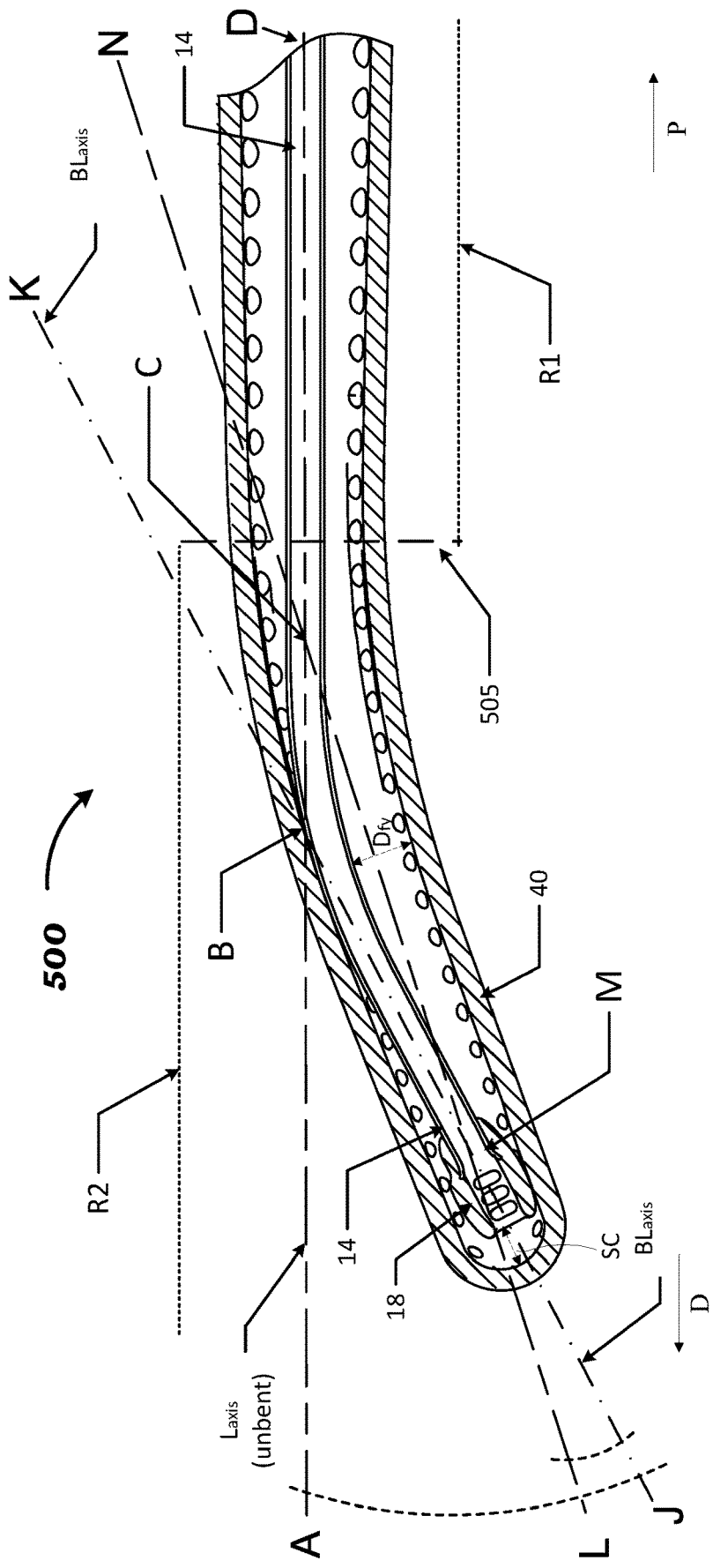
FIGS. 15A, 15C and 15D are cutaway views depicting engagement of a tubular member and suction head of various aspirator embodiments while engaging with an aspirator sleeve and various axial and angular relationships, permitted in part based on an engineered clearance, in accordance with an illustrative embodiment of the disclosure.

In one embodiment, one or more engineered clearances at the tip area of sleeve allows the axis of the tubular member of the aspirator after a bend in the tubular member to be askew with the axis of the sleeve in that area. FIGS. 15A, 15C and 15D show various embodiments of sleeve and aspirator combinations 500. The region R1 shows a tubular member and a sleeve aligned before the bend B. The region R2, after region R1, includes the bending sleeve and the bend B of the tubular member. In some embodiments, the sleeve bending occurs before or after the tubular member bend B. Although discussed in more detail herein, this can be seen with the axis passing through the bent tubular member shown by line segment JK as compared to the axis through line segment LN that corresponds to an axis of the bent sheath 40.

Figure 14B:
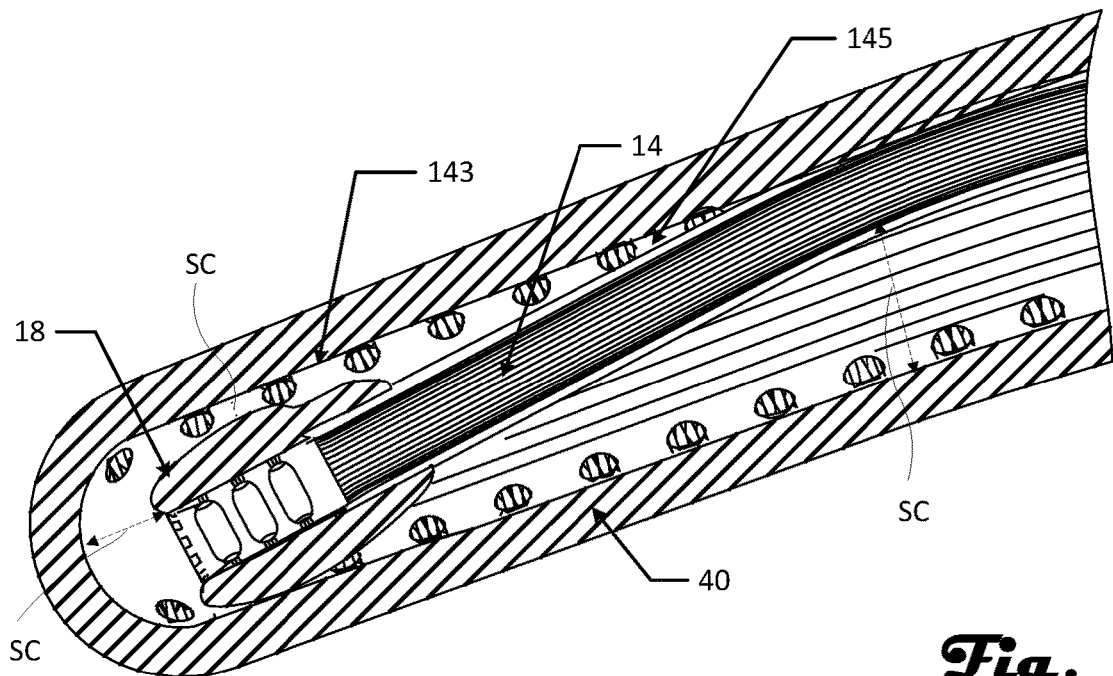

An exemplary engineered clearance SC associated with the suction head 18 and its respective engagement with sleeve 40 as well as various clearances $D_{fy}$ between the bent tubular member 14 and the inner sleeve wall 143 are shown in FIGS. 14A and 14B. The engineered clearance SC near the suction head clearance improves suction and fluid transfer through the sleeve and into tubular member 14 and results in less friction between the suction head 18 and the sleeve 40 during sleeve and aspirator coupling. In one embodiment, the engineered clearances described herein are greater than about zero to about 0.2 inches.

In one embodiment, there is an engineered clearance SC, which is a distance, from a point on suction head, such as a point on distal end face of suction head, to the distal terminus of the inner wall of the sleeve. This clearance within the sleeve near its distal tip as measured from a normal from the distal end face of the suction head can range from about 0.080 to about 0.11 inches. In one embodiment, the clearance ranges from about 0.005 inches to about 0.100 inches, wherein the clearance is between the distal end face of the suction head and the sleeve inner surface. In one embodiment, the clearance between inner sleeve wall and a point of suction head or tubular member ranges from about 0.005 inches to about 0.100 inches.

In one embodiment, there is radial engineered clearance SC extending from a normal to the surface of the tubular member to the inner sleeve wall of the sleeve. This radial clearance can range from about 0.001 inches to about 0.020 inches. The various engineered clearances SC can vary relative to the tubular member, the suction head, and otherwise within the sheath as space or clearance is set which permits or constrains various skewing angles, alone or in combination as design parameters.

In addition to the generalized clearance SC which include radial or axial clearances as described herein without limitation, other clearances or spaces can be described relative to the aspirator and sleeve designs. As a result of these two axes being shifted relative to each, there are various clearances such as clearances $D_{fy}$ that are present by design. These clearances are shown in a y directional relative to a range or distance $D_{fx}$. The distance $D_{fx}$ is an offset relative to the longitudinal axis of the sleeve 40. $D_{fy}$ provides one reference frame to measure the various D, clearance or deflection values, which vary along the $D_{fx}$ range.

In one embodiment, a relative extremum such as the maximum $D_{fy}$ value of the set of $D_{fy}$ values that range of distance $D_{fx}$ can be identified as the maximum engineered clearance value. This is but one exemplary measurement of clearances. As discussed below, the various angles that constrain the relationship of the tubular member, suction head and inner sleeve wall 143 are selected by design to create clearances between these various components. The angle LMJ is one skewing angle that can be constrained to allow one or more clearances such as the $D_{fy}$ clearances shown. Other skewing angles can also be constrained as described herein. Example skewing angles, as can be seen with regard to FIGS. 15A and 15B, include without limitation one or more of the following angles: angle ABL, angle ABJ, angle LMJ, angle ABJ, angle ACL, angle ACJ and other combinations of angles shown in FIGS. 15A and 15B.

Angle ACJ corresponds to the bend angle of distal portion (upper portion) of tubular member relative to the handle and is one skewing angle that can be used to constrain one or more clearances. Angle LMJ corresponds to the skewing between the upper portion of the sleeve and the upper portion of the tubular member after the bend is another skewing angle that can be used to constrain one or more clearances. Angle ACL corresponds to the bend angle of sleeve relative to the handle and is one skewing angle that can be used to constrain one or more clearances. In one embodiment, the angles, ACL and ACJ range from about 10 degrees to about 45 degrees.

The engineered clearance between the tubular member and the sleeve $D_{fy}$ results in a sleeve that is less sharply bent as would be the case if $D_{fy}$ were removed. With $D_{fy}$ removed, the sleeve and the tubular member 14 would closely track and conform to each other and the sleeve would appear considerably more bent and hooked. Such bending and hooking make the combination sleeve and aspirator combination harder to assemble and also make the combination look less like other suction devices with a straighten sleeve end portion such as a Poole suction device.

As a result, the clearances engineered between an elastic sleeve and a tubular member, when both are combined together, address these problems. As discussed herein, the various clearances between the sleeve and elements disposed within the sleeve constrain skewing angles between the various axes described herein constrain and establish ranges for these angles. Additional details relating to the engineered clearance is discussed herein with regard to FIGS. 14A-16.

In one embodiment, the arrangement of two combinable components of a suction system are sized and arranged relative to other components to provide an amount of clearance. In one embodiment, clearance refers to a distance between two objects or an amount of clear space. A given clearance SC can be described in terms of a distance in one or more directions relative to the objects at issue such as a suction head surface, inner sleeve wall surface, tubular member surface and other distances measured relative to sleeve inner wall and a surface point of the tubular member or suction head in distal region of sleeve. Clearance SC can also be described in terms of one or more volume elements in which object pairs do not collide or only selectively collide at certain points, lines angles or surfaces. In one embodiment, various angular ranges of intersecting or offset axes are described herein which provide constraints for the axial and angular positions of a sleeve relative to the tubular member of an aspirator. These angular and axial constraints or parameters are suitable for achieving various engineering clearances of interest.

As illustrated in FIGS. 14A, 14B, 15A, 15B, and 16, the suction head 18 and tubular member 14 may include one or more predetermined clearances such as a threshold clearance. The foregoing clearances can be engineered to address various design and user interactions with a suction device such as assembly a sleeve with an aspirator. A clearance is interposed between a sleeve and the suction head and the tubular member to which it is attached in one embodiment. This clearance functions to more easily allow aspirator 13, 130 to combine with a sleeve 40, 120 and provides one or more offset distances between the tubular member, the suction head and the inner wall of the sleeve in various embodiments. The various axis such as the longitudinal axis of each of the tubular member and sleeve, for the respective bent and unbent portions as well as the longitudinal axis of the handle and any offset axis relating to the foregoing can be described as a first, second, third, . . . . Nth axis without limitation.

More particularly, FIGS. 14A and 14B illustrate exemplary clearance associated with the suction head 18 and its respective engagement with sleeve 40. The inner surface 143 of the sleeve 40 is shown. A bend angle 145 can be measured relative to a tangent to inner surface 143. The sleeve can be positioned relative to a suction head with a clearance D between them. The sleeve 40 can be positioned relative to a suction head with a clearance D between them. In one embodiment, D ranges from about 0.005 inches to about 0.050 inches.

FIG. 15A illustrates a cutaway view of engineering clearance SC relative to the suction head 18 attached to a tubular member 14 having a bending disposed within the sleeve 40. $D_{fv}$ can range along various values along the bent section of the sleeve. In one embodiment, an average of these values can be used to measure the engineered clearance. In other embodiments, the maximum $D_{fv}$ value from tubular surface to inner sleeve wall is used as the engineered clearance.

Figure 15B:
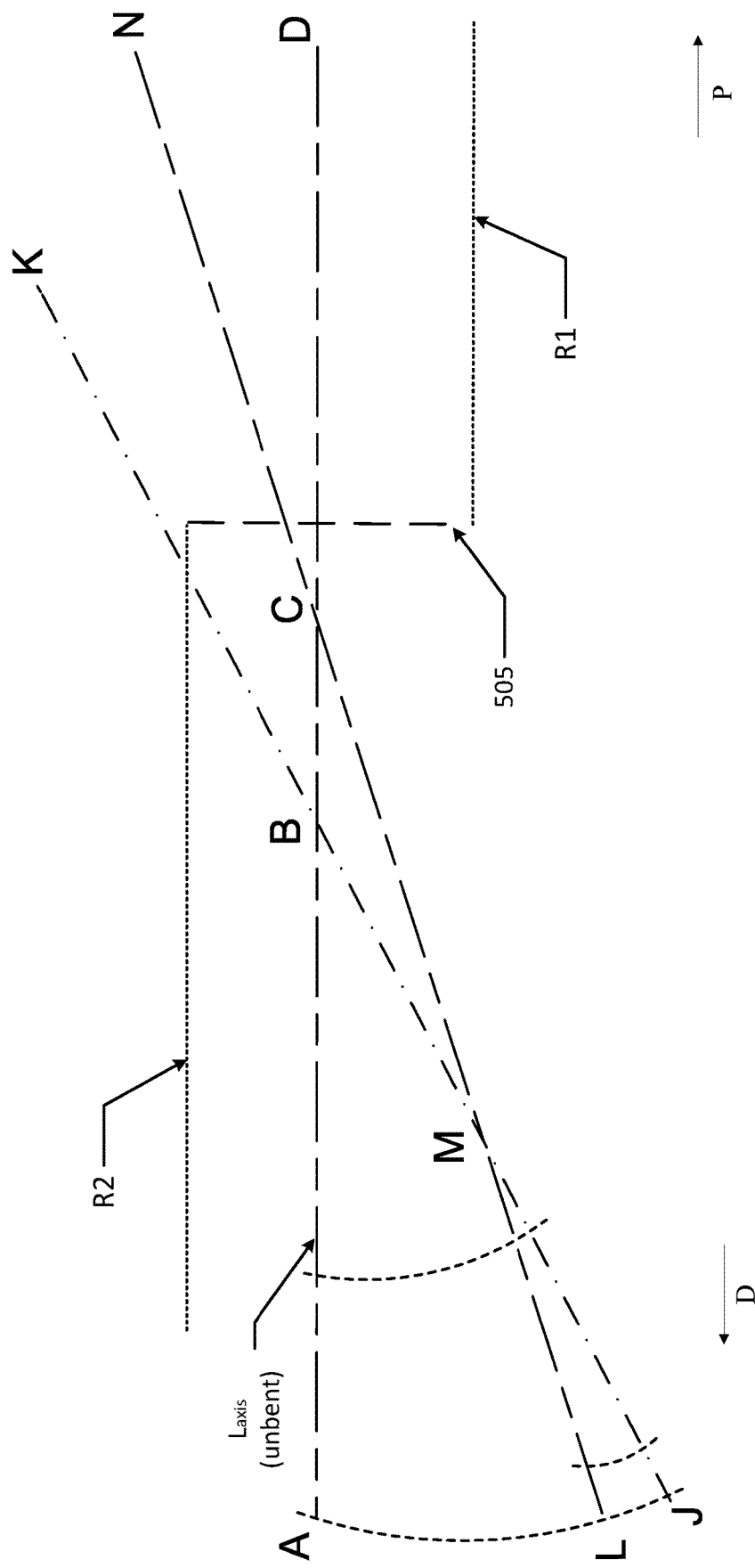
FIG. 15B is a schematic representation that depicts some of the various axial and angular relationships of FIG. 15A without the aspirator and sleeve in accordance with an illustrative embodiment of the disclosure.
Figure 15C:
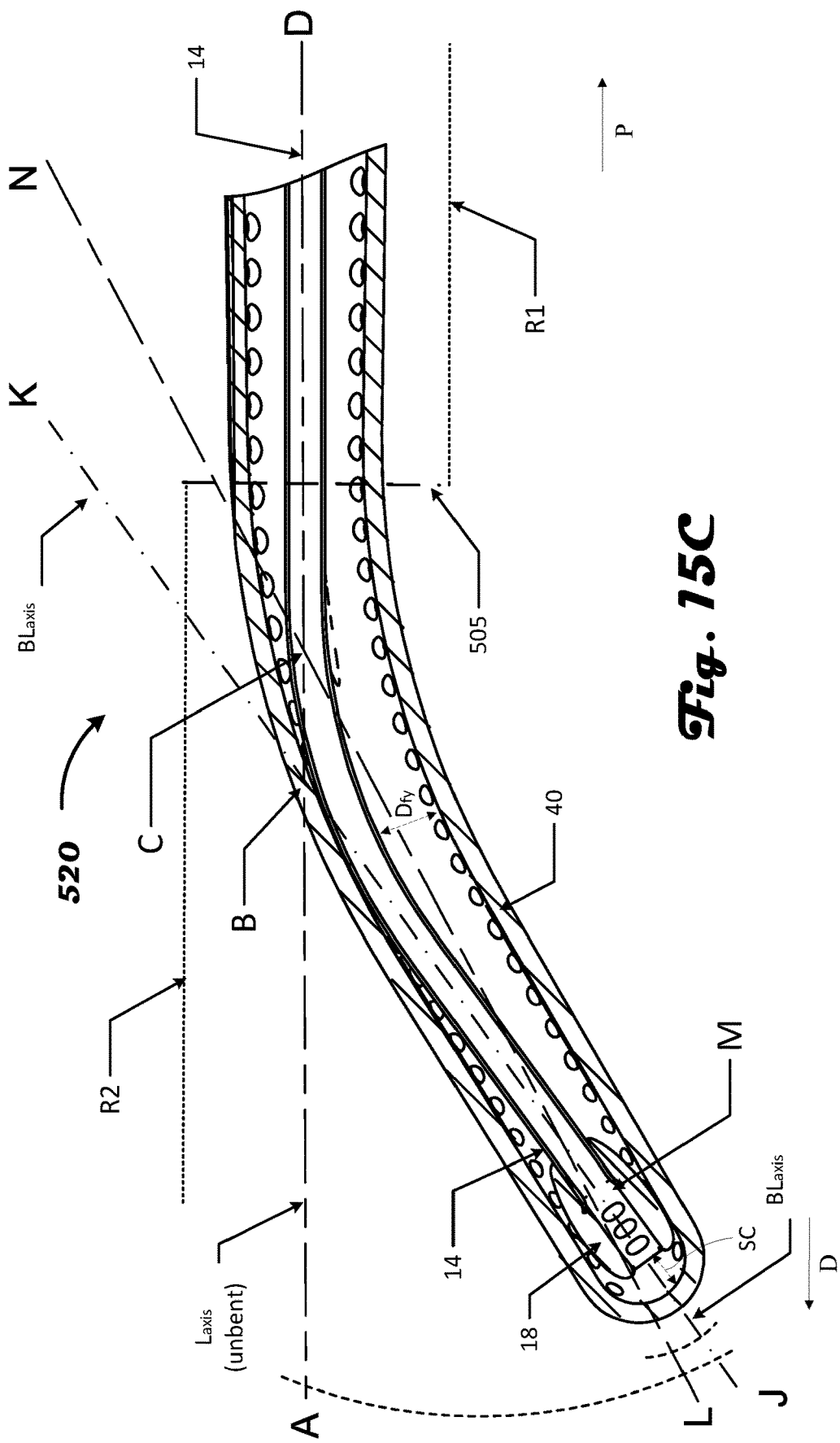
Figure 15D:
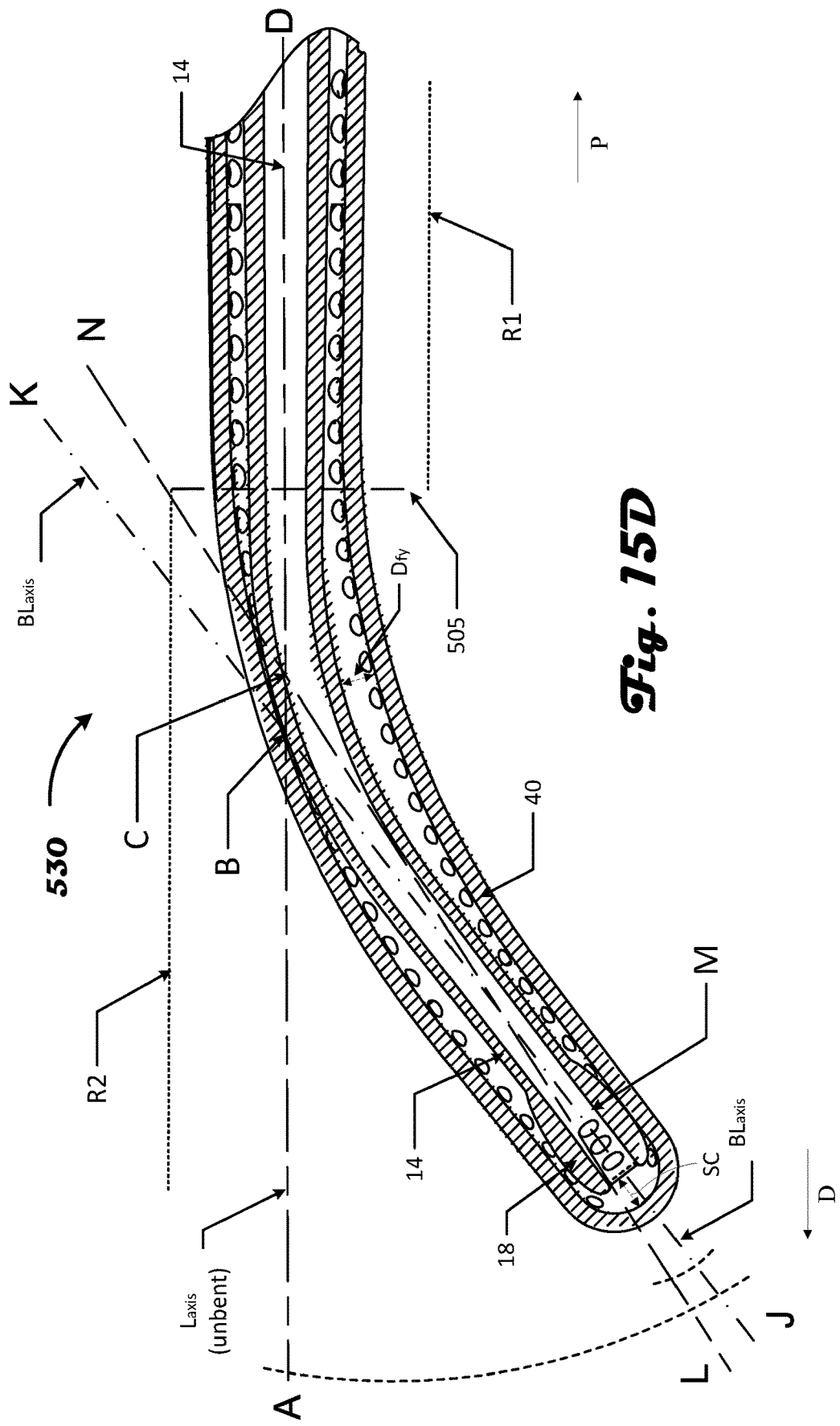

FIG. 15B is a schematic representation that depicts some of the various axial and angular relationships of FIG. 15A without the aspirator and sleeve to allow the various angles, axis, and distances to be more easily viewed. FIGS. 15C and 15D show additional embodiments 520, 530 of aspirator and sleeve combinations that include clearances SC that vary relative to the SC of combination 500 in FIG. 15A. The angles, line segments and coordinate system of FIG. 15A are also used to depict similarly oriented segments and angles for aspirator assemblies 520, 530 in FIGS. 15C and 15D even though the distances and angles in embodiments 520, 530 differ based on changes to one or more design parameters such as differing SC values. The assembly of these elements, sleeve and tubular member, 500, 520, 520 relative to the distal end of the sleeve can be described in terms of various axial, angular and other metrics to describe certain features relating to engineered clearances within the sleeve 40.

In one embodiment, the skewing angles for FIG. 15A vary based on one or more parameters for combination device 500 including an engineered clearance SC. For example, in one embodiment angle ABJ ranges from about 24° to about 32°. In one embodiment angle ABJ is 28°±4°. For example, in one embodiment angle LMJ ranges from about 5° to about 15°. In one embodiment angle LMJ is 10°±5°.

In one embodiment, the skewing angles for FIG. 15C vary based on one or more parameters for combination device 520 including an engineered clearance SC. For example, in one embodiment angle ABJ ranges from about 33.5° to about 41.5°. In one embodiment angle ABJ is 37.5°±40. For example, in one embodiment angle LMJ ranges from about 2° to about 6°. In one embodiment angle LMJ is 4°±2°.

In one embodiment, the skewing angles for FIG. 15D vary based on one or more parameters for combination device 530 including an engineered clearance SC. For example, in one embodiment angle ABJ ranges from about 32° to about 40°. In one embodiment angle ABJ is 36°±4°. For example, in one embodiment angle LMJ ranges from about 5° to about 15°. In one embodiment angle LMJ is 10°±5°.

In one embodiment, one or more clearances, such as a radial and/or an axial clearance between inner sleeve wall and suction head, is desirable because it constrains the shape of triangle BMC as shown in FIGS. 15A, 15C, and 15D. The various clearances selected constraining the skewing angles which in turn shift and flatten triangle BMC such the sleeve is not tightly coupled against the tubular member or otherwise interfering with it during and/or after assembly. A tight fit between sleeve and tubular member causes sharp bending and makes assembly the sleeve relative to the tubular member, suction head and handle difficult or not possible in some cases.

Prior to discussing some of the clearance features of the disclosure it is informative to consider some geometric axial and angular transformations that can occur as a result of using a tubular member with one or more bends. The various sets of axis and angles can be understood by considering an aspirator with a straight tubular member and a straight sleeve. In such an example, the longitudinal axis of the tubular member and the sleeve would be substantially aligned such that there was a common longitudinal axis for the tubular member, the handle of the aspirator and the sleeve.

Now, if the straight sleeve and the straight tubular member were simultaneously bent, the longitudinal axis shared by both sleeve and tubular member would shift and deviate from the first shared axis. In turn, the bent portion of the sleeve and the bent portion of the tubular member would each have their own relative axis through their respective portions. Skewing of various axis because of tubular member bending and sleeve bending result in different axes and angles which constrain the arrangement of device components.

Constraining the arrangement and position of device components via various angles and certain clearance distances SC allows for a range of product designs that use a sleeve and an aspirator that are easier to assemble and that can, in some embodiments, have a more gradual sleeve bend in assembled form as a result of the clearance selected. This more gradual sleeve bend allows the assemble device to resemble a Poole suction device in one embodiment. These angles are relevant when designing the clearances associated with the interplay of sheath, suction head and tubular member when the aspirator and sheath are combined. As a result, the engineered clearances possible can be constrained by these various angles, generally referred to as skewing angles.

As shown in FIGS. 15A, 15B 15C, and 15D, the aspirator has a longitudinal axis $L_{axis}$ (unbent) that is disposed within the tubular member 14 and the handle (not shown). On the various line segments, alternatively described as axes, points A, B, C, D, L, M, N, J and K are shown which define various line segments as end points and also can be used to identify various angles. These coordinates can be used to depict clearance SC and the skewing angles in exemplary embodiments 500, 520 and 530 which correspond to different exemplary product designs having differing SC values or other differing angles or proportions. Three points of intersection B. C, and M for segments or axis are shown. The bend of the tubular member 14 that contacts or is otherwise closest to the inner wall of the sleeve 40 occurs at point B. The line segment AD and component line segments AB and BD thereof are disposed along the longitudinal axis $L_{axis}$. Line segment or axis LN includes line segments LM, MC, and CN as component line segments. Line segment or axis JK includes line segments JM, MB, and BK as component line segments.

The portion of the aspirator (disposed on the distal side of the figure) that includes the suction head 18 and the section the tubular member that continues after the bend B has its own relative longitudinal axis disposed along segment JB. The bending of the tubular member 14 effectively transforms the unbent longitudinal axis of segment AD ($L_{axis}$) to a bent longitudinal axis JK. Similarly, the bending of the sleeve 40 from a straight longitudinal axis that tracks axis AD to a bent longitudinal axis LCN results in a skewing of the bent distal sleeve portion and the bent distal tubular member portion.

As a result, angles LMJ, ABL, ABJ, and ACL can vary over different ranges and are constrained based on the engineered clearance value for a particular aspirator and sleeve assembly design. Thus, one or more skewing angles are a function or otherwise permitted based on the engineered clearance SC for a given embodiment such as 500, 520, 530 and others as suited for particular aspirator and sleeve dimensions and relative clearances associated with such dimensions and sleeve properties. This angle and the other angles are permitted or constrained by the SC value in one embodiment. Thus, in one embodiment, an engineered clearance between inner wall of sleeve and the suction head, such as the side of suction head or from the distal end face of the suction, facilitates the assembly process, and reduces the sleeve skewing or bending from the tubular member. In this way, the skewing angles vary as a function of or are constrained by the engineered clearances. This features works in conjunction with substantially cylindrical sleeve mount to ease assembly.

Figure 16:
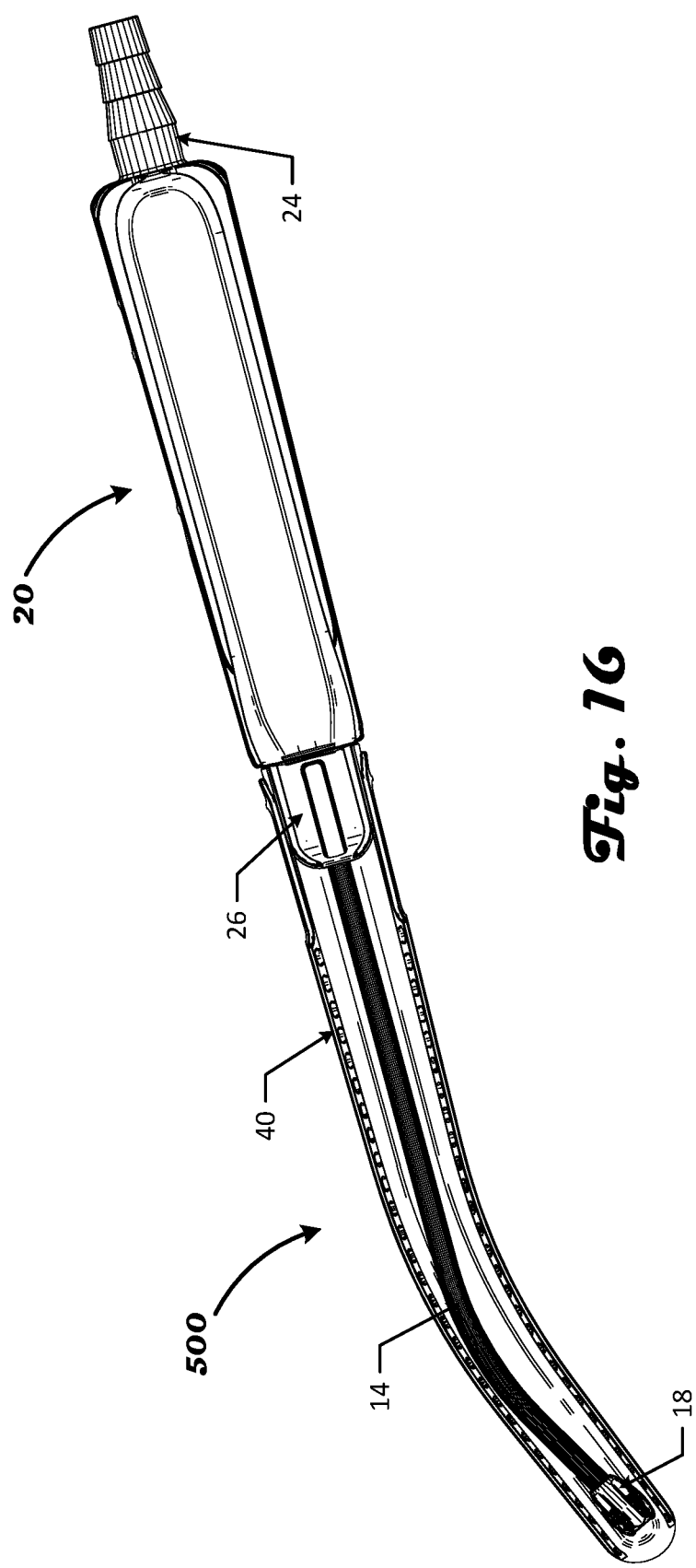
FIG. 16 is a cutaway view depicting a tubular member and suction head of an aspirator while engaging with the aspirator sleeve, in accordance with an illustrative embodiment of the disclosure.

FIG. 16 illustrates a partially cutaway view of engineering clearance associated with the suction head 18 and its respective engagement with sleeve 40, including bending of tubular member 14, in a fully engaged configuration. For example, the substantially cylindrical profile of the sleeve coupling area 26 (e.g., the mating area) of the handle member 20 is mated with the sleeve 40.

Providing a clearance allows for utilization of familiar product shapes and forms, reminiscent of classic suction instrument designs. For example, the handle member 20 may be reminiscent to the classic Andrews-Pynchon design. When the sleeve 40 is assembled, the elastic sleeve conforms to the curvilinear profile of the handle member 20 (e.g., the bending of tubular member 14). In one embodiment, a clearance has been engineered, into the distal area (e.g., the distal sleeve end portion 45 of the sleeve 40) to allow the sleeve 40 to have a gradual bend. The gradual nature of the bend and the degree of bending results in a combination of sleeve 40 and handle member 20 that visually and tactilely more closely approximate those of straight, traditional, Poole-type suction handle. This gradual bend is obtained by setting one or more skewing angles such that one or more skewing angle ranges from greater than about 1 degree to about 3 degrees. In one embodiment, the skewing angle is greater than about 2 degrees and less than about 10 degrees. In another embodiment, the angle between the longitudinal axis and the sleeve longitudinal axis, ranges from greater than about 20 degrees to less than about 45 degrees.

In an example embodiment, gradual bending of the assembly may further include bearing flats near the suction head 18 of the sleeve 40. As shown in FIG. 7A, optionally bearing flats, a molded rib or other structure that is part of the sleeve or another component that is adhered to or otherwise incorporated as part of the sleeve can optionally be disposed in region 80. In one embodiment, bearing flats of the sleeve 40 are designed to interface with the plurality of lobes or protuberances of a suction head. Accordingly, the bearing flats are typically disposed closer to the distal sleeve end portion 45 of the sleeve 40. In various embodiments, these flats are not used.

The protrusions of the suction head form an exemplary cruciform cross-section (e.g., the cross-section defined by suction head projections 17 of the suction head 18 and aid the process of sleeve assembly in some implementations. In one embodiment, the assembled suction set/combination device is configured to have a gradual bend with ribs or other elongate guides disposed within the sleeve and near the opening of the sleeve at its base. These ribs or guides or other bearing flats are designed to interface with the cruciform cross-section of the suction head. In addition, the flats can help simplify the process of sleeve assembly where the sleeve is elastically deformed to accommodate a bent cannula and the curvilinear profile of the suction handle.

In one embodiment, the bearing flats provide a degree of structural support or reinforcement along certain regions of the sleeve. As a result, the bearing flats provide additional support and tactile feedback to a user combining the device when the sleeve 40 is elastically deforming to accommodate the curvilinear profile of the suction handle. In one embodiment, four bearing flats are utilized, one for each protrusion or lobe of the cruciform cross-section of the suction head. In one embodiment, a bearing flat is paired with each lobe or protrusion of the suction head. In one embodiment, the bearing flats are sized and arranged to align with a plurality of lobes of suction head having a cruciform cross-section. The number of lobes and bearing flats are typically less than about six.

By providing a set of components, such as an aspirator and a sleeve, a clearance at the suction head area is deliberately formed to accommodate degrees of skewing or deflection relative to one or more axes. Specifically, the clearance accommodates skewing or deflection of the axis of the suction head 18 and tubular member 14 relative to the axis of the sleeve 40 in that area. This skewing differential between the tubular member 14 and the sleeve 40 is illustrated by FIGS. 15A, 15C and 15D.

To provide an alternate reference frame relative to the line segments and coordinates of FIGS. 15A-15, two directional parameters $D_{fx}$ and $D_{fy}$ are shown with regard to the bent sleeve and handle assembly and provide exemplary ranges or distances over which a clearance can be formed relative to the inner sleeve wall and a normal measure relative to a surface of a suction head or the tubular member. In one embodiment, $D_{fx}$ and $D_{fy}$ result from the clearances SC chosen near the suction head, which limit how close it can come to the inner wall of the sleeve.

In one embodiment, the installation of a sleeve relative to a suction device can be configured such that a tight fit between the terminus of the tubular member (e.g., suction head 18) and sleeve (e.g., sleeve 40) in the suction head area of the assembly. This tighter fit may force the axis of the suction head and tube to be coincident with that of the sleeve in the suction head area. Functionally, this leads to a noticeably bent suction device when assembled for Poole-type suction. The tight fit of the sleeve and suction head additionally leads to undesirable resistance during assembly of the sleeve (e.g., mating of the sleeve).

Combination of Assembled Handle and Drainage Channels

The device discussed above improves the functionality of the handle member 20 when the sleeve 40 is combined with the handle to form a Poole-type suction device. Poole-type suction involves a process of aspirating a volume of irrigation and body fluids from an open-surgery wound (e.g., wound 800) as shown with regard to FIG. 8A. A Poole-type suction device creates a drainage and suction path, to a point of suction, via channels formed by interleaved shells. Traditional Poole-type suction devices have a small handle area that primarily functions to provide hardware to couple an outer rigid sleeve. This rigid sleeve creates the drainage/suction path. Therefore, the suction set may be referred to as a Poole-type suction device when the sleeve 40 is assembled to the handle member 20. Effectively, one feature of the disclosure relates a method of converting a handle-based suction device such as member 20 to a Poole-type suction device. In general, the methods described herein provide tactile feedback to a user with regard to a provided sleeve and aspirator and also ease assembly thereof.

Some designs may not utilize the entire handle as is the case for a typical Poole-type suction device. For example, designs may completely ventilate one side of the handle into the internal cavity formed by the sleeve and the suction handle. However, the top side of the suction handle does not provide this functionality entirely. For example, regions on the top of the handle are a typical place at which ventilation is blocked.

By comparison, the device disclosed herein provides channeling on both the top and bottom sides of the handle member 20. This integration, between the handle member 20 and the sleeve 40 effectively makes the entire assembly a Poole-type suction device. Moreover, this assembly is not sensitive to orientation in the wound (e.g., top side suction vs. bottom side suction). With the straighter profile of the sleeve 40, there may be a tendency for the operator to disregard orientation of the Poole-type suction handle member 20 during use. By implementing complete double-sided venting, Poole-type suction performance is improved regardless of orientation and user actions.

In one embodiment, the aspirator is of a singular construction or integral such that its components or subassemblies are all a common material such as a molded polymer or metal. An all polymer or all metal aspirators are examples of such constructions and can be described as unitary in some embodiments. In some embodiment, two or more of the components of a suction catheter can be different materials or manufactured using different processes and at different points in time. In some embodiments, an aspirator or suction catheter includes two or more of, for example, a suction head, a tubular member/cannula, an elastic sleeve and a handle member.

More generally, as used herein, the term unitary construction or unitary encompasses embodiments that are of a singular construction as well as embodiments in two parts of combined to form an assembly or combination. Thus, if a metal tube is coupled to a plastic handle and plastic suction head in some manner to form a device such as device can be referred to as unitary suction catheter. As noted above, in other embodiments, the term "unitary" can also refer to an object that is a single piece. For example, an object formed from a single injection molding, e.g., without assembly or addition of further parts can be described as unitary or having a unitary structure.

In the description, the invention is discussed in the context of surgical aspirators and sleeves; however, these embodiments are not intended to be limiting and those skilled in the art will appreciate that the invention can also be used for any applications where fluid removal and/or partial vacuum applications are required.

Although the preceding and following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the terms "about" or "approximately" are before a quantitative value, the present teachings also include the specific quantitative value itself, unless specifically stated otherwise. As used herein, the term "about" refers to a ±10% variation from the nominal value. As used herein, the term "approximately" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

What is claimed is:

1. An aspirator comprising:
   an elastic sleeve defining a sleeve inner surface;
   a handle comprising a shoulder and a sleeve coupler, the sleeve coupler defining an aperture, the handle and the sleeve coupler comprising a longitudinal axis, wherein the sleeve coupler is in relief relative to the shoulder;
   a tubular member defining a bend, the tubular member comprising a proximal tube end and a distal tube end, the proximal tube end disposed in the handle, the tubular member extending from the sleeve coupler and the aperture, the tubular member oriented to receive the elastic sleeve; and
   a suction head attached to the tubular member,
   wherein an engineered clearance is defined between the sleeve inner surface and the suction head, wherein sleeve inner surface adjacent suction head is free of suction head contacting features extending therefrom;
   wherein a section of the tubular member defines a tubular longitudinal axis,
   wherein the sleeve coupler is sized to receive the elastic sleeve such that the bend is disposed within the elastic sleeve,
   wherein a section of the elastic sleeve distal to the bend defines a sleeve longitudinal axis;
   wherein the tubular longitudinal axis is askew from the sleeve longitudinal axis such that the engineered clearance is formed thereby.

2. The aspirator of claim 1 wherein the clearance ranges from about 0.080 inches to about 0.11 inches, wherein the clearance is between the distal end face of the suction head and the sleeve inner surface.

3. The aspirator of claim 1 wherein the clearance ranges from about 0.001 inches to about 0.020 inches, wherein the clearance is between a side of the suction head and the sleeve inner surface.

4. The aspirator of claim 1 wherein the clearance ranges from about 0.005 inches to about 0.100 inches.

5. The aspirator of claim 4 wherein the clearance constrains a second skewing angle range between a portion of the sleeve and a portion of the tubular member after the bend.

6. The aspirator of claim 5 wherein the second skewing angle range is from about 5° to about 15°.

7. The aspirator of claim 5 wherein the second skewing angle range is from about 2° to about 6°.

8. The aspirator of claim 1 wherein the clearance constrains a first skewing angle range between the longitudinal axis and the sleeve longitudinal axis.

9. The aspirator of claim 8 wherein the first skewing angle range is from about 24° to about 32°.

10. The aspirator of claim 8 wherein the first skewing angle range is from about 33.5° to about 41.5°.

11. The aspirator of claim 8 wherein the first skewing angle range is from about 32° to about 40°.

12. The aspirator of claim 1, wherein combination of sleeve and aspirator result in the sleeve having a substantially straight orientation with the bend disposed therein.

13. The aspirator of claim 1 wherein a surface of the tubular member at the bend contacts the sleeve inner surface at one or more regions.

14. The aspirator of claim 1 wherein the elastic sleeve defines a plurality of vent holes, a sleeve lumen and the sleeve inner surface, the elastic sleeve comprising a sleeve tip and a sleeve rim, wherein the sleeve rim defines a sleeve opening.

15. An aspirator comprising:
   an elastic sleeve comprising a proximal sleeve end, a distal sleeve end and an inner sleeve wall, the proximal sleeve end and inner sleeve wall defining an elongate tapered cavity, wherein the elongate tapered cavity defines a handle coupling region, a bend region, a suction head receiving region; and a first clearance region; and
   a suction head defining a suction head bore, a distal suction head end face and an output aperture, wherein inner sleeve wall adjacent suction head is free of suction head contacting features extending therefrom;
   a handle comprising a sleeve coupler and a suction connector barb, the handle defining an elongate cavity, the sleeve coupler defining a handle opening, the elongate cavity in fluid communication with the handle opening and the suction connector barb; and
   a hollow tubular member comprising a flared end, a proximal tubular end and a bend disposed between the flared end and the proximal tubular end, the flared end extending from the output aperture, the proximal tubular end extending from the sleeve coupler, wherein a first clearance distance normal to distal suction head end face is formed in the first clearance region when sleeve coupler is disposed in the handle coupling region;
   wherein the elastic sleeve has a first longitudinal axis and a portion of the hollow tubular member after the bend has a second longitudinal axis, wherein a skewing angle between the first longitudinal axis and the second longitudinal axis is greater than about 2 degrees and less than about 10 degrees.

16. The aspirator of claim 15 wherein the first clearance distance ranges from 0.080 inches to about 0.11 inches.

17. The aspirator of claim 15 wherein the elongate tapered cavity defines a second clearance region, wherein a second clearance distance normal to surface of tubular member is formed in the second clearance region when sleeve coupler is disposed in the handle coupling region.

18. The aspirator of claim 17 wherein the second clearance region is disposed between the first clearance region and the bend region.

19. The aspirator of claim 17 wherein the second clearance distance ranges from about 0.001 inches to about 0.020 inches.

20. The aspirator of claim 15 wherein the first clearance ranges from about 0.005 inches to about 0.100 inches.

21. The aspirator of claim 15 wherein combination of the elastic sleeve, the suction head, the hollow tubular member and sleeve coupler result in the sleeve having a substantially straight orientation with the bend disposed therein.

22. A method of assembling a suction device comprising:
providing an aspirator comprising a handle comprising a sleeve mount and a tubular member extending from the sleeve mount, the tubular member comprising a bend;
providing an elastic sleeve defining an opening, an inner sleeve wall and a lumen to receive the sleeve mount and tubular member; and
constraining a skewing angle and one or more clearances between the inner sleeve wall and portions of the tubular member such that an angle by which the elastic sleeve bends relative to a longitudinal axis of the handle is reduced such that the elastic sleeve is substantially straight even though the bend is disposed therein.

* * * * *